(12) United States Patent
Brasca et al.

(10) Patent No.: US 8,481,585 B2
(45) Date of Patent: Jul. 9, 2013

(54) SUBSTITUTED PYRROLO-PYRAZOLE DERIVATIVES AS KINASE INHIBITORS

(75) Inventors: Maria Gabriella Brasca, Cusago (IT); Raffaella Amici, Codogno (IT); Daniele Fancelli, Milan (IT); Marcella Nesi, Saronno (IT); Paolo Orsini, Legnano (IT); Fabrizio Orzi, Milan (IT); Patrick Roussel, Mulhouse (FR); Anna Vulpetti, Brugherio (IT); Paolo Pevarello, Pavia (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 0 days.

(21) Appl. No.: 13/614,499

(22) Filed: Sep. 13, 2012

(65) Prior Publication Data

US 2013/0017170 A1  Jan. 17, 2013

Related U.S. Application Data

(63) Continuation of application No. 12/181,772, filed on Jul. 29, 2008, which is a continuation of application No. 10/539,145, filed as application No. PCT/EP03/50942 on Dec. 4, 2003, now Pat. No. 7,407,971.

(60) Provisional application No. 60/434,952, filed on Dec. 19, 2002.

(51) Int. Cl.
*A61K 31/4162* (2006.01)
*A61K 31/454* (2006.01)
*C07D 487/02* (2006.01)
*C07D 401/14* (2006.01)

(52) U.S. Cl.
USPC ............... 514/407; 548/357.5; 548/359.5; 514/322; 546/199

(58) Field of Classification Search
USPC ........... 514/322, 253, 407; 546/199; 544/371; 548/357.5, 359.5
See application file for complete search history.

(56) References Cited

U.S. PATENT DOCUMENTS

| 3,526,633 | A | 9/1970 | Gadekar et al. |
| 7,407,971 | B2 | 8/2008 | Brasca et al. |
| 7,531,531 | B2 | 5/2009 | Fancelli et al. |
| 7,541,354 | B2 | 6/2009 | Fancelli et al. |
| 2003/0171357 | A1 | 9/2003 | Fancelli et al. |

FOREIGN PATENT DOCUMENTS

| WO | WO 02/12242 A | 2/2002 |
| WO | WO 02/070515 A | 9/2002 |

OTHER PUBLICATIONS

U.S. Final Office Action dated Apr. 27, 2010 from parent U.S. Appl. No. 12/181,772.
U.S. Office Action dated Oct. 20, 2009 from parent U.S. Appl. No. 12/181,772.
U.S. Final Office Action dated Sep. 11, 2007 from parent U.S. Appl. No. 10/539,145.
U.S. Office Action dated Feb. 26, 2007 from parent U.S. Appl. No. 10/539,145.

*Primary Examiner* — Charanjit Aulakh
(74) *Attorney, Agent, or Firm* — Scully, Scott, Murphy & Presser, P.C.

(57) ABSTRACT

Compounds represented by formula (Ia) or (Ib) and wherein R and $R_1$ are as defined in the description, and pharmaceutically acceptable salts thereof, are disclosed; the said compounds are useful in the treatment of cell cycle proliferative disorders, e.g. cancer, associated with an altered cell cycle dependent kinase activity.

14 Claims, No Drawings

SUBSTITUTED PYRROLO-PYRAZOLE DERIVATIVES AS KINASE INHIBITORS

CROSS REFERENCE TO RELATED APPLICATIONS

The present application is a continuation of co-pending application having U.S. Ser. No. 12/181,772, filed on Jul. 29, 2008, which is a continuation of application having U.S. Ser. No. 10/539,145, filed on May 4, 2006, now U.S. Pat. No. 7,407,971, which is a 371 of International Application having Serial No. PCT/EP2003/50942, filed on Dec. 4, 2003, which claims benefit of U.S. Provisional Application having Ser. No. 60/434,952, filed on Dec. 19, 2002, the contents of all of which are incorporated herein by reference.

BACKGROUND OF THE INVENTION

1. Field of the Invention

The present invention relates to pyrrolo-pyrazole derivatives, to a process for their preparation, to pharmaceutical compositions comprising them, and to their use as therapeutic agents, particularly in the treatment of cancer and cell proliferation disorders.

2. Discussion of the Background

Several cytotoxic drugs such as, e.g., fluorouracil (5-FU), doxorubicin and camptothecins, damage DNA or affect cellular metabolic pathways and thus cause, in many cases, an indirect block of the cell cycle. Therefore, by producing an irreversible damage to both normal and tumor cells, these agents result in a significant toxicity and side-effects.

In this respect, compounds capable of functioning as highly specific antitumor agents by selectively leading to tumor cell arrest and apoptosis, with comparable efficacy but reduced toxicity than the currently available drugs, are desirable.

It is well known that progression through the cell cycle is governed by a series of checkpoint controls, otherwise referred to as restriction points, which are regulated by a family of enzymes known as the Cyclin-dependent kinases (Cdk). In turn, the Cdks themselves are regulated at many levels such as, for instance, binding to cyclins.

The coordinated activation and inactivation of different Cdk/Cyclin complexes is necessary for normal progression through the cell cycle. Both the critical G1-S and G2-M transitions are controlled by the activation of different Cdk/Cyclin activities. In G1, both Cdk4/Cyclin D and Cdk2/Cyclin E are thought to mediate the onset of S-phase. Progression through S-phase requires the activity of Cdk2/Cyclin A whereas the activation of Cdc2/Cyclin A (Cdk1) and Cdc2/cyclin B are required for the onset of mitosis. For a general reference to cyclins and cyclin-dependent kinases see, for instance, Kevin R. Webster et al, in Exp. Opin. Invest. Drugs, 1998, Vol. 7(6), 865-887.

Checkpoint controls are defective in tumor cells due, in part, to disregulation of cdk activity. For example, altered expression of cyclin E and cdks has been observed in tumor cells, and deletion of the cdk inhibitor p27 KIP gene in mice has been shown to result in a higher incidence of cancer.

Increasing evidence supports the idea that the cdks are rate-limiting enzymes in cell cycle progression and, as such, represent molecular targets for therapeutic intervention. In particular, the direct inhibition of cdk/cyclin kinase activity should be helpful in restricting the unregulated proliferation of a tumor cell.

SUMMARY OF THE INVENTION

It is an object of the invention to provide compounds which are useful in treating cell proliferative disorders caused by and/or associated with an altered cell cycle dependent kinase activity. It is another object to provide compounds which have cdk/cyclin kinase inhibitory activity.

The present inventors have now discovered that certain pyrazole compounds are endowed with cdk/cyclin kinase inhibitory activity and are thus useful in therapy as antitumor agents and lack, in terms of both toxicity and side effects, the aforementioned drawbacks associated with currently available antitumor drugs.

More specifically, the pyrazole derivatives of the invention are useful in the treatment of a variety of cancers including, but not limited to: carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma.

Due to the key role of cdks in the regulation of cellular proliferation, these pyrazole derivatives are also useful in the treatment of a variety of cell proliferative disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The compounds of the invention may be useful in treatment of Alzheimer's disease, as suggested by the fact that cdk5 is involved in the phosphorylation of tau protein (J. Biochem. 117, 741-749, 1995).

The compounds of this invention, as modulators of apoptosis, may also be useful in the treatment of cancer, viral infections, prevention of AIDS development in HIV-infected individuals, autoimmune diseases and neurodegenerative disorders. The compounds of this invention may be useful in inhibiting tumor angiogenesis and metastasis, as well as in the treatment of organ transplant rejection and host versus graft disease.

The compounds of the invention may also act as inhibitor of other protein kinases, e.g., protein kinase C in different isoforms, Met, PAK-4, PAK-5, ZC-1, STLK-2, DDR-2, Aurora 1, Aurora 2, Bub-1, PLK, Chk1, Chk2, HER2, raf1, MEK1, MAPK, EGF-R, PDGF-R, FGF-R, IGF-R, PI3K, weel kinase, Src, Abl, Akt, MAPK, ILK, MK-2, IKK-2, Cdc7, Nek, and thus be effective in the treatment of diseases associated with other protein kinases.

The compounds of the invention are also useful in the treatment and prevention of radiotherapy-induced or chemotherapy-induced alopecia.

Accordingly, the present invention provides a method for treating cell proliferative disorders caused by and/or associated with an altered cell cycle dependent kinase activity, by administering to a mammal in need thereof an effective amount of a pyrazole derivative represented by formula (Ia) or (Ib)

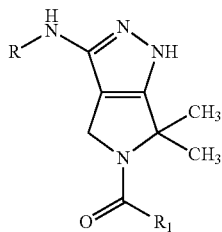

(Ia)

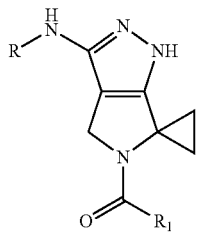

(Ib)

wherein
R is a group —COR$^a$, —CONHR$^a$ or —CONR$^a$R$^b$ wherein R$^a$ and R$^b$ are, each independently, hydrogen or an optionally substituted group selected from straight or branched C$_1$-C$_6$ alkyl, C$_3$-C$_6$ cycloalkyl, aryl, arylalkyl, heterocyclyl or heterocyclylalkyl or; together with the nitrogen atom to which they are bonded, R$^a$ and R$^b$ may form an optionally substituted 5 or 6 membered heterocycle optionally containing one additional heteroatom or heteroatomic group selected among N, NH, O or S;

R$_1$ is selected from the group consisting of:
a) straight or branched C$_3$-C$_4$ alkyl;
b) cycloalkyl, cycloalkyl-alkyl or alkyl-cycloalkyl wherein the cycloalkyl moiety comprises any C$_3$-C$_6$ cycloalkyl group and wherein the alkyl moiety comprises any straight or branched C$_1$-C$_4$ alkyl group:
c) 3-methylthienyl-2-yl; 2-thienyl; phenyl; 2,6-difluorophenyl; 4-(aminosulfonyl)phenyl; 4-(dimethylaminomethyl)phenyl; 4-(4-methylpiperazinyl)methyl-phenyl;
d) a group of formula (IIa) or (IIb):

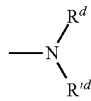

(IIa)

(IIb)

wherein, in formula (IIa), the cycle represents a 5 to 7 membered heterocyclic ring wherein X, directly linked to the rest of the molecule, represents a carbon or nitrogen atom; Y is a carbon, nitrogen, oxygen or sulfur atom or it is an NH group, provided that at least one of X and Y is other than a carbon atom; R$^c$ is, independently from each other and in any one of the free positions of the heterocyclic ring of formula (IIa), a halogen atom or hydroxy group or it is an optionally substituted group selected from straight or branched C$_1$-C$_6$ alkyl, C$_3$-C$_6$ cycloalkyl, aryl, arylalkyl, heterocyclyl, heterocyclylalkyl, amino, aminocarbonyl, carboxy, oxo (═O), alkoxycarbonyl, alkylcarbonyl or arylcarbonyl; and n is 0 or an integer from 1 to 4;

e) a group of formula (IIc) or (IId):

(IIc)

(IId)

wherein R$^d$, R$'^d$ and R$^e$ represent, the same or different and independently from each other, a hydrogen atom or a straight or branched C$_1$-C$_6$ alkyl optionally substituted by one or more groups selected from hydroxy (—OH), aminocarbonyl (—CONH$_2$) or methylaminocarbonyl (—CONHCH$_3$);

provided that in formula (Ia), when R$_1$ is a group of formula (IIc) and one of R$^d$ or R$'^d$ is a hydrogen atom whilst the other of R$^d$ or R$'^d$ is ethyl or n-butyl, then R is other than —COR$^a$ with R$^a$ as 3-bromophenyl, benzyl, 4-tert-butylphenyl, 4-tert-butylphenylmethyl, 4-fluorophenylmethyl, cyclopropyl or 2-naphthylmethyl;

or a pharmaceutically acceptable salt thereof.

In a preferred embodiment of the method described above, the cell proliferative disorder is selected from the group consisting of cancer, Alzheimer's disease, viral infections, autoimmune diseases and neurodegenerative disorders.

Specific types of cancer that may be treated include carcinoma, squamous cell carcinoma, hematopoietic tumors of myeloid or lymphoid lineage, tumors of mesenchymal origin, tumors of the central and peripheral nervous system, melanoma, seminoma, teratocarcinoma, osteosarcoma, xeroderma pigmentosum, keratoxanthoma, thyroid follicular cancer, and Kaposi's sarcoma.

In another preferred embodiment of the method described above, the cell proliferative disorder is selected from the group consisting of benign prostate hyperplasia, familial adenomatosis polyposis, neuro-fibromatosis, psoriasis, vascular smooth cell proliferation associated with atherosclerosis, pulmonary fibrosis, arthritis, glomerulonephritis and post-surgical stenosis and restenosis. In addition, the inventive method provides tumor angiogenesis and metastasis inhibition as well as treatment of organ transplant rejection and host versus graft disease. The inventive method may also provide cell cycle inhibition or cdk/cyclin dependent inhibition.

In addition to the above, the method object of the present invention provides treatment and prevention of radiotherapy-induced or chemotherapy-induced alopecia.

The present invention also provides a pyrazole derivative represented by formula (Ia) or (Ib)

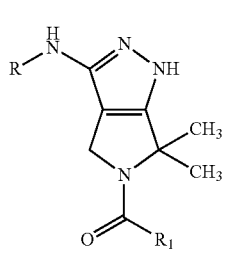

(Ia)

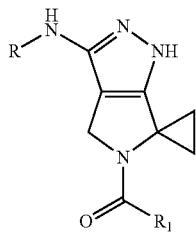

(Ib)

wherein

R is a group —COR$^a$, —CONHR$^a$ or —CONR$^a$R$^b$ wherein R$^a$ and R$^b$ are, each independently, hydrogen or an optionally substituted group selected from straight or branched C$_1$-C$_6$ alkyl, C$_3$-C$_6$ cycloalkyl, aryl, arylalkyl, heterocyclyl or heterocyclylalkyl or; together with the nitrogen atom to which they are bonded, R$^a$ and R$^b$ may form an optionally substituted 5 or 6 membered heterocycle optionally containing one additional heteroatom or heteroatomic group selected among N, NH, O or S;

R$_1$ is selected from the group consisting of:
a) straight or branched C$_3$-C$_4$ alkyl;
b) cycloalkyl, cycloalkyl-alkyl or alkyl-cycloalkyl wherein the cycloalkyl moiety comprises any C$_3$-C$_6$ cycloalkyl group and wherein the alkyl moiety comprises any straight or branched C$_1$-C$_4$ alkyl group:
c) 3-methylthienyl-2-yl; 2-thienyl; phenyl; 2,6-difluorophenyl; 4-(aminosulfonyl)phenyl; 4-(dimethylaminomethyl)phenyl; 4-(4-methylpiperazinyl)methyl-phenyl;
d) a group of formula (IIa) or (IIb):

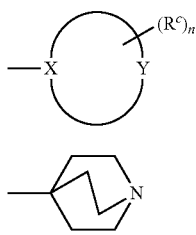

(IIa)

(IIb)

wherein, in formula (IIa), the cycle represents a 5 to 7 membered heterocyclic ring wherein X, directly linked to the rest of the molecule, represents a carbon or nitrogen atom; Y is a carbon, nitrogen, oxygen or sulfur atom or it is an NH group, provided that at least one of X and Y is other than a carbon atom; R$^c$ is, independently from each other and in any one of the free positions of the heterocyclic ring of formula (IIa), a halogen atom or hydroxy group or it is an optionally substituted group selected from straight or branched C$_1$-C$_6$ alkyl, C$_3$-C$_6$ cycloalkyl, aryl, arylalkyl, heterocyclyl, heterocyclylalkyl, amino, aminocarbonyl, carboxy, oxo (=O), alkoxycarbonyl, alkylcarbonyl or arylcarbonyl; and n is 0 or an integer from 1 to 4;
e) a group of formula (IIc) or (IId):

(IIc)

(IId)

wherein R$^d$, R'$^d$ and R$^e$ represent, the same or different and independently from each other, a hydrogen atom or a straight or branched C$_1$-C$_6$ alkyl optionally substituted by one or more groups selected from hydroxy (—OH), aminocarbonyl (—CONH$_2$) or methylaminocarbonyl (—CONHCH$_3$);

provided that in formula (Ia), when R$_1$ is a group of formula (IIc) and one of R$^d$ or R'$^d$ is a hydrogen atom whilst the other of R$^d$ or R'$^d$ is ethyl or n-butyl, then R is other than —COR$^a$ with R$^a$ as 3-bromophenyl, benzyl, 4-tert-butylphenyl, 4-tert-butylphenylmethyl, 4-fluorophenylmethyl, cyclopropyl or 2-naphthylmethyl;

or a pharmaceutically acceptable salt thereof.

The present invention also includes methods for the synthesis of the pyrazole derivatives represented by formulae (Ia) or (Ib) that, unless otherwise provided, may be conveniently grouped and defined as compounds of formula (I). Pharmaceutical compositions comprising the pyrazole derivatives of formula (I) are also included in the present invention.

A more complete appreciation of the invention and many of the attendant advantages thereof will be readily obtained as the same becomes better understood by reference to the following detailed description.

DETAILED DESCRIPTION OF THE INVENTION

Several heterocyclic compounds are known in the art as protein kinase inhibitors. As an example, 2-carboxamido-pyrazoles and 2-ureido-pyrazoles, and derivatives thereof, have been disclosed as protein kinase inhibitors in the international patent applications WO 01/12189, WO 01/12188, WO 02/48114 and WO 02/70515, all in the name of the applicant itself.

Fused bicyclic compounds comprising pyrazole moieties and possessing kinase inhibitory activity have been also disclosed in WO 00/69846 and WO 02/12242 as well as in WO 03/028720 (PCT/EP02/10534 claiming priority from U.S. patent application Ser. No. 09/962,162 of Sep. 26, 2001) and copending PCT/EP03/04862 (claiming priority from U.S. patent application 60/381,092 of May 17, 2002), all in the name of the applicant itself.

The compounds object of the present invention fall within the scope of the general formula of the aforementioned WO 02/12242, herewith incorporated by reference, but are not specifically exemplified therein.

Unless otherwise specified, when referring to the compounds of formula (I) per se as well as to any pharmaceutical composition thereof or to any therapeutic treatment comprising them, the present invention includes all of the hydrates, solvates, complexes, metabolites and prodrugs of the compounds of this invention. Prodrugs are any covalently bonded compounds, which release the active parent drug according to formula (I) in vivo.

A metabolite of a compound of formula (I) is any compound into which this same compound of formula (I) is converted, in vivo, for instance upon administration to a mammal in need thereof.

Typically, without however representing a limiting example, upon administration of a compound of formula (I), this same derivative may be converted into a variety of compounds, for instance including more soluble derivatives like hydroxylated derivatives, which are easy to be excreted. Hence, depending upon the metabolic pathway thus occurring, any of these hydroxylated derivatives may be regarded as a metabolite of the compounds of formula (I).

If a chiral center or another form of an isomeric center is present in a compound of the present invention, all forms of such isomer or isomers, including enantiomers and diastereomers, are intended to be covered herein. Compounds containing a chiral center may be used as a racemic mixture, an enantiomerically enriched mixture, or the racemic mixture may be separated using well-known techniques and an individual enantiomer may be used alone. In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

In the present description, unless otherwise specified, with the term straight or branched $C_1$-$C_6$ alkyl, hence comprehensive of $C_1$-$C_4$ alkyl, we intend any of the groups such as, for instance, methyl, ethyl, n-propyl, isopropyl, n-butyl, isobutyl, tert-butyl, sec-butyl, n-pentyl, n-hexyl, and the like.

With the term $C_3$-$C_6$ cycloalkyl we intend, unless otherwise provided, a cycloaliphatic ring such as cyclopropyl, cyclobutyl, cyclopentyl and cyclohexyl. The term aryl includes carbocyclic or heterocyclic hydrocarbons with from 1 to 2 ring moieties, either fused or linked to each other by single bonds, wherein at least one of the rings is aromatic; if present, any aromatic heterocyclic hydrocarbon also referred to as heteroaryl group, comprises a 5 to 6 membered ring with from 1 to 3 heteroatoms or heteroatomic groups selected among N, NH, O or S.

Examples of aryl groups according to the invention are, for instance, phenyl, biphenyl, α- or β-naphthyl, dihydronaphthyl, thienyl, benzothienyl, furyl, benzofuranyl, pyrrolyl, imidazolyl, pyrazolyl, thiazolyl, isothiazolyl, oxazolyl, isoxazolyl, pyridyl, pyrazinyl, pyrimidinyl, pyridazinyl, indolyl, isoindolyl, purinyl, quinolyl, isoquinolyl, dihydroquinolinyl, quinoxalinyl, benzodioxolyl, indanyl, indenyl, triazolyl, and the like. Unless otherwise specified, the term heterocycle or heterocyclyl includes 5 to 6 membered saturated, partly unsaturated or fully unsaturated heterocycles with from 1 to 3 heteroatoms or heteroatomic groups selected among N, NH, O or S.

Apart from the fully unsaturated heterocycles, previously referred to as aromatic heterocycles and encompassed by the term aryl, examples of saturated or partly unsaturated heterocycles according to the invention are, for instance, pyran, pyrrolidine, pyrroline, imidazoline, imidazolidine, pyrazolidine, pyrazoline, thiazoline, thiazolidine, dihydrofuran, tetrahydrofuran, 1,3-dioxolane, piperidine, piperazine, morpholine and the like.

When referring to the compounds of the invention wherein $R_1$ is grouped under (b), $R_1$ itself may represent a given cycloalkyl group, for instance cyclopropyl; a given cycloalkyl-alkyl group, for instance cyclopropylmethyl; or even a given alkyl-cycloalkyl group, for instance methylcyclopropyl; all of which have the following formulae:

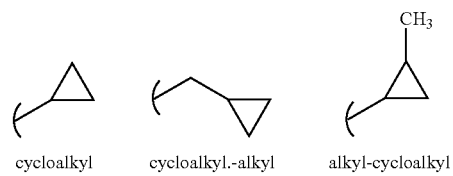

cycloalkyl   cycloalkyl.-alkyl   alkyl-cycloalkyl

When referring to the compounds of the invention wherein $R_1$ is a group of formula (IIa), the 5 to 7 membered heterocyclic ring is directly linked to the rest of the molecule through the X atom, as follows:

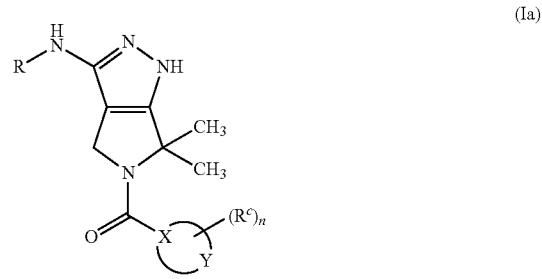

(Ia)

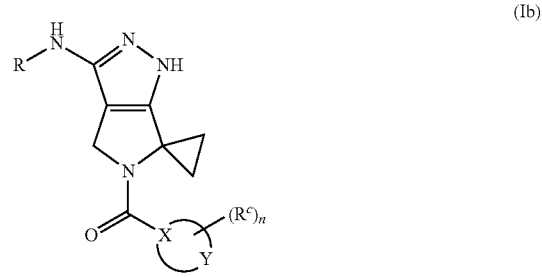

(Ib)

Examples of these 5 to 7 membered heterocycles include any 5 to 6 membered heterocycle among those already reported and, additionally, 7 membered heterocycles such as, for instance, azepine, diazepine, oxazepine and the like.

Any $R^c$, if present, is at any one of the free positions of the heterocyclic ring of formula (IIa) by replacement of a hydrogen atom.

When referring to the compounds of the invention wherein $R_1$ is a group of formula (IIc) or (IId), ureido and carbamate derivatives may be thus identified, having the following sub-formulae:

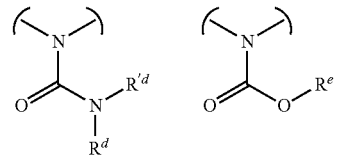

According to the present invention and unless otherwise provided, any of the above $R^a$, $R^b$ and $R^c$ groups may be optionally substituted, in any of their free positions, by one or more groups, for instance 1 to 6 groups, independently selected from: halogen, nitro, oxo groups (=O), cyano, alkyl, polyfluorinated alkyl, polyfluorinated alkoxy, alkenyl, alkynyl, hydroxyalkyl, aryl, arylalkyl, heterocyclyl, cycloalkyl, hydroxy, alkoxy, aryloxy, heterocyclyloxy, methylenedioxy, alkylcarbonyloxy, arylcarbonyloxy, cycloalkenyloxy, alkylideneaminooxy, carboxy, alkoxycarbonyl, aryloxycarbonyl, cycloalkyloxycarbonyl, amino, ureido, alkylamino, dialkylamino, arylamino, diarylamino, formylamino, alkylcarbonylamino, arylcarbonylamino, heterocyclylcarbonylamino, alkoxycarbonylamino, alkoxyimino, alkylsulfonylamino, arylsulfonylamino, formyl, alkylcarbonyl, arylcarbonyl, cycloalkylcarbonyl, heterocyclylcarbonyl, aminocarbonyl, alkylaminocarbonyl, dialkylaminocarbonyl, alkylsulfonyl, arylsulfonyl, aminosulfonyl, alkylaminosulfonyl, dialkylaminosulfonyl, arylthio and alkylthio.

In this respect, with the term halogen atom we intend a fluorine, chlorine, bromine or iodine atom.

With the term alkenyl or alkynyl we intend any of the aforementioned straight or branched $C_2$-$C_6$ alkyl groups further bearing a double or triple bond. Non limiting examples of alkenyl or alkynyl groups of the invention are, for instance, vinyl, allyl, 1-propenyl, isopropenyl, 1-butenyl, 2-butenyl, 3-butenyl, 2-pentenyl, 1-hexenyl, ethynyl, 2-propynyl, 4-pentynyl, and the like.

With the term polyfluorinated alkyl or alkoxy we intend any of the above straight or branched $C_1$-$C_6$ alkyl or alkoxy groups which are substituted by more than one fluorine atom such as, for instance, trifluoromethyl, trifluoroethyl, 1,1,1,3,3,3-hexafluoropropyl, trifluoromethoxy and the like.

With the term alkoxy, aryloxy, heterocyclyloxy and derivatives thereof we intend any of the above alkyl, aryl or heterocyclyl groups linked to the rest of the molecule through a oxygen atom (—O—).

From all of the above, it is clear to the skilled person that any group which name is a composite name such as, for instance, cycloalkylalkyl, arylalkyl, heterocyclylalkyl, alkoxy, alkylthio, aryloxy, arylalkyloxy, alkylcarbonyloxy, arylalkyl, heterocyclylalkyl and the like, have to be intended as conventionally construed by the parts from which they derive. As an example, a group such as heterocyclylalkyloxy is an alkoxy group, e.g. alkyloxy, wherein the alkyl moiety is further substituted by a heterocyclyl group, and wherein alkyl and heterocyclyl are as above defined.

Pharmaceutically acceptable salts of the compounds of formula (I) include the acid addition salts with inorganic or organic acids, e.g., nitric, hydrochloric, hydrobromic, sulfuric, perchloric, phosphoric, acetic, trifluoroacetic, propionic, glycolic, lactic, oxalic, malonic, malic, maleic, tartaric, citric, benzoic, cinnamic, mandelic, methanesulphonic, isethionic and salicylic acid. Preferably, the acid addition salt of the compounds of the invention is selected between the hydrochloride or mesylate salt.

Pharmaceutically acceptable salts of the compounds of formula (I) also include the salts with inorganic or organic bases, e.g., alkali or alkaline-earth metals, especially sodium, potassium, calcium or magnesium hydroxides, carbonates or bicarbonates, acyclic or cyclic amines, preferably methylamine, ethylamine, diethylamine, triethylamine, piperidine and the like.

A first class of preferred compounds of formula (Ia) or (Ib) is represented by the derivatives wherein R is a group —COR$^a$, R$^a$ is as above defined and R$_1$ is tert-butyl. Another class of preferred compounds of formula (Ia) or (Ib) is represented by the derivatives wherein R is a group —CONHR$^a$, R$^a$ is as above defined and R$_1$ is tert-butyl. Another class of preferred compounds of formula (Ia) or (Ib) is represented by the derivatives wherein R is a group —CONR$^a$R$^b$, R$^a$ and R$^b$ are as above defined and R$_1$ is tert-butyl.

Another class of preferred compounds of formula (Ia) or (Ib) is represented by the derivatives wherein R is as above defined and R$_1$ is a group of formula (IIa) selected from:

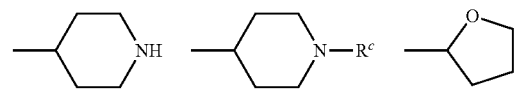

wherein R$^c$ has the above reported meanings.

Another class of preferred compounds of formula (Ia) or (Ib) is represented by the derivatives wherein R is as above defined and R$_1$ is a group of formula (IIa) selected from:

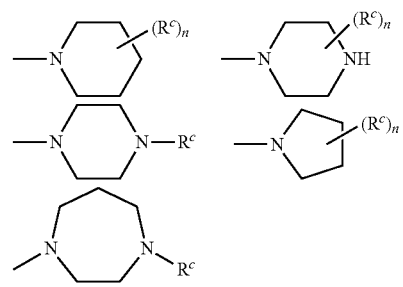

wherein n and R$^c$ have the above reported meanings.

Particularly preferred, within the above classes, are the compounds of formula (Ia) wherein R is a group —COR$^a$ with R$^a$ as 4-fluorophenyl or cyclobutyl, and R$_1$ is as defined in the general formula.

Also particularly preferred are the compounds of formula (Ia) wherein R is as defined in the general formula, and R$_1$ is a group selected from tert-butyl, 1-methyl-piperidyl-4-yl, 1-methyl-piperazinyl-4-yl, 2-(R,S)-tetrahydrofuranyl-2-yl, 2-(R)-tetrahydrofuranyl-2-yl or 2-(S)-tetrahydrofuranyl-2-yl.

For a general reference to any specific compound of formula (I) of the invention, optionally in the form of a pharmaceutically acceptable salt, see the experimental section.

As formerly indicated, a further object of the present invention is represented by the process for preparing the compounds of formula (I).

Therefore, the compounds of formula (I) and the pharmaceutically acceptable salts may be obtained by a process comprising:

a) reacting a compound of formula (IIIa) or (IIIb)

(IIIa)

(IIIb)

with acrylonitrile so as to obtain the corresponding derivative of formula (IVa) or (IVb)

(IVa)

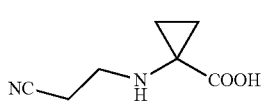
(IVb)

b) protecting the amino group of the compound of formula (IVa) or (IVb) so as to obtain the corresponding derivative of formula (Va) or (Vb)

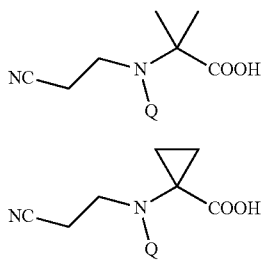
(Va)

(Vb)

wherein Q is a suitable amino protecting group;

c) reacting the compound of formula (Va) or (Vb) with a suitable alkylating agent so as to obtain the corresponding ester derivative of formula (VIa) or (VIb)

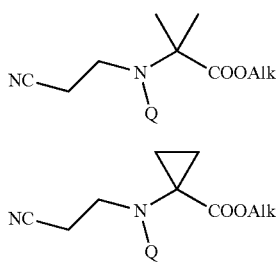
(VIa)

(VIb)

wherein Alk stands for a suitable $C_1$-$C_4$ alkyl group;

d) reacting the compound of formula (VIa) or (VIb) with sodium hydride (NaH) so as to obtain the corresponding derivative of formula (VIIa) or (VIIb)

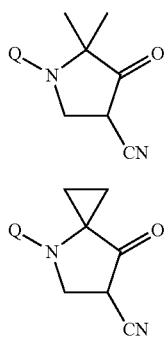
(VIIa)

(VIIb)

e) reacting the compound of formula (VIIa) or (VIIb) with hydrazine hydrate so as to obtain the compound of formula (VIIIa) or (VIIIb)

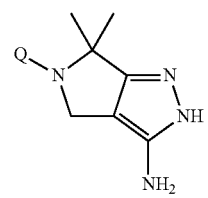
(VIIIa)

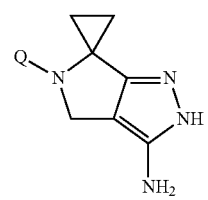
(VIIIb)

f) reacting the compound of formula (VIIIa) or (VIIIb) with ethyl chloroformate so as to obtain the derivative of formula (IXa) or (IXb), each one in any of the two regioisomeric forms

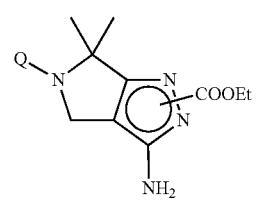
(IXa)

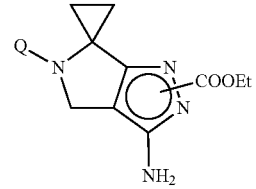
(IXb)

and reacting the compounds of formula (IXa) or (IXb) according to any one of the alternative steps (g.1), (g.2) or (g.3)

g.1) with a compound of formula (X)

$$R^aCO-Z \qquad (X)$$

wherein $R^a$ is as above defined and Z is a halogen atom, so as to obtain the compound of formula (XIa) or (XIb)

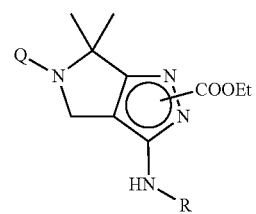
(XIa)

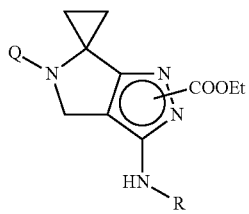
(XIb)

wherein R is a group —COR$^a$;

g.2) with a compound of formula (XII)

R$^a$—NCO  (XII)

wherein R$^a$ is as above defined so as to obtain the compound of the formula (XIa) or (XIb) wherein R is a group —CONHR$^a$; or g.3) with a suitable amine of formula (XIII) in the presence of triphosgene or of a suitable chloroformate HNR$^a$R$^b$  (XIII)

wherein R$^a$ and R$^b$ are as above defined, so as to obtain the compound of formula (XIa) or (XIb) wherein R is a group —CONR$^a$R$^b$;

h) deprotecting the amino group of the compound of formula (XIa) or (XIb) prepared according to any one of steps from (g.1) to (g.3), so as to obtain the corresponding derivative of formula (XIVa) or (XIVb)

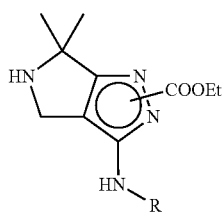
(XIVa)

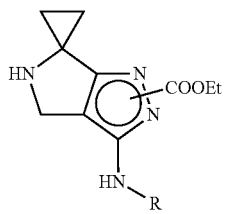
(XIVb)

wherein R has the above reported meanings; and reacting the compound of formula (XIVa) or (XIVb) according to any one of the alternative steps (i.1), (i.2), (i.3) or (i.4)

i.1) with an acyl halide derivative of formula (XV)

R$_1$—COZ  (XV)

wherein R$_1$ is as set forth in formula (Ia) or (Ib) under groups (a), (b), (c), (IIa) with X as a carbon atom and (IIb), and Z is a halogen atom, so as to obtain a compound of formula (XVIa) or (XVIb)

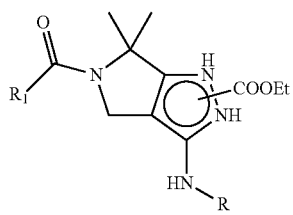
(XVIa)

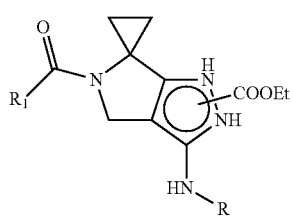
(XVIb)

wherein R and R$_1$ are as above defined;

i.2) with a 5 to 7 membered heterocyclic compound of formula (XVII) or a suitable amine of formula (XVIII), in the presence of triphosgene

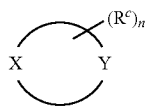
(XVII)

HN(R$^d$)R'$^d$  (XVIII)

wherein X is NH and Y, R$^c$, n, R$^d$ and R'$^d$ have the above reported meanings, so as to obtain the corresponding compounds of formula (XVIa) or (XVIb) wherein R is as above defined and R$_1$ is either a group of formula (IIa) with X as a nitrogen atom and R, Y, R$^c$ and n as above defined, or of formula (IIc) wherein R$^d$ and R'$^d$ are as above defined;

i.3) with a carboxylic acid of formula (XIX) in the presence of a suitable condensing agent

R$_1$—COOH  (XIX)

so as to obtain a compound of formula (XVIa) or (XVIb) wherein R$_1$ is as set forth in formula (Ia) or (Ib) under groups (a), (b), (c) or it is a group of formula (IIa) with X as a carbon atom or of formula (IIb), and R, Y, R$^c$ and n are as above defined;

i.4) with a compound of formula (XX)

R$_1$—COZ  (XX)

wherein R$_1$ is a group of formula (IId) and Z is a chlorine or bromine atom, so as to obtain the a compound of formula (XVIa) or (XVIb) wherein R is as defined above and R$_1$ is a group of formula (IId); and j) reacting the compound of formula (XVIa) or (XVIb) prepared according to any one of steps from (i.1) to (i.4) under basic conditions, so as to obtain the corresponding derivative of formula (Ia) or (Ib) wherein R and R$_1$ are as above defined; and, optionally, k) converting them into other compounds of formula (Ia) or (Ib), respectively, and/or into pharmaceutically acceptable salts thereof.

The above process is an analogy process which can be carried out according to methods well known in the art.

From all of the above, it is clear to the person skilled in the art that if a compound of formula (Ia) or (Ib), prepared according to the above process, is obtained as a mixture of isomers, their separation into the single isomers of formula (Ia) or (Ib), carried out according to conventional techniques, is still within the scope of the present invention.

Likewise, the conversion into the free compound (Ia) or (Ib) of a corresponding salt thereof, according to well-known methods, is still within the scope of the invention. According to step (a) of the process, a compound of formula (IIIa) or (IIIb) is reacted with acrylonitrile in the presence of a suitable base, for instance sodium hydroxide. The reaction is preferably carried out in water at a temperature ranging from about −10° C. to room temperature.

According to step (b) of the process, the amino group of the compound of formula (IVa) or (IVb) is protected according to conventional methods, for instance with tert-butoxycarbonyl anhydride (Boc$_2$O) and in the presence of a suitable solvent such as acetonitrile or dichloromethane, so as to get the corresponding derivative of formula (Va) or (Vb) wherein the amino protecting group Q just represents tert-butoxycarbonyl (boc).

According to step (c) of the process, the carboxy group of the compound of formula (Va) or (Vb) is converted into the corresponding alkyl ester derivative, for instance by operating in the presence of a suitable alkyl halide, for instance methyl iodide.

The reaction is carried out in the presence of a suitable solvent such as dimethylformamide and under basic conditions, for instance by using sodium or potassium hydrogencarbonate.

According to step (d) of the process, the compound of formula (VIa) or (VIb) is converted into the corresponding cyclic derivative of formula (VIIa) or (VIIb) through reaction with sodium hydride. The reaction is carried out in the presence of a suitable solvent such as dioxane or tetrahydrofuran at refluxing temperature.

According to step (e) of the process, the compound of formula (VIIa) or (VIIb) is reacted with hydrazine hydrate, preferably with an excess of hydrazine monohydrated, for instance up to 10 equivalents, in the presence of a suitable solvent such as halogenated hydrocarbons, lower alcohols or admixtures thereof. The reaction is preferably carried out in the presence of ethanol, by adding hydrazine to a solution of the compound of formula (VIIa) or (VIIb) and under stirring for a suitable time, for instance about 48 hours, at the temperature ranging from about 20° C. to about 70° C. Preferably, the above reaction is carried out also in the presence of glacial acetic acid.

According to step (f) of the process, the compound of formula (VIIIa) or (VIIIb) is reacted with ethyl chloroformate so as to get the corresponding derivative of formula (IXa) or (IXb). The reaction is carried out according to well-known operative conditions, in the presence of a suitable base, for instance diisopropylethylamine, and of a suitable solvent such as tetrahydrofuran.

Clearly, the ethoxycarbonyl group may be bound to any one of the pyrazole nitrogen atoms of both compounds of formula (VIIIa) and (VIIIb) so as to give rise to the following regioisomers of formula (IXa) or (IXb)

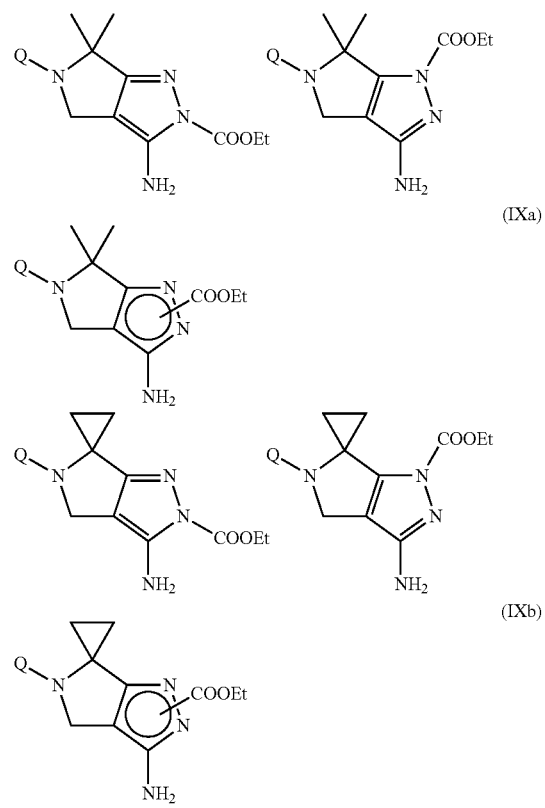

In this respect, each couple of regioisomers of formula (IXa) or (IXb) may be conveniently separated according to well-known methods, for instance under chromatographic conditions, and each regioisomer so isolated subsequently worked out. In the alternative, the mixture of regioisomers can be treated as such in the subsequent steps of the process, without providing any separation.

In fact, as the ethoxycarbonyl group leading to two distinct regioisomers is finally removed at the end of the process, it is clear to the skilled person that both the above pathways can be carried out for preparing the compounds of formula (Ia) or (Ib) of the invention.

Preferably, however, the process is carried out by first separating and isolating the regioisomers of formula (IXa) or (IXb) from their mixture, as reported in the working examples, and by subsequently reacting them to the desired compounds.

According to step (g.1) of the process, the compound of formula (IXa) or (IXb) is reacted with a suitable derivative of formula (X) wherein Z represents a halogen atom, preferably chlorine or bromine.

Typically, the compound of formula (IXa) or (IXb) is dissolved in a suitable solvent such as dichloromethane, dimethylformamide, tetrahydrofuran, dioxane or the like, and a suitable base such as triethylamine, diisopropylethylamine, sodium carbonate or the like is added. The compound of formula (X) is then added and the mixture stirred for a time of about 2 to about 15 hours, at a temperature ranging from about 20° C. to about 80° C.

A suitable catalyst such as dimethylamino-pyridine may be optionally used. According to step (g.2) of the process, the compound of formula (IXa) or (IXb) is reacted with an isocyanate derivative of formula (XII), by operating substantially as set forth in step (g.1) of the process, except that the base may not be required.

According to step (g.3) of the process, the compound of formula (IXa) or (IXb) is reacted with an amine of formula (XIII) in the presence of triphosgene or of a suitable chloroformate, for instance 4-nitrophenyl chloroformate, so as to get the corresponding ureido derivative. The reaction is carried out in tetrahydrofuran (THF) or in a suitable halogenated hydrocarbon, preferably dichloromethane (DCM), and in the presence of a suitable amine such as diisopropylethylamine or triethylamine at a temperature ranging from about −70° C. to room temperature.

According to step (h) of the process, the protected amino group in formula (XIa) or (XIb) is deprotected under well-known operative conditions, for instance under acidic conditions in the presence of trifluoroacetic or hydrochloric acid.

The compound of formula (XIa) or (XIb) is thus suspended in a suitable solvent such as dichloromethane or dioxane, and treated with a concentrated solution of the selected acid. Alternatively, commercially available solutions of gaseous hydrogen chloride dissolved in dioxane (4 M HCl) may be advantageously employed. The mixture is then stirred for a time of about 2 hours to about 15 hours at a temperature ranging from about 20° C. to about 40° C.

According to any one of steps (i.1), (i.2), (i.3) or (i.4) of the process, the compound of formula (XIVa) or (XIVb) is further reacted with a suitable derivative so as to obtain the corresponding carboxamido, ureido or carbamate derivative of formula (XVIa) or (XVIb).

Step (i.1) is carried out with an acyl halide, preferably chloride, of formula (XV) in a suitable solvent such as dichloromethane and under basic conditions, for instance in the presence of a suitable amine such as diisopropylethylamine.

The reaction allows to obtain carboxamido derivatives of formula (XVIa) or (XVIb) wherein $R_1$ is as defined in formula (I) under groups from (a) to (c), (IIa) with X as a carbon atom and (IIb); from the above, it is clear to the skilled person that the atom of the $R_1$ group which is directly linked to the carbonyl moiety of formula (XVIa) or (XVIb) is a carbon atom.

Step (i.2) is carried out with a heterocyclic derivative of formula (XVII) or of an amine of formula (XVIII), in the presence of triphosgene, substantially as described under step (g.3) of the process.

In this respect, step (i.2) allows to obtain ureido derivatives of formula (XVIa) or (XVIb) wherein $R_1$ is a group of formula (IIa) with X as a nitrogen atom or of formula (IIc) and wherein Y, $R^c$, n, $R^d$ and $R'^d$ are as above defined.

Likewise, the condensation of step (i.3) is carried out with a carboxylic acid derivative of formula (XIX), in the presence of a suitable condensing agent such as, for instance, dicyclohexylcarbodiimide (DCC), 1-ethyl-3-(3'-dimethylaminopropyl)carbodiimide (EDC) or O-benzotriazolyl tetramethylisouronium tetrafluoroborate (TBTU), and by operating according to well-known methods for preparing carboxamido derivatives.

According to step (i.4) of the process, the compound of formula (XIVa) or (XIVb) is reacted with a suitable derivative of formula (XX) wherein $R_1$ is a group of formula (IId) and $R^e$ is as set forth in formula (Ia) or (Ib), so as to obtain the corresponding carbamate derivatives of formula (XVIa) or (XVIb).

In this respect, the compound of formula (XIVa) or (XIVb) is dissolved in a suitable solvent such as dichloromethane, dimethylformamide, tetrahydrofuran, dioxane or the like, and a suitable base such as triethylamine, diisopropylethylamine, sodium carbonate or the like is added therein. The compound of general formula (XX) is then added and the mixture stirred for a time of about 2 hours to about 15 hours, at a temperature ranging from about 20° C. to about 80° C. According to a preferred embodiment, a suitable catalyst such as dimethylamino pyridine may be optionally used.

According to step (j) of the process, the compound of formula (XVIa) or (XVIb) being obtained in any one of steps from (i.1) to (i.4) is reacted with a suitable base, for instance triethylamine, and in the presence of a suitable solvent such as methanol or ethanol so as to obtain the desired compound of formula (Ia) or (Ib).

Finally, as per step (k) of the process, these latter compounds (Ia) or (Ib) may be optionally converted into pharmaceutically acceptable salts as formerly reported and by working according to conventional methods or, alternatively, may converted into additional compounds of formula (Ia) or (Ib).

Just as a non limiting example, compounds of formula (Ia) or (Ib) bearing a carboxyester function may be converted into a variety of derivatives according to methods well known in the art to convert carboxyester groups into carboxamides, N-substituted carboxamides, N,N-disubstituted carboxamides, carboxylic acids, and the like.

The operative conditions are those widely known in the art and may comprise, for instance in the conversion of a carboxyester group into a carboxamide group, the reaction with ammonia or ammonium hydroxide in the presence of a suitable solvent such as a lower alcohol, dimethylformamide or mixtures thereof; preferably the reaction is carried out with ammonium hydroxide in a methanol/dimethylformamide mixture, at a temperature ranging from about 50° C. to about 100° C.

Analogous operative conditions apply in the preparation of N-substituted or N,N-disubstituted carboxamides wherein a suitable primary or secondary amine is used in place of ammonia or ammonium hydroxide.

Likewise, carboxyester groups may be converted into carboxylic acid derivatives through basic or acidic hydrolysis conditions, widely known in the art.

As an additional example, compounds of formula (Ia) or (Ib) bearing an amino function may be easily converted into the corresponding carboxamido or ureido derivatives.

From all of the above it is clear to the skilled person that according to step (k) of the process, any compound of formula (Ia) or (Ib) bearing a functional group which can be further derivitized to another functional group, by working according to methods well known in the art thus leading to other compounds of formula (Ia) or (Ib), has to be intended as comprised within the scope of the present invention.

According to any variant of the process for preparing the compounds of formula (I), the starting material and any other reactant is known or easily prepared according to known methods.

As an example, whilst the starting materials of formula (IIIa) or (IIIb) are commercially available, the compounds of formula (X), (XII), (XIII), (XV), (XVII), (XVIII), (XIX) and (XX) are known or can be easily prepared according to known methods.

The intermediate compounds of formula (VIIa) or (VIIb) of the process

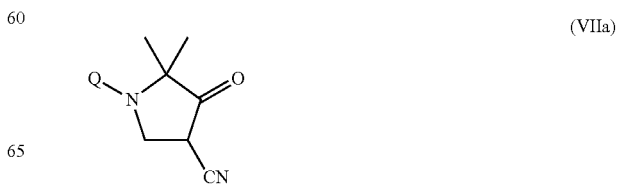

(VIIa)

-continued

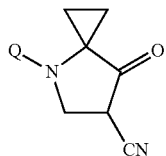

(VIIb)

wherein Q represents a suitable nitrogen protecting group, for instance tert-butoxycarbonyl (boc), are novel and, hence, represent a further object of the invention. As it will be readily appreciated, if the compounds of formula (I) prepared according to the process described above are obtained as an admixture of isomers, their separation into the single isomers of formula (I), according to conventional techniques, is within the scope of the present invention. Conventional techniques for racemate resolution include, for instance, partitioned crystallization of diastereoisomeric salt derivatives or preparative chiral HPLC.

In addition, it is clear from the above that a given compound of formula (Ia) or (Ib) may be prepared either by starting from the mixture of the regioisomers of formula (IXa) or (IXb) or, alternatively, from each one of the two regioisomers themselves. When preparing the compounds of formula (I) according to any one of the aforementioned process variants, optional functional groups within the starting materials or the intermediates thereof and which could give rise to unwanted side reactions, need to be properly protected according to conventional techniques. Likewise, the conversion of these latter into the free deprotected compounds may be carried out according to known procedures.

In addition, the compounds of formula (I) of the invention may be also prepared according to combinatorial chemistry techniques widely known in the art, by accomplishing the aforementioned reactions between the several intermediates in a serial manner and by working under solid-phase-synthesis (SPS) conditions.

As an example, the compounds of formula (XIa) or (XIb) which are prepared according to any one of steps (g.1), (g.2) or (g.3) can be supported onto a suitable polymeric resin. More particularly, the ethoxycarbonyl group in formula (XIa) or (XIb) may be removed under basic conditions, for instance in the presence of triethylamine or diisopropylamine, and the resultant compound anchored to the above supporting resin, through the pyrazole nitrogen atom itself

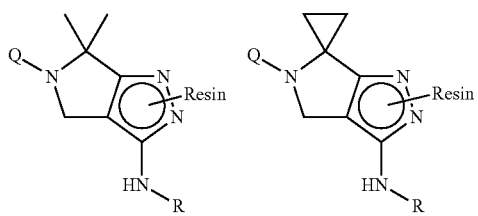

The supported intermediate thus obtained may be then reacted according to step (h) and any one of steps (i.1), (i.2), (i.3) or (i.4) of the process, so as to obtain the corresponding compound of formula (Ia) or (Ib) of the invention still supported on the polymeric resin. Subsequent resin cleavage, for instance under basic or acidic conditions according to known methods, allows to obtain the desired compounds of formula (Ia) or (Ib).

Clearly, by performing the above reactions of the process in a serial manner, that is by following a combinatorial approach for instance as set forth above, several compounds of formula (Ia) and (Ib) may be thus prepared and collected.

Therefore, it is a further object of the present invention a library of two or more compounds of formula (Ia)

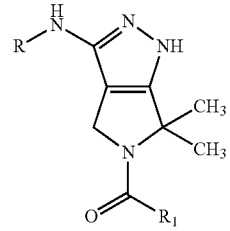

(Ia)

wherein
R is a group —$COR^a$, —$CONHR^a$ or —$CONR^aR^b$ wherein $R^a$ and $R^b$ are, each independently, hydrogen or an optionally substituted group selected from straight or branched $C_1$-$C_6$ alkyl, $C_3$-$C_6$ cycloalkyl, aryl, arylalkyl, heterocyclyl or heterocyclylalkyl or; together with the nitrogen atom to which they are bonded, $R^a$ and $R^b$ may form an optionally substituted 5 or 6 membered heterocycle optionally containing one additional heteroatom or heteroatomic group selected among N, NH, O or S;

$R_1$ is selected from the group consisting of:
a) straight or branched $C_3$-$C_4$ alkyl;
b) cycloalkyl, cycloalkyl-alkyl or alkyl-cycloalkyl wherein the cycloalkyl moiety comprises any $C_3$-$C_6$ cycloalkyl group and wherein the alkyl moiety comprises any straight or branched $C_1$-$C_4$ alkyl group:
c) 3-methylthienyl-2-yl; 2-thienyl; phenyl; 2,6-difluorophenyl; 4-(aminosulfonyl)phenyl; 4-(dimethylaminomethyl)phenyl; 4-(4-methylpiperazinyl)methyl-phenyl;
d) a group of formula (IIa) or (IIb):

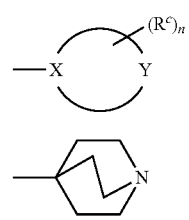

(IIa)

(IIb)

wherein, in formula (IIa), the cycle represents a 5 to 7 membered heterocyclic ring wherein X, directly linked to the rest of the molecule, represents a carbon or nitrogen atom; Y is a carbon, nitrogen, oxygen or sulfur atom or it is an NH group, provided that at least one of X and Y is other than a carbon atom; $R^c$ is, independently from each other and in any one of the free positions of the heterocyclic ring of formula (IIa), a halogen atom or hydroxy group or it is an optionally substituted group selected from straight or branched $C_1$-$C_6$ alkyl, $C_3$-$C_6$ cycloalkyl, aryl, arylalkyl, heterocyclyl, heterocyclylalkyl, amino, aminocarbonyl, carboxy, oxo (═O), alkoxycarbonyl, alkylcarbonyl or arylcarbonyl; and n is 0 or an integer from 1 to 4;

e) a group of formula (IIc) or (IId):

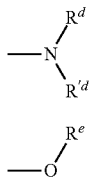

wherein $R^d$, $R'^d$ and $R^e$ represent, the same or different and independently from each other, a hydrogen atom or a straight or branched $C_1$-$C_6$ alkyl optionally substituted by one or more groups selected from hydroxy (—OH), aminocarbonyl (—$CONH_2$) or methylaminocarbonyl (—$CONHCH_3$);

provided that in formula (Ia), when $R_1$ is a group of formula (IIc) and one of $R^d$ or $R'^d$ is a hydrogen atom whilst the other of $R^d$ or $R'^d$ is ethyl or n-butyl, then R is other than —$COR^a$ with $R^a$ as 3-bromophenyl, benzyl, 4-tert-butylphenyl, 4-tert-butylphenylmethyl, 4-fluorophenylmethyl, cyclopropyl or 2-naphthylmethyl;

or a pharmaceutically acceptable salt thereof.

Likewise, it is a further object of the present invention a library of two or more compounds of formula (Ib)

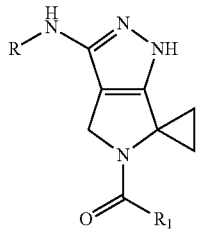

wherein

R is a group —$COR^a$, —$CONHR^a$ or —$CONR^aR^b$ wherein $R^a$ and $R^b$ are, each independently, hydrogen or an optionally substituted group selected from straight or branched $C_1$-$C_6$ alkyl, $C_3$-$C_6$ cycloalkyl, aryl, arylalkyl, heterocyclyl or heterocyclylalkyl or; together with the nitrogen atom to which they are bonded, $R^a$ and $R^b$ may form an optionally substituted 5 or 6 membered heterocycle optionally containing one additional heteroatom or heteroatomic group selected among N, NH, O or S;

$R_1$ is selected from the group consisting of:

a) straight or branched $C_3$-$C_4$ alkyl;

b) cycloalkyl, cycloalkyl-alkyl or alkyl-cycloalkyl wherein the cycloalkyl moiety comprises any $C_3$-$C_6$ cycloalkyl group and wherein the alkyl moiety comprises any straight or branched $C_1$-$C_4$ alkyl group:

c) 3-methylthienyl-2-yl; 2-thienyl; phenyl; 2,6-difluorophenyl; 4-(aminosulfonyl)phenyl; 4-(dimethylaminomethyl)phenyl; 4-(4-methylpiperazinyl)methyl-phenyl;

d) a group of formula (IIa) or (IIb):

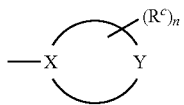

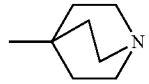

wherein, in formula (IIa), the cycle represents a 5 to 7 membered heterocyclic ring wherein X, directly linked to the rest of the molecule, represents a carbon or nitrogen atom; Y is a carbon, nitrogen, oxygen or sulfur atom or it is an NH group, provided that at least one of X and Y is other than a carbon atom; $R^c$ is, independently from each other and in any one of the free positions of the heterocyclic ring of formula (IIa), a halogen atom or hydroxy group or it is an optionally substituted group selected from straight or branched $C_1$-$C_6$ alkyl, $C_3$-$C_6$ cycloalkyl, aryl, arylalkyl, heterocyclyl, heterocyclylalkyl, amino, aminocarbonyl, carboxy, oxo (═O), alkoxycarbonyl, alkylcarbonyl or arylcarbonyl; and n is 0 or an integer from 1 to 4;

e) a group of formula (IIc) or (IId):

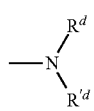

wherein $R^d$, $R'^d$ and $R^e$ represent, the same or different and independently from each other, a hydrogen atom or a straight or branched $C_1$-$C_6$ alkyl optionally substituted by one or more groups selected from hydroxy (—OH), aminocarbonyl (—$CONH_2$) or methylaminocarbonyl (—$CONHCH_3$);

or a pharmaceutically acceptable salt thereof.

For a general reference to the above libraries of compounds of formula (I) see the experimental section.

From all of the above, it is clear to the skilled person that once a library of pyrrolo-pyrazole derivatives is thus prepared, for instance consisting of a few hundreds or even a few thousands of compounds of formula (Ia) or (Ib), the said library can be very advantageously used for screening towards given kinases, as formerly reported. See, for a general reference to libraries of compounds and uses thereof as tools for screening biological activities, J. Med. Chem. 1999, 42, 2373-2382; and Bioorg. Med. Chem. Lett. 10 (2000), 223-226.

Pharmacology

The compounds of formula (I) are active as protein kinase inhibitors and are therefore useful, for instance, to restrict the unregulated proliferation of tumor cells. In therapy, they may be used in the treatment of various tumors, such as those formerly reported, as well as in the treatment of other cell proliferative disorders such as psoriasis, vascular smooth cell proliferation associated with atherosclerosis and post-surgical stenosis and restenosis and in the treatment of Alzheimer's disease.

The inhibiting activity of putative Cdk/Cyclin inhibitors and the potency of selected compounds was determined through a method of assay based on the use of the SPA technology (Amersham Pharmacia Biotech).

The assay consists of the transfer of radioactivity labelled phosphate moiety by the kinase to a biotinylated substrate. The resulting 33P-labelled biotinylated product is allowed to bind to streptavidin-coated SPA beads (biotin capacity 130 pmol/mg), and light emitted was measured in a scintillation counter.

Inhibition Assay of Cdk2/Cyclin A Activity

Kinase reaction: 4 µM in house biotinylated histone H1 (Sigma #H-5505) substrate, 10 µM ATP (0.1 microCi $P^{33}\gamma$-ATP), 4.2 ng Cdk2/Cyclin A complex, inhibitor in a final volume of 30 µl buffer (TRIS HCl 10 mM pH 7.5, MgCl$_2$ 10 mM, DTT 7.5 mM+0.2 mg/ml BSA) were added to each well of a 96 U bottom. After 30 min at r.t. incubation, reaction was stopped by 100 µl PBS+32 mM EDTA+0.1% Triton X-100+ 500 µM ATP, containing 1 mg SPA beads. Then a volume of 110 µl is transferred to Optiplate.

After 20 min. incubation for substrate capture, 100 µl 5M CsCl were added to allow statification of beads to the top of the plate and let stand 4 hours before radioactivity counting in the Top-Count instrument.

IC50 determination: inhibitors were tested at different concentrations ranging from 0.0015 to 10 µM. Experimental data were analyzed by the computer program GraphPad Prizm using the four parameter logistic equation:

$$y = \text{bottom} + (\text{top-bottom})/(1+10^{((\log IC50-x)*\text{slope})})$$

where x is the logarithm of the inhibitor concentration, y is the response; y starts at bottom and goes to top with a sigmoid shape.

Ki Calculation:

Experimental method: Reaction was carried out in buffer (10 mM Tris, pH 7.5, 10 mM MgCl$_2$, 0.2 mg/ml BSA, 7.5 mM DTT) containing 3.7 nM enzyme, histone and ATP (constant ratio of cold/labeled ATP 1/3000). Reaction was stopped with EDTA and the substrate captured on phosphomembrane (Multiscreen 96 well plates from Millipore). After extensive washing, the multiscreen plates are read on a top counter. Control (time zero) for each ATP and histone concentrations was measured.

Experimental design: Reaction velocities are measured at different four ATP, substrate (histone) and inhibitor concentrations. An 80-point concentration matrix was designed around the respective ATP and substrate Km values, and the inhibitor IC50 values (0.3, 1, 3, 9 fold the Km or IC50 values). A preliminary time course experiment in the absence of inhibitor and at the different ATP and substrate concentrations allow the selection of a single endpoint time (10 min) in the linear range of the reaction for the Ki determination experiment.

Kinetic parameter estimates: Kinetic parameters were estimated by simultaneous nonlinear least-square regression using [Eq. 1](competitive inhibitor respect to ATP, random mechanism) using the complete data set (80 points):

$$v = \frac{Vm \cdot A \cdot B}{\alpha \cdot Ka \cdot Kb + \alpha \cdot Ka \cdot B + \alpha \cdot Kb \cdot A + A \cdot B + \alpha \cdot \frac{Ka}{Ki} \cdot I \cdot \left(Kb + \frac{B}{\beta}\right)}$$ [Eq. 1]

where A=[ATP], B=[Substrate], I=[inhibitor], Vm=maximum velocity, Ka, Kb, Ki the dissociation constants of ATP, substrate and inhibitor respectively. $\alpha$ and $\beta$ the cooperativity factor between substrate and ATP binding and substrate and inhibitor binding respectively.

In addition the selected compounds have been characterized on a panel of ser/threo kinases strictly related to cell cycle (Cdk2/Cyclin E, Cdk1/cyclin B1, Cdk5/p25, Cdk4/Cyclin D1), and also for specificity on MAPK, PKA, EGFR, IGF1-R, Aurora-2 and Akt.

Inhibition Assay of Cdk2/Cyclin E Activity

Kinase reaction: 10 µM in house biotinylated histone H1 (Sigma #H-5505) substrate, 30 µM ATP (0.3 microCi $P^{33}\gamma$-ATP), 4 ng GST-Cdk2/Cyclin E complex, inhibitor in a final volume of 30 µl buffer (TRIS HCl 10 mM pH 7.5, MgCl$_2$ 10 mM, DTT 7.5 mM+0.2 mg/ml BSA) were added to each well of a 96 U bottom. After 60 min at r.t. incubation, reaction was stopped by 100 µl PBS+32 mM EDTA+0.1% Triton X-100+ 500 µM ATP, containing 1 mg SPA beads. Then a volume of 110 µl is transferred to Optiplate.

After 20 min. incubation for substrate capture, 100 µl 5M CsCl were added to allow statification of beads to the top of the plate and let stand 4 hours before radioactivity counting in the Top-Count instrument IC50 determination: see above Inhibition Assay of Cdk1/Cyclin B1 Activity Kinase reaction: 4 M in house biotinylated histone H1 (Sigma #H-5505) substrate, 20 M ATP (0.2 microCi $P^{33}\gamma$-ATP), 3 ng Cdk1/Cyclin B complex, inhibitor in a final volume of 301 buffer (TRIS HCl 10 mM pH 7.5, MgCl$_2$ 10 mM, DTT 7.5 mM+0.2 mg/ml BSA) were added to each well of a 96 U bottom. After 20 min at r.t. incubation, reaction was stopped by 100 µl PBS+32 mM EDTA+0.1% Triton X-100+ 500 M ATP, containing 1 mg SPA beads. Then a volume of 110 µl is transferred to Optiplate.

After 20 min. incubation for substrate capture, 100 µl 5M CsCl were added to allow statification of beads to the top of the Optiplate and let stand 4 hours before radioactivity counting in the Top-Count instrument.

IC50 determination: see above

Inhibition Assay of Cdk5/p25 Activity

The inhibition assay of Cdk5/p25 activity was performed according to the following protocol.

Kinase reaction: 10 µM biotinylated histone H1 (Sigma #H-5505) substrate, 30 µM ATP (0.3 microCi $P^{33}\gamma$-ATP), 15 ng CDK5/p25 complex, inhibitor in a final volume of 30 µl buffer (TRIS HCl 10 mM pH 7.5, MgCl$_2$ 10 mM, DTT 7.5 mM+0.2 mg/ml BSA) were added to each well of a 96 U bottom. After 30 min at r.t. incubation, reaction was stopped by 100 µl PBS+32 mM EDTA+0.1% Triton X-100+500 µM ATP, containing 1 mg SPA beads. Then a volume of 110 µl is transferred to Optiplate. After 20 min. incubation for substrate capture, 100 µl 5M CsCl were added to allow statification of beads to the top of the plate and let stand 4 hours before radioactivity counting in the Top-Count instrument.

IC50 determination: see above

Inhibition Assay of Cdk4/Cyclin D1 Activity

Kinase reaction: 0.4 uM µM mouse GST-Rb (769-921) (#sc-4112 from Santa Cruz) substrate, 10 µM ATP (0.5 µCi $P^{33}\gamma$-ATP), 100 ng of baculovirus expressed GST-Cdk4/Cyclin D1, suitable concentrations of inhibitor in a final volume of 501 buffer (TRIS HCl 10 mM pH 7.5, MgCl$_2$ 10 mM, 7.5 mM DTT+0.2 mg/ml BSA) were added to each well of a 96 U bottom well plate. After 40 min at 37° C. incubation, reaction was stopped by 20 µl EDTA 120 mM.

Capture: 60 µl were transferred from each well to MultiScreen plate, to allow substrate binding to phosphocellulose filter. Plates were then washed 3 times with 150 µl/well PBS $Ca^{++}/Mg^{++}$ free and filtered by MultiScreen filtration system.

Detection: filters were allowed to dry at 37° C., then 100 µl/well scintillant were added and $^{33}$P labeled Rb fragment was detected by radioactivity counting in the Top-Count instrument.

IC50 determination: see above

Inhibition Assay of MAPK Activity

Kinase reaction: 10 µM in house biotinylated MBP (Sigma #M-1891) substrate, 15 M ATP (0.15 microCi P$^{33}$γ-ATP), 30 ng GST-MAPK (Upstate Biotechnology #14-173), inhibitor in a final volume of 30 µl buffer (TRIS HCl 10 mM pH 7.5, MgCl$_2$ 10 mM, DTT 7.5 mM+0.2 mg/ml BSA) were added to each well of a 96 U bottom. After 30 min at r.t. incubation, reaction was stopped by 100 µl PBS+32 mM EDTA+0.1% Triton X-100+500 µM ATP, containing 1 mg SPA beads. Then a volume of 110 µl is transferred to Optiplate.

After 20 min. incubation for substrate capture, 100 µl 5M CsCl were added to allow statification of beads to the top of the Optiplate and let stand 4 hours before radioactivity counting in the Top-Count instrument.

IC50 determination: see above

Inhibition Assay of PKA Activity

Kinase reaction: 10 µM in house biotinylated histone H1 (Sigma #H-5505) substrate, 10 µM ATP (0.2 microM P$^{33}$γ-ATP), 0.45 U PKA (Sigma #2645), inhibitor in a final volume of 30 µl buffer (TRIS HCl 10 mM pH 7.5, MgCl$_2$ 10 mM, DTT 7.5 mM+0.2 mg/ml BSA) were added to each well of a 96 U bottom. After 90 min at r.t. incubation, reaction was stopped by 100 µl PBS+32 mM EDTA+0.1% Triton X-100+ 500 µM ATP, containing 1 mg SPA beads. Then a volume of 110 µl is transferred to Optiplate.

After 20 min. incubation for substrate capture, 100 µl 5M CsCl were added to allow statification of beads to the top of the Optiplate and let stand 4 hours before radioactivity counting in the Top-Count instrument.

IC50 determination: see above

Inhibition Assay of EGFR Activity

Kinase reaction: 10 µM in house biotinylated MBP (Sigma #M-1891) substrate, 2 µM ATP (0.04 microCi P$^{33}$γ-ATP), 36 ng insect cell expressed GST-EGFR, inhibitor in a final volume of 30 µl buffer (Hepes 50 mM pH 7.5, MgCl$_2$ 3 mM, MnCl$_2$ 3 mM, DTT 1 mM, NaVO$_3$ 3 µM+0.2 mg/ml BSA) were added to each well of a 96 U bottom. After 20 min at r.t. incubation, reaction was stopped by 100 µl PBS+32 mM EDTA+0.1% Triton X-100+500 µM ATP, containing 1 mg SPA beads. Then a volume of 110 µl is transferred to Optiplate.

After 20 min. incubation for substrate capture, 100 µl 5M CsCl were added to allow statification of beads to the top of the Optiplate and let stand 4 hours before radioactivity counting in the Top-Count instrument.

IC50 determination: see above

Inhibition Assay of IGF1-R Activity

The inhibition assay of IGF1-R activity was performed according to the following protocol.

Kinase reaction: 10 µM biotinylated MBP (Sigma cat. #M-1891) substrate, 0-20 µM inhibitor, 6 µM ATP, 1 microCi $^{33}$P-ATP, and 22.5 ng GST-IGF1-R (pre-incubated for 30 min at room temperature with cold 60 µM cold ATP) in a final volume of 30 µl buffer (50 mM HEPES pH 7.9, 3 mM MnCl$_2$, 1 mM DTT, 3 µM NaVO$_3$) were added to each well of a 96 U bottom well plate. After incubation for 35 min at room temperature, the reaction was stopped by addition of 100 µl PBS buffer containing 32 mM EDTA, 500 µM cold ATP, 0.1% Triton X100 and 10 mg/ml streptavidin coated SPA beads. After 20 min incubation, 110 µL of suspension were withdrawn and transferred into 96-well OPTIPLATEs containing 100 µl of 5M CsCl. After 4 hours, the plates were read for 2 min in a Packard TOP-Count radioactivity reader.

Inhibition Assay of Aurora-2 Activity

Kinase reaction: 8 µM biotinylated peptide (4 repeats of LRRWSLG), 10 µM ATP (0.5 uCi P$^{33}$γ-ATP), 15 ng Aurora2, inhibitor in a final volume of 30 µl buffer (HEPES 50 mM pH 7.0, MgCl$_2$ 10 mM, 1 mM DTT, 0.2 mg/ml BSA, 3 µM orthovanadate) were added to each well of a 96 U bottom well plate. After 30 minutes at room temperature incubation, reaction was stopped and biotinylated peptide captured by adding 100 µl of bead suspension.

Stratification: 100 µl of CsCl2 5 M were added to each well and let stand 4 hour before radioactivity was counted in the Top-Count instrument.

IC50 determination: see above

Inhibition Assay of Cdc7/dbf4 Activity

The inhibition assay of Cdc7/dbf4 activity was performed according to the following protocol.

The Biotin-MCM2 substrate is trans-phosphorylated by the Cdc7/Dbf4 complex in the presence of ATP traced with γ$^{33}$-ATP. The phosphorylated Biotin-MCM2 substrate is then captured by Streptavidin-coated SPA beads and the extent of phosphorylation evaluated by β counting.

The inhibition assay of Cdc7/dbf4 activity was performed in 96 wells plate according to the following protocol.

To each well of the plate were added:
10 µl substrate (biotinylated MCM2, 6 µM final concentration)
10 µl enzyme (Cdc7/Dbf4, 12.5 nM final concentration)
10 µl test compound (12 increasing concentrations in the nM to M range to generate a dose-response curve)
10 µl of a mixture of cold ATP (10 M final concentration) and radioactive ATP (1/2500 molar ratio with cold ATP) was then used to start the reaction which was allowed to take place at 37° C.

Substrate, enzyme and ATP were diluted in 50 mM HEPES pH 7.9 containing 15 mM MgCl$_2$, 2 mM DTT, 3 M NaVO$_3$, 2 mM glycerophosphate and 0.2 mg/ml BSA.

The solvent for test compounds also contained 10% DMSO.

After incubation for 20 minutes, the reaction was stopped by adding to each well 100 µl of PBS pH 7.4 containing 50 mM EDTA, 1 mM cold ATP, 0.1% Triton X100 and 10 mg/ml streptavidin coated SPA beads.

After 15 minutes of incubation at room temperature to allow the biotinylated MCM2-streptavidin SPA beads interaction to occur, beads were trapped in a 96 wells filter plate (Unifilter® GF/B™) using a Packard Cell Harvester (Filtermate), washed with distilled water and then counted using a Top Count (Packard).

Counts were blank-subtracted and then the experimental data (each point in triplicate) were analyzed for IC50 determination using a non-linear regression analysis (Sigma Plot).

Given the above inhibition assays, the compounds of formula (I) of the invention resulted to possess a remarkable cdk inhibitory activity. See, as an example, the following experimental data (IC$_{50}$) of two representative compounds of the invention of formula (Ia) and (Ib) being tested against Cdk2/Cyclin A:

Compound 1: N-[5-(2,2-dimethylpropanoyl)-6,6-dimethyl-1,4,5,6-tetrahydropyrrolo[3,4-c]pyrazol-3-yl]-4-fluorobenzamide (IC$_{50}$ 0.030 µM); and Compound 2: N-[5-(2,2-dimethylpropanoyl)-1,4,5,6-tetrahydropyrrolo[3,4-c]pyrazol-6-spirocyclopropan-3-yl]-4-fluorobenzamide (IC$_{50}$ 0.025 µM). Surprisingly, the said inhibitory activity resulted to be markedly superior that that of a very close compound of the prior art WO 02/12242, herewith referred to as Reference compound (see compound 1143, bottom of page 76; and example 19, compound bridging pages 242-3 of WO 02/12242), used for comparative purposes and tested against Cdk2/Cyclin A, as formerly reported:

Reference Compound: N-[5-acetyl-6,6-dimethyl-4,6-dihydropyrrolo[3,4-c]pyrazol-3-yl]-(3-bromo)benzamide ($IC_{50}$ 1.7 μM)

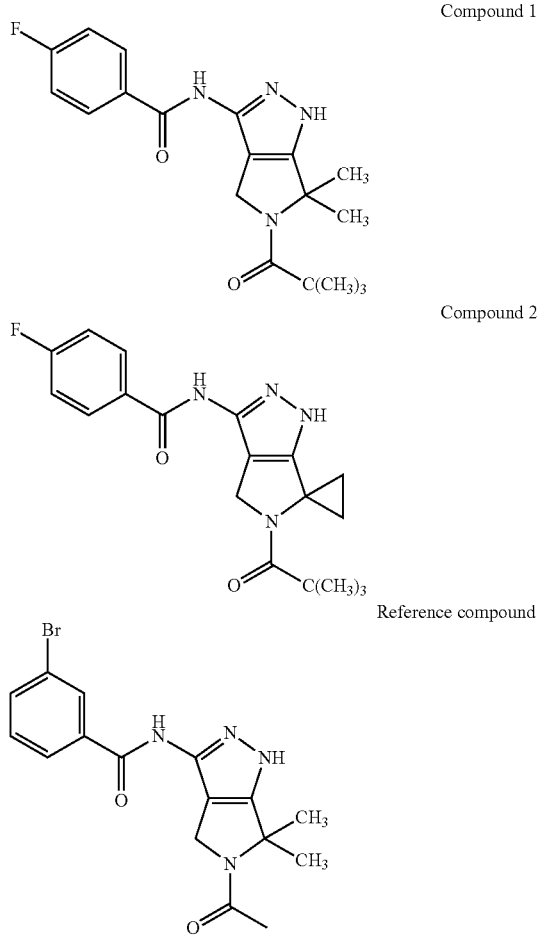

Compound 1

Compound 2

Reference compound

So far, the novel compounds of the invention are unexpectedly endowed with a cdk inhibitory activity significantly higher than that of the structurally closest prior art compounds of WO 02/12242 and are thus particularly advantageous, in therapy, against proliferative disorders associated with an altered cell cycle dependent kinase activity. The compounds of the present invention can be administered either as single agents or, alternatively, in combination with known anticancer treatments such as radiation therapy or chemotherapy regimen in combination with cytostatic or cytotoxic agents, antibiotic-type agents, alkylating agents, antimetabolite agents, hormonal agents, immunological agents, interferon-type agents, cyclooxygenase inhibitors (e.g. COX-2 inhibitors), matrixmetalloprotease inhibitors, telomerase inhibitors, tyrosine kinase inhibitors, anti-growth factor receptor agents, anti-HER agents, anti-EGFR agents, anti-angiogenesis agents (e.g. angiogenesis inhibitors), farnesyl transferase inhibitors, ras-raf signal transduction pathway inhibitors, cell cycle inhibitors, other cdks inhibitors, tubulin binding agents, topoisomerase I inhibitors, topoisomerase II inhibitors, and the like.

If formulated as a fixed dose, such combination products employ the compounds of this invention within the dosage range described below and the other pharmaceutically active agent within the approved dosage range.

Compounds of formula (I) may be used sequentially with known anticancer agents when a combination formulation is inappropriate.

The compounds of formula (I) of the present invention, suitable for administration to a mammal, e.g., to humans, can be administered by the usual routes and the dosage level depends upon the age, weight, conditions of the patient and administration route.

For example, a suitable dosage adopted for oral administration of a compound of formula (I) may range from about 10 to about 500 mg per dose, from 1 to 5 times daily. The compounds of the invention can be administered in a variety of dosage forms, e.g., orally, in the form tablets, capsules, sugar or film coated tablets, liquid solutions or suspensions; rectally in the form suppositories; parenterally, e.g., intramuscularly, or through intravenous and/or intrathecal and/or intraspinal injection or infusion.

The present invention also includes pharmaceutical compositions comprising a compound of formula (I) or a pharmaceutically acceptable salt thereof in association with a pharmaceutically acceptable excipient, which may be a carrier or a diluent.

The pharmaceutical compositions containing the compounds of the invention are usually prepared following conventional methods and are administered in a suitable pharmaceutical form. For example, the solid oral forms may contain, together with the active compound, diluents, e.g., lactose, dextrose saccharose, sucrose, cellulose, corn starch or potato starch; lubricants, e.g., silica, talc, stearic acid, magnesium or calcium stearate, and/or polyethylene glycols; binding agents, e.g., starches, arabic gum, gelatine methylcellulose, carboxymethylcellulose or polyvinyl pyrrolidone; disintegrating agents, e.g., starch, alginic acid, alginates or sodium starch glycolate; effervescing mixtures; dyestuffs; sweeteners; wetting agents such as lecithin, polysorbates, laurylsulphates; and, in general, non-toxic and pharmacologically inactive substances used in pharmaceutical formulations. These pharmaceutical preparations may be manufactured in known manner, for example, by means of mixing, granulating, tabletting, sugar-coating, or film-coating processes.

The liquid dispersions for oral administration may be, e.g., syrups, emulsions and suspensions. As an example, the syrups may contain, as carrier, saccharose or saccharose with glycerine and/or mannitol and sorbitol.

The suspensions and the emulsions may contain, as examples of carriers, natural gum, agar, sodium alginate, pectin, methylcellulose, carboxymethylcellulose, or polyvinyl alcohol. The suspension or solutions for intramuscular injections may contain, together with the active compound, a pharmaceutically acceptable carrier, e.g., sterile water, olive oil, ethyl oleate, glycols, e.g., propylene glycol and, if desired, a suitable amount of lidocaine hydrochloride.

The solutions for intravenous injections or infusions may contain, as a carrier, sterile water or preferably they may be in the form of sterile, aqueous, isotonic, saline solutions or they may contain propylene glycol as a carrier.

The suppositories may contain, together with the active compound, a pharmaceutically acceptable carrier, e.g., cocoa butter, polyethylene glycol, a polyoxyethylene sorbitan fatty acid ester surfactant or lecithin.

With the aim of better illustrating the present invention, without posing any limitation to it, the following examples are now given.

General Methods

Before taking into consideration the synthetic preparation of the specific compounds of formula (I) of the invention, for instance as reported in the following examples, attention should be given to the fact that some compounds are herewith listed and indicated according to their chemical name whilst others, most of them, have been conveniently and unambiguously identified through a coding system, together with their $^1$H-NMR data (see following tables III, IV and V) and HPLC/Mass data (see following table VI).

Each code, in particular, identifies a single specific compound of formula (Ia) or (Ib) and consists of three units A-M-B.

A represents any substituent R [see formula (Ia) or (Ib)] and is attached to the rest of the molecule through the —NH— group; each specific A group is represented and consecutively numbered in the following table I.

Likewise, B represents any substituent $R_1$ [see formula (Ia) or (Ib)] and is attached to the rest of the molecule through the carbonyl (CO) group; each specific B group is represented and consecutively numbered in the following table II.

M refers to the central core of the divalent moiety which is substituted by groups A and B; in particular, M may vary from M1 or M2 as per the formulae below, each identifying the central core of a compound having formula (Ia) or (Ib), respectively:

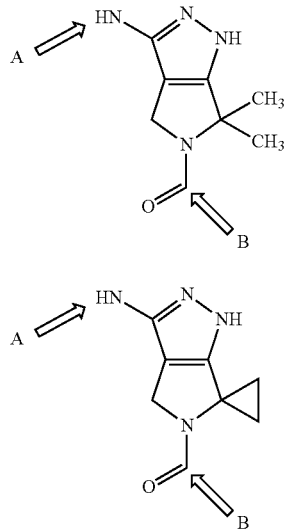

For ease of reference, all of the A and B groups of tables I and II have been identified with the proper chemical formula also indicating the point of attachment with the rest of the molecule M.

Therefore, just as an example, the compound A06-M1-B01 of table III represents the compound of formula (Ia) having the central M1 core, being substituted by the group A06 and by the group B01, in the positions indicated by the arrows; likewise, the compound A04-M2-B08 of table V represents the compound of formula (Ib) having the central M2 core, being substituted by the group A04 and by the group B08, in the positions indicated by the arrows:

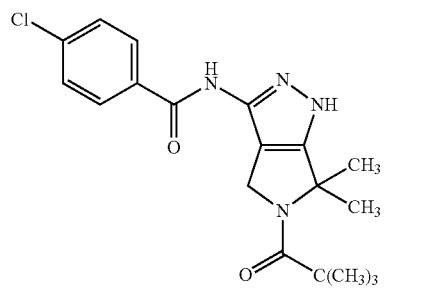

A06-M1-B01

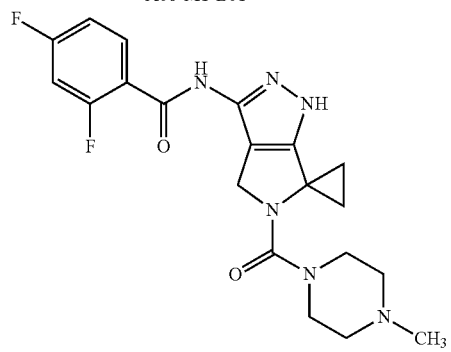

A04-M2-B08

TABLE I

| A01 | 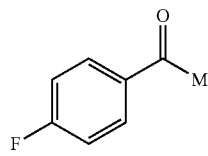 |
| --- | --- |
| A02 | 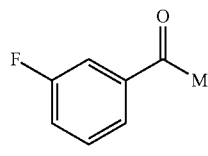 |
| A03 | 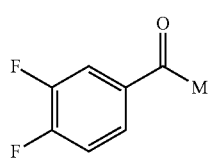 |
| A04 | 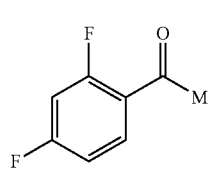 |
| A05 | 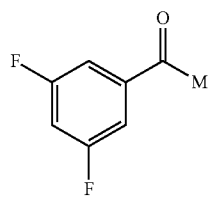 |

TABLE I-continued

| ID | Structure |
|----|-----------|
| A06 | 4-chlorobenzoyl–M |
| A07 | 4-(trifluoromethyl)benzoyl–M |
| A08 | pyridine-3-carbonyl–M |
| A09 | pyridine-4-carbonyl–M |
| A10 | thiophene-2-carbonyl–M |
| A11 | thiophene-3-carbonyl–M |
| A12 | 3-methylbutanoyl–M |
| A13 | cyclobutanecarbonyl–M |
| A14 | cyclopropanecarbonyl–M |
| A15 | pivaloyl (2,2-dimethylpropanoyl)–M |
| A16 | 4-(trifluoromethoxy)benzoyl–M |
| A17 | 3-phenoxybenzoyl–M |
| A18 | 3-(phenylthio)benzoyl–M |
| A19 | furan-2-carbonyl–M |
| A20 | piperidine-4-carbonyl–M |
| A21 | 4-(1H-pyrazol-1-yl)benzoyl–M |
| A22 | naphthalene-1-carbonyl–M |
| A23 | naphthalene-2-carbonyl–M |
| A24 | (2-methylbenzyl)carbamoyl–M |
| A25 | benzylcarbamoyl–M |
| A26 | propylcarbamoyl–M |

TABLE I-continued
| | | |
|---|---|---|
| A27 | 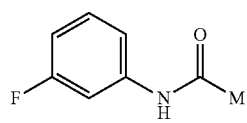 | |
| A28 | 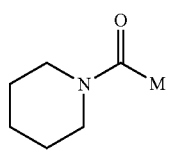 | |
| A29 | 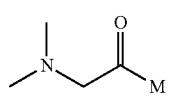 | |
| A30 | 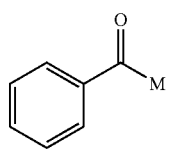 | |
| A31 | 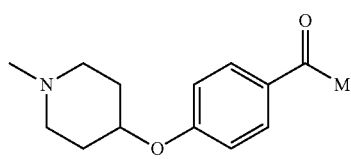 | |
| A32 | 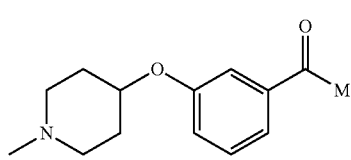 | |
| A33 | 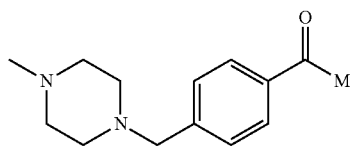 | |
| A34 | 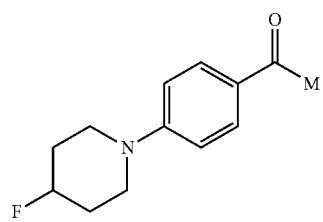 | |
| A35 | 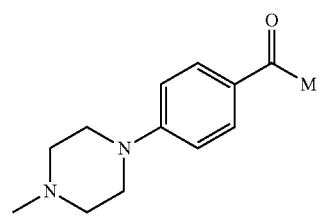 | |
| A36 | 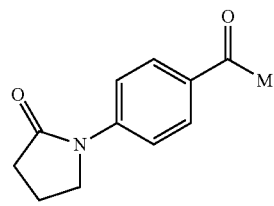 | |
| A37 | 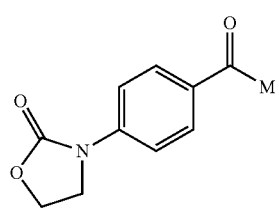 | |
| A38 | 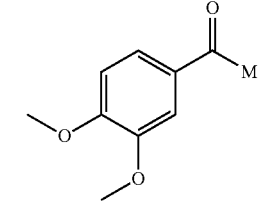 | |
| A39 | 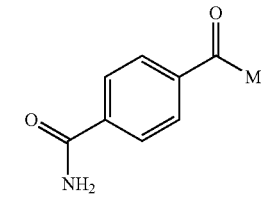 | |
| A40 | 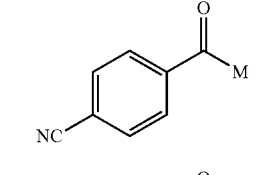 | |
| A41 | 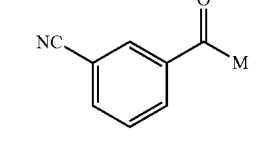 | |
| A42 | 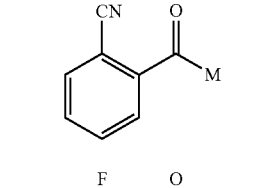 | |
| A43 | 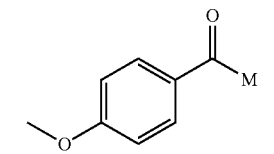 | |
| A44 | 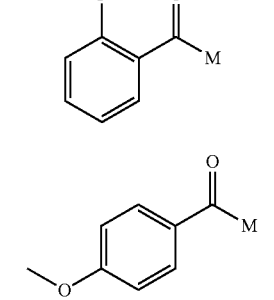 | |

TABLE I-continued
| | |
|---|---|
| A45 | 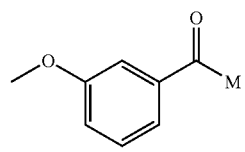 |
| A46 | 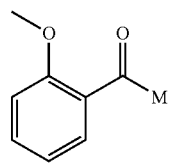 |
| A47 | 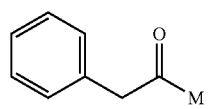 |
| A48 | 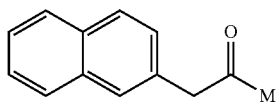 |
| A49 | 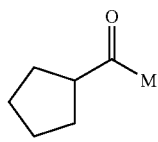 |
| A50 | 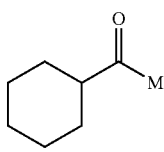 |
| A51 | 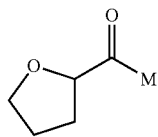 |
| A52 | 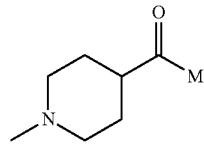 |
| A53 | 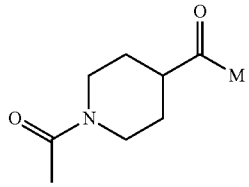 |
| A54 | 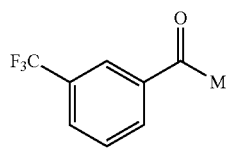 |
| A55 | 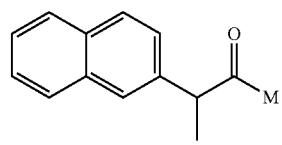 |
TABLE II
| | |
|---|---|
| B01 | 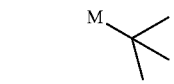 |
| B02 | 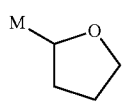 |
| B03 | 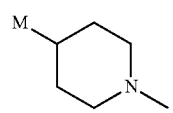 |
| B04 | 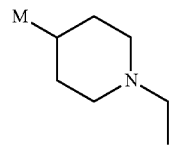 |
| B05 | 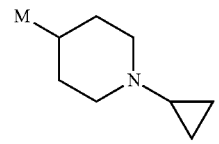 |
| B06 | 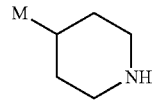 |
| B07 | 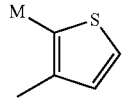 |
| B08 | 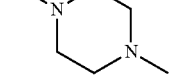 |
| B09 | 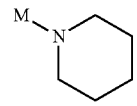 |
| B10 | 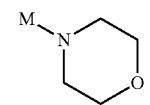 |
| B11 | 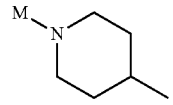 |

TABLE II-continued
| | | | | |
|---|---|---|---|---|
| B12 | 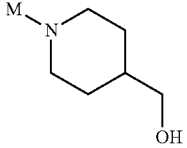 | | B23 | 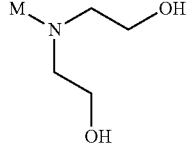 |
| B13 | 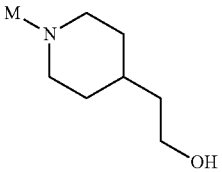 | | B24 | 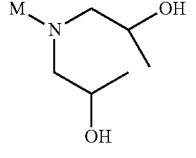 |
| B14 | 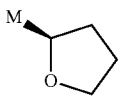 | | B25 | 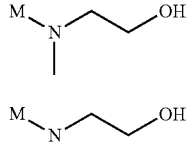 |
| B15 | 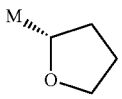 | | B26 | 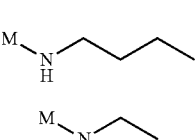 |
| B16 | 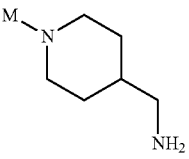 | | B27 | 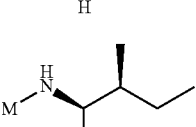 |
| B17 | 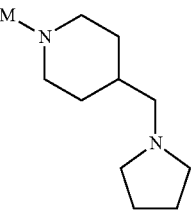 | | B28 | 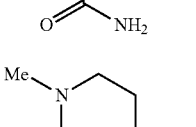 |
| B18 | 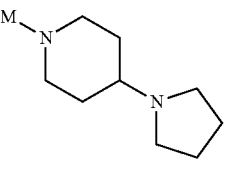 | | B29 | 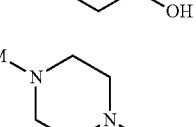 |
| | | | B30 | 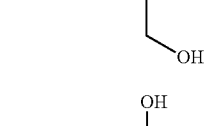 |
| B19 | 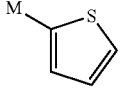 | | B31 | 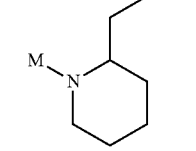 |
| B20 | 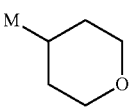 | | B32 | 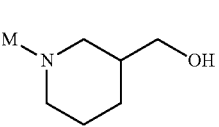 |
| B21 | 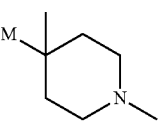 | | B33 | 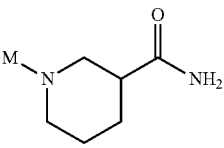 |
| B22 | 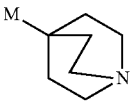 | | B34 |  |

TABLE II-continued
| | | | | |
|---|---|---|---|---|
| B35 | 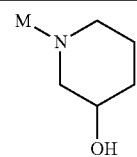 | | B46 | 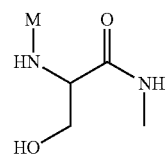 |
| B36 | 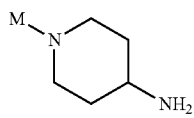 | | B47 | 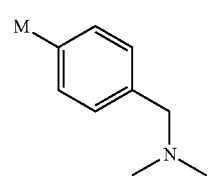 |
| B37 | 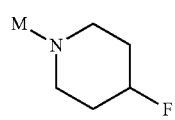 | | | |
| B38 | 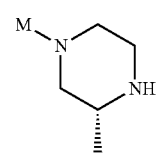 | | B48 | 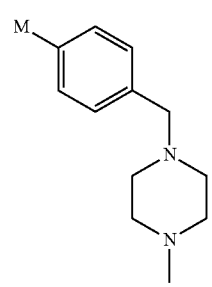 |
| B39 | 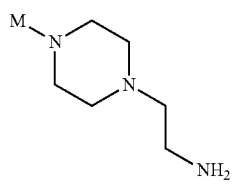 | | | |
| | | | B49 | 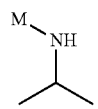 |
| B40 | 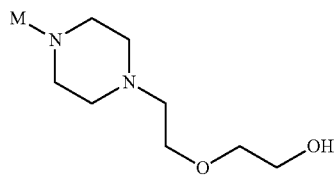 | | B50 | 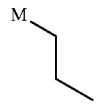 |
| B41 | 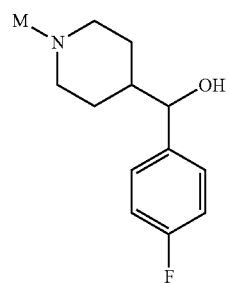 | | B51 | 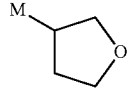 |
| | | | B52 | 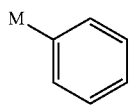 |
| B42 | 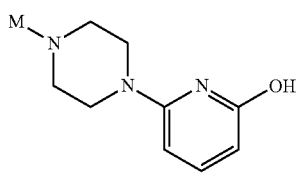 | | B53 | 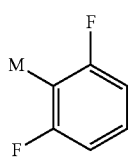 |
| B43 | 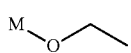 | | B54 | 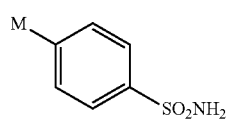 |
| B44 | 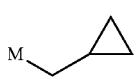 | | B55 | 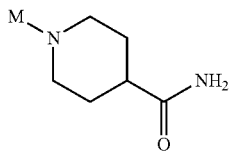 |
| B45 | 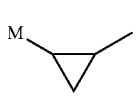 | | | |

EXAMPLE 1

N-(2-cyanoethyl)-2-methylalanine 50 g (0.48 mol) of 2-methylalanine were added to a cooled solution (water/ice) of NaOH (19.6 g) in water (100 ml). Once the solution had turned clear, 34 ml (0.50 mol) of acrylonitrile were dropped on cooling. The mixture was left overnight. After 18 hours, 28 ml of acetic acid were added on cooling (water/ice); a white solid precipitated; 200 ml of 95% ethanol were dropped in the flask, stirring was continued for 1 hour, then the mixture was allowed to stand in a fridge for 2-3 hours. After filtration, the solid was collected and dried in an oven at 80° C. The filtrates were evaporated and taken up with ethanol (160 ml). On cooling a further amount of product was obtained, which was filtered and dried. 72 g of the title compound were obtained from the first filtration. Total yield: 95%.

ESI MS: m/z 157 (MH+);
$^1$H NMR (400 MHz, DMSO-$d_6$): δ 7.47 (s, 1H), 2.70 (t, 2H), 2.48 (t, 2H), 1.18 (s, 6H).

By working in an analogous manner the following compound was prepared:

1-[(2-Cyanoethyl)amino]cyclopropanecarboxylic acid

EI MS: m/z 154 (M), 136 (M−H$_2$O), 114 (M−CH2CN), 68 (100%, cyclopr=C=O);
$^1$H NMR (400 MHz, DMSO-$d_6$): δ 7.47 (s, 1H), 2.86 (t, 2H, J=6.6 Hz), 2.48 (t, 2H, J=6.6 Hz), 1.09 (dd, 2H, J=6.9 Hz, J=4.1 Hz), 0.86 (dd, 2H, J=6.9 Hz, J=4.1 Hz).

EXAMPLE 2

N-(tert-butoxycarbonyl)-N-(2-cyanoethyl)-2-methylalanine 44.5 g (0.285 mol) of N-(2-cyanoethyl)-2-methylalanine and 51.7 g of tetramethylammonium hydroxide pentahydrate were dissolved in acetonitrile (2 l) at 40° C. and when a clear solution was obtained, 112 g of Boc$_2$O were added. The mixture was left for 24 hours at 40° C. The day after, further 20 g of Boc$_2$O were added while maintaining the temperature of 40° C. Every 8-12 hours 20 g of Boc$_2$O were added up to a total of 192 g. After 4 days the solvent was evaporated, the residue taken up with water (1000 ml) and washed twice with ethyl ether (500 ml). The aqueous fraction was brought to pH 3-4 with citric acid and extracted with ethyl acetate, washed with water (200 ml) and concentrated. 52 g of the title compound were obtained. (yield: 72%).

ESI MS: m/z 274 (M+NH4);
$^1$H NMR (400 MHz, DMSO-$d_6$): δ 3.52 (t, 2H, J=6.8 Hz)), 2.68 (t, 2H, J=6.8 Hz), 1.18-1.38 (m, 15H).

By working in an analogous manner the following compound was prepared:

1-[(tert-Butoxycarbonyl)(2-cyanoethyl)amino]cyclopropanecarboxylic acid

ESI MS: m/z 272 (M+NH4), 255 (MH+);
$^1$H NMR (400 MHz, DMSO-$d_6$): δ 12.55 (bs, 1H), 3.33 (m, 2H), 2.71 (m, 2H), 0.97-1.63 (m, 13H).

EXAMPLE 3

Methyl N-(tert-butoxycarbonyl)-N-(2-cyanoethyl)-2-methylalaninate 62 g (0.23 mol) of N-(tert-butoxycarbonyl)-N-(2-cyanoethyl)-2-methylalanine were dissolved in 350 ml of DMF and 50 g of KHCO$_3$ were added. Few minutes after, 30 ml of methyl iodide (MeI) were dropped and the mixture was stirred at room temperature for 6 hours. Then a further 15 ml of MeI were added. The mixture was left at room temperature overnight. After dilution with 1.5 l of water, the solution was extracted with ethyl acetate (3 times). The organic phases were washed with a small amount of water, dried over sodium sulfate, evaporated and dried at the mechanical pump. 60.5 g (97%) of methyl N-(tert-butoxycarbonyl)-N-(2-cyanoethyl)-2-methylalaninate were thus obtained.

ESI MS: m/z 288 (M+NH4);
$^1$H NMR (400 MHz, DMSO-$d_6$): δ 3.55 (m, 5H), 2.70 (t, 2H, J=6.7 Hz)), 1.40 (s, 6H), 1.36 (s, 9H).

By working in an analogous manner the following compound was prepared:

Methyl 1-[(tert-butoxycarbonyl)(2-cyanoethyl)amino]cyclopropanecarboxylate

ESI MS: m/z 286 (M+NH4);
$^1$H NMR (400 MHz, DMSO-$d_6$): δ 3.61 (s, 3H), 3.42 (t, 2H, J=6.7 Hz), 2.71 (m, 2H), 1.07-1.62 (m, 13H).

EXAMPLE 4 tert-Butyl 4-cyano-3-hydroxy-2,2-dimethyl-2,5-dihydro-1H-pyrrole-1-carboxylate 45 g of methyl N-(tert-butoxycarbonyl)-N-(2-cyanoethyl)-2-methylalaninate were dissolved in dioxane (240 ml) under nitrogen and 7.9 g of sodium hydride were added. The mixture was refluxed for 6 hours (120° C. internal temperature), and then left to stand overnight at room temperature (TLC: CH$_2$Cl$_2$/EtOH 90/10). The solvent was evaporated, water was added (1000 ml) and the mixture was brought to pH 3-4 with citric acid. The aqueous layer was extracted 4 times with ethyl acetate, the extracts washed with a limited amount of water and evaporated. Then the residue was taken up with hexane, evaporated and crystallized from hexane. 33.1 g of tert-butyl 4-cyano-3-hydroxy-2,2-dimethyl-2,5-dihydro-1H-pyrrole-1-carboxylate were thus obtained (yield: 85%).

ESI MS: m/z 237 (M−H—);
$^1$H NMR (400 MHz, DMSO-$d_6$): δ 4.06-4.10 (2s, 2H, conformers), 1.48 (s, 6H), 1.47 (s, 9H).

By working in an analogous manner the following compound was prepared:

tert-Butyl 6-cyano-7-oxo-4-azaspiro[2.4]heptane-4-carboxylate

ESI MS: m/z 235 (M−H—);
$^1$H NMR (400 MHz, DMSO-$d_6$): δ 4.63 (t, 1H, J=9.8 Hz), 4.24 (t, 1H, J=10.2 Hz), 3.74 (t, 1H, J=10.2 Hz), 1.67-2.16 (m, 2H), 1.34-1.41 (s, 9H), 0.93-1.20 (m, 2H).

EXAMPLE 5 tert-Butyl 3-amino-6,6-dimethyl-2,6-dihydropyrrolo[3,4-c]pyrazole-5(4H)-carboxylate 32 g of tert-Butyl 4-cyano-3-hydroxy-2,2-dimethyl-2,5-dihydro-1H-pyrrole-1-carboxylate (0.134 mol) were added to 430 ml of absolute ethanol. To this solution, 9 ml (0.18 mol) of hydrazine hydrate were added, followed by 12 ml of glacial AcOH (1.5 eq); The mixture was stirred at 60° C. for 48 hours, the ethanol was removed, the residue was taken up with 400 ml of sodium hydrogencarbonate solution, and extracted several times with ethyl acetate up to total extraction of the desired product. The organic phases were dried and evaporated. After purification by flash chromatography (eluent: CHCl$_3$/EtOH 97/3) and trituration with a mixture of hexane/ethyl acetate 9/1, 25 g of title compound were obtained. Total yield 30.5 g (yield: 88%)

ESI MS: m/z 253 (MH+);
$^1$H NMR (400 MHz, DMSO-d$_6$): δ 4.06-4.10 (2s, 2H, conformers), 1.48 (2s, 6H, conformers), 1.47 (2s, 9H, conformers).

By working in an analogous manner the following compound was prepared:

tert-Butyl-3-amino-2,6-dihydropyrrolo[3,4-c]pyrazole-6-spirocyclopropane-5(4H)-carboxylate ESI MS: m/z 251 (MH+);
$^1$H NMR (400 MHz, DMSO-d$_6$): δ 11.12 (bs, 1H), 5.13 (bs, 2H), 4.16-4.33 (m, 2H), 1.57-1.91 (m, 2H), 1.38 (s, 9H), 0.65-0.83 (m, 2H).

EXAMPLE 6

5-tert-Butyl 2-ethyl 3-amino-6,6-dimethylpyrrolo[3,4-c]pyrazole-2,5(4H,6H)-dicarboxylate and 5-tert-butyl 1-ethyl 3-amino-6,6-dimethyl-4,6-dihydropyrrolo[3,4-c]pyrazole-1,5-dicarboxylate 15 g of tert-Butyl 3-amino-6,6-dimethyl-2,6-dihydropyrrolo[3,4-c]pyrazole-5(4H)-carboxylate (59.4 mmol) were dissolved in anhydrous THF (150 ml) and treated, at 0° C. under Ar atmosphere, first with N,N-diisopropylethylamine (50 ml) and then with ClCO$_2$Et (4.65 ml, 1 eq.) dropwise. 90 minutes later, the solvent was diluted with EtOAc (1 l), washed with water and then with brine, dried over sodium sulfate and evaporated. The crude product was purified by flash chromatography (hexane/EtOAc 2/8) to afford 7.3 g of 5-tert-butyl 2-ethyl 3-amino-6,6-dimethylpyrrolo[3,4-c]pyrazole-2,5(4H,6H)-dicarboxylate as the major compound in 38% yield, together with 5.7 g of 5-tert-butyl 1-ethyl 3-amino-6,6-dimethyl-4,6-dihydropyrrolo[3,4-c]pyrazole-1,5-dicarboxylate in 30% yield.

5-tert-Butyl 2-ethyl 3-amino-6,6-dimethylpyrrolo[3,4-c]pyrazole-2,5(4H,6H)-dicarboxylate ESI MS: m/z 325 (MH+);
$^1$H NMR (400 MHz, DMSO-d$_6$): δ 4.35 (q, 2H), 4.10 (2s, 2H, conformers), 1.50-1.51 (m, 6H), 1.41-1.43 (2s, 9H, conformers), 1.29 (t, 3H).

5-tert-Butyl 1-ethyl 3-amino-6,6-dimethyl-4,6-dihydropyrrolo[3,4-c]pyrazole-1,5-dicarboxylate ESI MS: m/z 325 (MH+);
$^1$H NMR (400 MHz, DMSO-d$_6$): δ 4.28 (q, 2H, J=7.1 Hz), 4.09-4.14 (2s, 2H, conformers), 1.66-1.67 (m, 6H), 1.41-1.44 (2s, 9H, conformers), 1.27 (t, 3H, J=7.1 Hz).

By working in an analogous manner the following compounds were prepared:

5-tert-Butyl 2-ethyl 3-amino-pyrrolo[3,4-c]pyrazole-6-spirocyclopropane-2,5(4H,6H)-dicarboxylate ESI MS: m/z 323 (MH+);
$^1$H NMR (400 MHz, DMSO-d$_6$): δ 4.30 (q, 2H, J=7.1 Hz), 4.27 (bs, 2H), 1.65-2.01 (m, 2H), 1.38 (s, 9H) 1.27 (t, 3H, J=7.1 Hz), 0.82-0.96 (m, 2H).

5-tert-Butyl 1-ethyl 3-amino-4,6-dihydropyrrolo[3,4-c]pyrazole-6-spirocyclopropane-1,5-dicarboxylate ESI MS: m/z 323 (MH+);
$^1$H NMR (400 MHz, DMSO-d$_6$): δ 4.26 (bs, 2H), 4.21 (q, 2H, J=7.0 Hz), 1.36-1.97 (m, 13H), 1.23 (t, 3H, J=7.0 Hz).

EXAMPLE 7

5-tert-Butyl 1-ethyl 3-[(4-fluorobenzoyl)amino]-6,6-dimethyl-4,6-dihydro pyrrolo[3,4-c]pyrazole-1,5-dicarboxylate 5-tert-Butyl 1-ethyl 3-amino-6,6-dimethyl-4,6-dihydropyrrolo[3,4-c]pyrazole-1,5-dicarboxylate (2.0 g, 6.16 mmol) was dissolved in THF (40 ml), treated first with N,N-diisopropylethylamine (5.4 ml, 30.80 mmol) and then, at 0° C., with 4-fluorobenzoyl chloride (800 µl, 6.77 mmol) dissolved in THF (8 ml) dropwise. The reaction mixture was stirred at room temperature for 5 hours, concentrated and dissolved in DCM, washed with saturated sodium hydrogencarbonate aqueous solution and with brine. The organic phase was dried over sodium sulfate, evaporated and purified by flash chromatography (eluent: hexane/EtOAc 80/20) to afford 2.5 g of the title compound in 90% yield.

ESI MS: m/z 447 (MH+);
$^1$H NMR (400 MHz, DMSO-d$_6$): δ 11.47 (s, 1H), 8.04-8.17 (m, 2H), 7.25-7.37 (m, 2H), 4.44-4.47 (2s, 2H, conformers), 4.43 (q, 2H, J=7.1 Hz), 1.73-1.75 (2s, 6H, conformers), 1.43-1.46 (2s, 9H, conformers), 1.33 (t, 3H, J=7.1 Hz).

By working in an analogous manner the following compounds were prepared.

5-tert-Butyl 2-ethyl 3-[(4-fluorobenzoyl)amino]-6,6-dimethylpyrrolo[3,4-c]pyrazole-2,5(4H,6H)-dicarboxylate ESI MS: m/z 447 (MH+);
$^1$H NMR (400 MHz, DMSO-d$_6$): δ 10.78 (s, 1H), 7.95-7.99 (m, 2H), 7.40-7.47 (m, 2H), 4.51-4.49 (2s, 2H, conformers), 4.43 (q, 2H, J=7.1 Hz), 1.59-1.60 (2s, 6H), 1.43-1.46 (2s, 9H, conformers), 1.34 (t, 3H, J=7.1 Hz).

5-tert-Butyl 2-ethyl 3-[(4-fluorobenzoyl)amino]-pyrrolo[3,4-c]pyrazole-6-spirocyclopropane-2,5(4H,6H)-dicarboxylate ESI MS: m/z 445 (MH+);
$^1$H NMR (400 MHz, DMSO-d$_6$): δ 10.81 (s, 1H), 7.95-8.06 (m, 2H), 7.39-7.49 (m, 2H), 4.67 (bs, 2H), 4.41 (q, 2H, J=7.1 Hz), 1.80-2.10 (m, 2H), 1.41 (s, 9H), 1.32 (t, 3H, J=7.1 Hz), 0.93-1.06 (m, 2H).

EXAMPLE 8

5-tert-Butyl 1-ethyl 3-({[(3-fluorophenyl)amino]carbonyl}amino)-6,6-dimethyl-4,6-dihydropyrrolo[3,4-c]pyrazole-1,5-dicarboxylate 5-tert-Butyl 1-ethyl 3-amino-6,6-dimethyl-4,6-dihydropyrrolo[3,4-c]pyrazole-1,5-dicarboxylate (3.0 g, 9.24 mmol)

was dissolved in anhydrous THF (50 ml), treated at room temperature with 3-fluorophenyl-isocyanate (1.4 g, 10.21 mmol, 1.1 eq) and stirred overnight. The following day the reaction mixture was evaporated, taken up with DCM and washed with brine. The organic phase was dried over sodium sulfate and evaporated to dryness. Purification by flash chromatography (CH$_2$Cl$_2$/MeOH 90/10) afforded 3.05 g (yield 71%) of the title compound.

ESI MS: m/z 462 (MH+);
$^1$H NMR (400 MHz, DMSO-d$_6$): δ 9.74 (s, 1H), 9.05 (s, 1H), 7.44 (m, 1H), 7.33 (m, 1H), 7.16 (m, 1H), 6.84 (m, 1H), 4.43 (m, 4H), 1.76 (2s, 6H), 1.48 (2s, 9H, conformers), 1.36 (t, 3H, J=7.1 Hz).

EXAMPLE 9

5-tert-Butyl 1-ethyl 3-[(piperidine-1-carbonyl)-amino]-6,6-dimethyl-4,6-dihydropyrrolo[3,4-c]pyrazole-1,5-dicarboxylate To a solution of triphosgene (550 mg, 1.85 mmol, 0.4 eq) in tetrahydrofuran (50 ml) was added, at −40° C., a solution of 5-tert-butyl 1-ethyl 3-amino-6,6-dimethyl-4,6-dihydropyrrolo[3,4-c]pyrazole-1,5-dicarboxylate (1.5 g, 4.62 mmol) in tetrahydrofuran (50 ml) and N,N-diisopropylethylamine (1.8 ml, 2.2 eq). After 3 hours, a solution of piperidine (690 μl, 1.5 eq) and N,N-diisopropylethylamine (1.2 ml, 1.5 eq) in tetrahydrofuran (25 ml) was added. The reaction was allowed to reach room temperature in 2 hours (TLC: EtOAc/hexane 90/10). After evaporation of the solvent the solid was dissolved in DCM and the solution was washed with brine, the organic phase was dried over sodium sulfate and concentrated. The solid was purified by flash chromatography (eluent: EtOAc/hexane 50/50). The solid was treated with diisopropylether and filtered to afford 1.45 g of the title compound in 72% yield.

ESI MS: m/z 436 (MH+);
$^1$H NMR (400 MHz, DMSO-d$_6$): δ 9.36 (s, 1H), 4.46 (m, 4H), 3.40 (m, 4H), 1.76 (2s, 6H), 1.54 (m, 6H), 1.44 (2s, 9H, conformers), 1.36 (t, 3H, J=7.1 Hz).

EXAMPLE 10

Ethyl 3-[(4-fluorobenzoyl)amino]-6,6-dimethyl-5,6-dihydropyrrolo[3,4-c]pyrazole-1(4H)-carboxylate hydrochloride 5-tert-Butyl 1-ethyl 3-[(4-fluorobenzoyl)amino]-6,6-dimethyl-4,6-dihydropyrrolo[3,4-c]pyrazole-1,5-dicarboxylate (2.5 g, 5.59 mmol) was dissolved in dioxane (50 ml) and treated with HCl 4M in dioxane (28 ml, 20 eq). After 2 hours at 40° C. (TLC: CH$_2$Cl$_2$/MeOH 90/10) the reaction mixture was concentrated and the residue was treated with diethyl ether, filtered to afford the title compound (2.09 g) as a solid in 98% yield.

ESI MS: m/z 347 (MH+);
$^1$H NMR (400 MHz, DMSO-d$_6$): δ 11.28 (s, 1H), 8.06-8.11 (m, 2H), 7.28-7.34 (m, 2H), 4.40 (q, 2H, J=7.1 Hz), 3.92 (s, 2H), 1.42 (s, 6H), 1.33 (t, 3H, J=7.1 Hz).

By working in an analogous manner the following compounds were prepared:

Ethyl 3-[(4-fluorobenzoyl)amino]-6,6-dimethyl-5,6-dihydropyrrolo[3,4-c]pyrazole-2(4H)-carboxylate hydrochloride ESI MS: m/z 347 (MH+);
$^1$H NMR (400 MHz, DMSO-d$_6$): δ 10.92 (s, 1H), 9.89 (s, 1H), 8.02 (m, 2H), 7.49 (m, 2H), 4.61 (s, 2H), 4.51 (q, 2H, J=7.1 Hz), 1.69 (s, 6H), 1.39 (t, 3H, J=7.1 Hz).

Ethyl 3-[(4-fluorobenzoyl)amino]-5,6-dihydropyrrolo[3,4-c]pyrazole-6-spirocyclopropane-2(4H)-carboxylate hydrochloride ESI MS: m/z 345 (MH+);
$^1$H NMR (400 MHz, DMSO-d$_6$): δ 10.87 (bs, 1H), 10.00 (bs, 2H), 7.93-8.04 (m, 2H), 7.39-7.53 (m, 2H), 4.69 (bs, 2H), 4.41 (q, 2H, J=7.1 Hz), 1.68 (dd, 2H, J=8.6 Hz, J=6.1 Hz), 1.41 (dd, 2H, J=8.6 Hz, J=6.1 Hz), 1.33 (t, 3H, J=7.1 Hz).

EXAMPLE 11

Ethyl 5-(2,2-dimethylpropanoyl)-3-[(4-fluorobenzoyl)amino]-6,6-dimethyl-5,6-dihydropyrrolo[3,4-c]pyrazole-1(4H)-carboxylate Ethyl 3-[(4-fluorobenzoyl)amino]-6,6-dimethyl-5,6-dihydropyrrolo[3,4-c]pyrazole-1(4H)-carboxylate hydrochloride (2.0 g, 5.77 mmol) in dichloromethane (70 ml) was treated, at 0° C., with N,N-diisopropylethylamine (1.6 ml, 9.2 mmol, 1.6 eq) and with pivaloyl chloride (780 μL, 6.3 mmol, 1.1 eq). Gradually, the reaction was brought to room temperature and stirred overnight (TLC: CH$_2$Cl$_2$/EtOAc 90/10). The solution was washed with saturated sodium hydrogencarbonate aqueous solution and brine. The organic phase was dried over sodium sulfate, evaporated and purified by flash chromatography (eluent: CH$_2$Cl$_2$/EtOAc 90/10) to afford 2.03 g of the title compound in 82% yield.

ESI MS: m/z 431 (MH+);
$^1$H NMR (400 MHz, DMSO-d$_6$): δ 11.51 (s, 1H), 8.05-8.14 (m, 2H), 7.23-7.37 (m, 2H), 4.90 (s, 2H), 4.42 (q, 2H, J=7.1 Hz), 1.80 (s, 6H), 1.33 (t, 3H, J=7.1 Hz), 1.22 (s, 9H).

By working in an analogous manner the following compound was prepared:

Ethyl 5-(2,2-dimethylpropanoyl)-3-[(4-fluorobenzoyl)amino]-5,6-dihydro pyrrolo[3,4-c]pyrazole-6-spirocyclopropane-2(4H)-carboxylate ESI MS: m/z 429 (MH+);
$^1$H NMR (400 MHz, DMSO-d$_6$): δ 10.81 (bs, 1H), 7.96-8.04 (m, 2H), 7.38-7.48 (m, 2H), 5.10 (bs, 2H), 4.42 (q, 2H, J=7.1 Hz), 2.33 (dd, 2H, J=6.8 Hz, J=4.2 Hz), 1.32 (t, 3H, J=7.1 Hz), 1.22 (s, 9H), 0.90 (dd, 2H, J=6.8 Hz, J=4.2 Hz).

EXAMPLE 12

N-[5-(2,2-dimethylpropanoyl)-6,6-dimethyl-1,4,5,6-tetrahydropyrrolo[3,4-c]pyrazol-3-yl]-4-fluorobenzamide Ethyl 5-(2,2-dimethylpropanoyl)-3-[(4-fluorobenzoyl)amino]-6,6-dimethyl-5,6-dihydropyrrolo[3,4-c]pyrazole-1(4H)-carboxylate (2.0 g, 4.64 mmol) was dissolved in methanol (60 ml), treated with TEA (6.45 ml, 46.4 mmol, 10 eq) and stirred overnight at room temperature. (TLC: CH$_2$Cl$_2$/MeOH 95/5). After evaporation, the solid was treated with diethyl ether/hexane and filtered to afford 1.43 g of the title compound in 86% yield.

ESI MS: m/z 359 (MH+);

$^1$H NMR (400 MHz, DMSO-d$_6$): δ 12.41 (bs, 1H), 10.91 (bs, 1H), 7.98-8.11 (m, 2H), 7.20-7.44 (m, 2H), 4.66-4.92 (bs, 2H), 1.64 (s, 6H), 1.21 (s, 9H).

By working in an analogous manner the following compounds were prepared:

N-[5-(2,2-dimethylpropanoyl)-2,4,5,6-tetrahydropyrrolo[3,4-c]pyrazol-6-spirocyclopropan-3-yl]-4-fluorobenzamide ESI MS: m/z 357 (MH+);

$^1$H NMR (400 MHz, DMSO-d$_6$): δ 11.59-12.47 (bs, 1H), 10.94 (bs, 1H), 8.02-8.11 (m, 2H), 7.27-7.37 (m, 2H), 4.99 (s, 2H), 2.25 (dd, 2H, J=6.5 Hz, J=4.4 Hz), 1.20 (s, 9H), 0.79 (dd, 2H, J=6.5 Hz, J=4.4 Hz).

N-{6,6-dimethyl-5-[(2R)-tetrahydrofuran-2-ylcarbonyl]-1,4,5,6-tetrahydropyrrolo[3,4-c]pyrazol-3-yl}-4-fluorobenzamide ESI MS: m/z 373 (MH+);

$^1$H NMR (400 MHz, DMSO-d$_6$): δ 12.49 (bs, 1H), 10.96 (bs, 1H), 8.09 (m, 2H), 7.34 (m, 2H), 4.86 (m, 2H), 4.56 (t, 1H), 3.83 (m, 2H) 2.02 (m, 2H), 1.86 (m, 2H), 1.68 (s, 6H).

α$_D$+27.7 (c=0.50, MeOH)

N-{6,6-dimethyl-5-[(2S)-tetrahydrofuran-2-ylcarbonyl]-1,4,5,6-tetrahydropyrrolo[3,4-c]pyrazol-3-yl}-4-fluorobenzamide ESI MS: m/z 373 (MH+);

$^1$H NMR (400 MHz, DMSO-d$_6$): δ 12.49 (bs, 1H), 10.96 (bs, 1H), 8.09 (m, 2H), 7.34 (m, 2H), 4.86 (m, 2H), 4.56 (t, 1H), 3.83 (m, 2H) 2.02 (m, 2H), 1.86 (m, 2H), 1.68 (s, 6H).

α$_D$-25.9 (c=0.76, MeOH)

EXAMPLE 13

4-(1-Methyl-piperidin-4-yloxy)-benzoic acid methyl ester

To a solution of 1-methyl-piperidin-4-ol (6.8 g. 59 mmoles), PPh$_3$ (triphenylphosphine, 15.5 g, 59 mmoles) and 4-hydroxy-benzoic acid methyl ester (6 g, 39 mmoles) in THF (150 ml) at 0° C., diethyl azodicarboxylate (9.5 ml, 59 mmoles) in THF (30 ml) was slowly added. The reaction mixture was allowed to warm to room temperature over a period of 24 hours. It was then evaporated and the residue redissolved in 5% aqueous citric acid (700 ml). The solution was washed with ethyl acetate (3×250 ml), made alkaline with concentrated NH$_4$OH (pH~8) and then extracted with dichloromethane (3×250 ml). The combined dichloromethane extracts were washed with brine, dried and evaporated to give an oil which was purified by flash chromatography on silica gel using dichloromethane-MeOH (90:10) as eluent, to give the title compound as a yellow oil (7.4 g, 75%).

ESI MS: m/z 250 (MH+);

1H NMR (400 MHz, DMSO-D6) δ ppm 1.7 (m, 2H) 2.0 (m, 2H) 2.2 (m, 5H) 2.7 (m, 2H) 3.8 (s, 3H) 4.5 (m, 1H) 7.1 (d, J=9.0 Hz, 2H) 7.9 (d, J=9.0 Hz, 2H).

EXAMPLE 14

4-(1-Methyl-piperidin-4-yloxy)-benzoic acid, hydrochloride 4-(1-Methyl-piperidin-4-yloxy)-benzoic acid methyl ester (7.3 g, 29 mmoles) was dissolved in 6N aq HCl (220 ml). After heating at 85° C. for 6 hours, the solvent was removed in vacuo. The residue was taken up with water and evaporated twice and then taken up with acetone two more times. The solid obtained was finally triturated in acetone to give the hydrochloride salt as a white powder (6.4 g, 80% yield).

1H NMR (400 MHz, DMSO-D6) δ ppm 2.0 (m, 4H) 2.8 (m, 3H) 3.3 (m, 4H) 4.7 (m, 1H) 7.1 (m, 2H) 7.9 (m, 2H) 9.9 (d, J=20.4 Hz, 1H) 12.6 (s, 1H).

EXAMPLE 15

4-(4-Hydroxy-piperidin-1-yl)benzoic acid ethyl ester

A mixture of 4-fluoro-benzoic acid ethyl ester (1.68 g, 10 mmoles), piperidin-4-ol (1.12 g, 11 mmoles) and anhydrous potassium carbonate (1.38 g, 10 mmoles) in DMSO (10 ml) was heated at 120° C. for 6 hours. After cooling, the mixture was poured into water and ice (500 ml) and extracted with ethyl acetate. The organic layer was washed with water and brine, dried and evaporated. The residue was purified by flash chromatography on silica gel using hexane/EtOAc (10/30) as eluent to give the title compound as a white solid (1.6 g, 64%).

ESI MS: m/z 250 (MH+);

1H NMR (400 MHz, DMSO-D6) δ ppm 1.3 (t, J=7.1 Hz, 3H) 1.4 (m, 2H) 1.8 (m, 2H) 3.0 (m, 2H) 3.7 (m, 2H) 4.2 (q, J=7.1 Hz, 2H) 4.7 (d, J=4.3 Hz, 1H) 6.9 (m, 2H) 7.7 (m, 2H).

EXAMPLE 16

4-(4-Fluoro-piperidin-1-yl)benzoic acid ethyl ester

To a solution of 4-(4-hydroxy-piperidin-1-yl)benzoic acid ethyl ester (1.25 g. 5 mmoles) in dry dichloromethane (30 ml) at room temperature under an inert atmosphere, it was slowly added DAST (0.97 g, 6 mmoles) in dichloromethane (5 ml). The reaction mixture was stirred at room temperature for 1 hour and then quenched with aqueous NaHCO$_3$. The organic layer was washed with brine, dried and evaporated. The residue was purified by flash chromatography on silica gel using hexane/EtOAc (70/30) as eluent to give the title compound as a white solid (0.7 g, 56%).

ESI MS: m/z 252 (MH+);

1H NMR (400 MHz, DMSO-D6) δ ppm 1.3 (t, J=7.1 Hz, 3H) 1.8 (m, 2H) 2.0 (m, 2H) 3.3 (m, 2H) 3.6 (m, 2H) 4.2 (s, 2H) 4.8 (s, 1H) 7.0 (s, 2H) 7.8 (s, 2H).

EXAMPLE 17

4-(4-Fluoro-piperidin-1-yl)benzoic acid

A mixture of 4-(4-fluoro-piperidin-1-yl)benzoic acid ethyl ester (0.7 g, 2.7 mmoles) in ethanol (50 ml) and a solution of 2N sodium hydroxide (20 ml) was stirred at room temperature for 24 hours. The ethanol was then evaporated, the solution diluted with water (20 ml) and neutralized with 2N HCl. The acid separated as a white solid which was washed with water and dried under vacuum (0.52 g, 82%).

ESI MS: m/z 224 (MH+);

1H NMR (400 MHz, DMSO-D6) δ ppm 1.8 (m, 2H) 2.0 (m, 2H) 3.3 (m, 2H) 3.5 (m, 2H) 5.0 (s, 1H) 7.0 (s, 2H) 7.8 (s, 2H) 12.2 (s, 1H).

By working as described in any previous example, that is by using any proper starting material and any suitable reactant according to the process previously disclosed, additional compounds of formula (Ia) and (Ib) were also prepared, as reported in the following table III. For explanatory notes concerning the coding system identifying each specific compound of formula (Ia) and (Ib) see the "general method" at the beginning of the experimental section.

TABLE III

| | |
|---|---|
| A02M1B01 | $^1$H NMR (400 MHz, DMSO-$d_6$): δ 12.45 (bs, 1H), 10.99 (s, 1H), 7.84 (m, 2H), 7.52 (m, 1H), 7.40 (m, 1H), 4.86 (s, 2H), 1.65 (s, 6H), 1.21 (s, 9H). |
| A03M1B01 | $^1$H NMR (400 MHz, DMSO-$d_6$): δ 12.46 (bs, 1H), 11.01 (s, 1H), 8.05 (m, 1H), 7.88 (m, 1H), 7.54 (m, 1H), 4.86 (s, 2H), 1.65 (s, 6H), 1.21 (s, 9H). |
| A04M1B01 | $^1$H NMR (400 MHz, DMSO-$d_6$): δ 12.45 (bs, 1H), 10.89 (s, 1H), 7.7 (m, 1H), 7.38 (m, 1H), 7.20 (s, 1H), 4.89 (s, 2H), 1.68 (s, 6H), 1.24 (s, 9H). |
| A05M1B01 | $^1$H NMR (400 MHz, DMSO-$d_6$): δ 12.54 (bs, 1H), 11.07 (s, 1H), 7.76 (s, 2H), 7.51 (s, 1H), 4.89 (s, 2H), 1.68 (s, 6H), 1.25 (s, 9H). |
| A06M1B01 | $^1$H NMR (400 MHz, DMSO-$d_6$): δ 12.43 (bs, 1H), 10.98 (s, 1H), 7.98 (d, 2H, J = 8.0 Hz), 7.54 (d, 2H, J = 8.0 Hz), 4.86 (s, 2H), 1.65 (s, 6H), 1.21 (s, 9H). |
| A07M1B01 | $^1$H NMR (400 MHz, DMSO-$d_6$): δ 12.47 (bs, 1H), 11.16 (s, 1H), 8.16 (d, 2H, J = 7.9 Hz), 7.85 (d, 2H, J = 7.9 Hz), 4.88 (s, 2H), 1.65 (s, 6H), 1.21 (s, 9H). |
| A08M1B01 | $^1$H NMR (400 MHz, DMSO-$d_6$): δ 12.50 (bs, 1H), 11.17 (s, 1H), 9.13 (s, 1H,), 8.76 (m, 1H), 8.33 (m, 1H) 7.51 (m, 1H), 4.91 (s, 2H), 1.69 (s, 6H), 1.25 (s, 9H). |
| A09M1B01 | $^1$H NMR (400 MHz, DMSO-$d_6$): δ 12.54 (bs, 1H), 11.25 (s, 1H), 8.75 (d, 2H), 7.91 (d, 2H), 4.92 (s, 2H), 1.69 (s, 6H), 1.25 (s, 9H). |
| A10M1B01 | $^1$H NMR (400 MHz, DMSO-$d_6$): δ 12.47 (bs, 1H), 11.00 (s, 1H), 8.12 (m, 1H), 7.86 (m, 1H), 7.12 (m, 1H), 4.86 (s, 2H), 1.68 (s, 6H), 1.25 (s, 9H). |
| A11M1B01 | $^1$H NMR (400 MHz, DMSO-$d_6$): δ 12.11 (bs, 1H), 10.77 (s, 1H), 8.45 (s, 1H), 7.69 (m, 2H), 4.89 (s, 2H), 1.68 (s, 6H), 1.25 (s, 9H). |
| A12M1B01 | $^1$H NMR (400 MHz, DMSO-$d_6$): δ 12.22 (bs, 1H), 10.31 (s, 1H), 4.76 (s, 2H), 2.12 (m, 3H), 1.61 (s, 6H), 1.19 (s, 9H), 0.87 (d, 6H, J = 6.5 Hz). |
| A13M1B01 | $^1$H NMR (400 MHz, DMSO-$d_6$): δ 12.21 (bs, 1H), 10.19 (bs, 1H), 4.80 (s, 2H), 3.28 (m, 1H), 2.25-1.70 (m, 6H), 1.60 (s, 6H), 1.20 (s, 9H). |
| A14M1B01 | $^1$H NMR (400 MHz, DMSO-$d_6$): δ 12.35 (bs, 1H), 10.38 (bs, 1H), 4.75 (s, 2H), 1.82 (m, 1H), 1.60 (s, 6H), 1.20 (s, 9H), 0.78 (m, 4H). |
| A15M1B01 | $^1$H NMR (400 MHz, DMSO-$d_6$): δ 12.3 (bs, 1H), 9.89 (s, 1H), 4.80 (s, 2H), 1.64 (s, 6H), 1.23 (s, 9H), 1.21 (s, 9H). |
| A16M1B01 | $^1$H NMR (400 MHz, DMSO-$d_6$): δ 12.35 (bs, 1H), 11.02 (s, 1H), 8.09 (d, 2H, J = 8.2 Hz), 7.47 (d, 2H, J = 8.2 Hz), 4.85 (s, 2H), 1.64 (s, 6H), 1.21 (s, 9H). |
| A19M1B01 | $^1$H NMR (400 MHz, DMSO-$d_6$): δ 12.48 (bs, 1H), 10.82 (s, 1H), 8.43 (m, 1H), 7.45 (m, 1H), 6.70 (m, 1H), 4.85 (s, 2H), 1.67 (s, 6H), 1.25 (s, 9H). |
| A20M1B01 | $^1$H NMR (400 MHz, DMSO-$d_6$): δ 12.26 (bs, 1H), 10.38 (s, 1H), 4.80 (s, 2H), 3.04 (m, 2H), 2.52 (m, 3H), 1.64 (m, 10H), 1.23 (s, 9H). |
| A22M1B01 | $^1$H NMR (400 MHz, DMSO-$d_6$): δ 12.43 (bs, 1H), 11.06 (s, 1H), 8.3-7.6 (m, 7H), 4.99 (s, 2H), 1.71 (m, 6H), 1.26 (s, 9H). |
| A23M1B01 | $^1$H NMR (400 MHz, DMSO-$d_6$): δ 12.48 (bs, 1H), 11.07 (s, 1H), 8.68 (s, 1H), 8.08 (m, 4H), 7.66 (m, 2H), 4.95 (s, 2H), 1.70 (m, 6H), 1.27 (s, 9H). |
| A24M1B01 | $^1$H NMR (400 MHz, DMSO-$d_6$): δ 12.05 (bs, 1H), 8.87 (s, 1H), 7.19 (m, 4H), 6.91 (bs, 1H), 4.73 (s, 2H), 4.32 (d, 2H, J = 5.85 Hz), 2.30 (s, 3H), 1.63 (s, 6H), 1.22 (s, 9H). |
| A25M1B01 | $^1$H NMR (400 MHz, DMSO-$d_6$): δ 12.31-12.05 (2bs, 1H), 8.48 (s, 1H), 7.30 (m, 5H), 7.00 (bs, 1H), 4.73 (s, 2H), 4.33 (d, 2H, J = 5.85 Hz), 1.63 (s, 6H), 1.22 (s, 9H). |
| A28M1B01 | $^1$H NMR (400 MHz, DMSO-$d_6$): δ 12.07 (bs, 1H), 8.99 (s, 1H), 4.72 (s, 2H), 3.40 (m, 4H), 1.63 (s, 6H), 1.5 (m, 6H), 1.22 (s, 9H). |
| A29M1B01 | $^1$H NMR (400 MHz, DMSO-$d_6$): δ 12.36 (bs, 1H), 10.08 (s, 1H), 4.82 (s, 2H), 3.15 (bs, 2H), 2.32 (s, 6H), 1.65 (s, 6H), 1.23 (s, 9H). |
| A02M2B01 | $^1$H NMR (400 MHz, DMSO-$d_6$): δ 12.29 (bs, 1H), 11.05 (s, 1H), 7.9-7.35 (m, 3H), 5.03 (s, 2H), 2.29 (m, 2H), 1.24 (s, 9H), 0.84 (m, 2H). |
| A04M2B01 | $^1$H NMR (400 MHz, DMSO-$d_6$): δ 12.21 (bs, 1H), 10.90 (s, 1H), 7.79 (m, 1H), 7.40 (m, 1H), 7.21 (m, 1H), 5.03 (s, 2H), 2.29 (m, 2H), 1.24 (s, 9H), 0.83 (m, 2H). |

TABLE III-continued

| | |
|---|---|
| A05M2B01 | ¹H NMR (400 MHz, DMSO-d₆): δ 12.30 (bs, 1H), 11.17 (s, 1H), 7.77 (s, 2H), 7.51 (s, 1H), 5.04 (s, 2H), 2.29 (m, 2H), 1.24 (s, 9H), 0.84 (m, 2H). |
| A06M2B01 | ¹H NMR (400 MHz, DMSO-d₆): δ 12.28 (bs, 1H), 11.04 (s, 1H), 8.03 (d, 2H, J = 8.0 Hz), 7.61 (d, 2H, J = 8.0 Hz), 5.03 (s, 2H), 2.29 (m, 2H), 1.24 (s, 9H), 0.83 (m, 2H). |
| A07M2B01 | ¹H NMR (400 MHz, DMSO-d₆): δ 12.32 (bs, 1H), 11.22 (s, 1H), 8.21 (d, 2H, J = 7.9 Hz), 7.91 (d, 2H, J = 7.9 Hz), 5.05 (s, 2H), 2.29 (m, 2H), 1.24 (s, 9H), 0.84 (m, 2H). |
| A10M2B01 | ¹H NMR (400 MHz, DMSO-d₆): δ 12.23 (bs, 1H), 11.02 (s, 1H), 8.10 (m, 1H), 7.87 (m, 1H), 7.22 (m, 1H), 5.01 (s, 2H), 2.29 (m, 2H), 1.24 (s, 9H), 0.84 (m, 2H). |
| A12M2B01 | ¹H NMR (400 MHz, DMSO-d₆): δ 12.03 (bs, 1H), 10.36 (bs, 1H), 4.95 (s, 2H), 2.26 (m, 2H), 2.17 (m, 2H), 2.09 (m, 1H), 1.22 (s, 9H), 0.93 (m, 6H), 0.80 (m, 2H). |
| A13M2B01 | ¹H NMR (400 MHz, DMSO-d₆): δ 12.05 (bs, 1H), 10.28 (bs, 1H), 4.96 (s, 2H), 3.32 (m, 1H), 2.25 (m, 8H), 1.23 (s, 9H), 0.78 (m, 2H). |
| A14M2B01 | ¹H NMR (400 MHz, DMSO-d₆): δ 12.03 (bs, 1H), 10.72 (bs, 1H), 4.91 (s, 2H), 2.25 (m, 2H), 1.82 (m, 1H), 1.20 (s, 9H), 0.80 (m, 6H). |
| A15M2B01 | ¹H NMR (400 MHz, DMSO-d₆): δ 12.01 (bs, 1H), 9.92 (s, 1H), 4.94 (s, 2H), 2.25 (m, 2H), 1.22 (s, 18H), 0.78 (m, 2H). |
| A19M2B01 | ¹H NMR (400 MHz, DMSO-d₆): δ 12.21 (bs, 1H), 10.82 (s, 1H), 7.92 (m, 1H), 7.49(m, 1H), 6.69 (m, 1H), 5.01 (s, 2H), 2.29 (m, 2H), 1.24 (s, 9H), 0.83 (m, 2H). |
| A27M2B01 | 'H NMR (400 MHz, DMSO-d₆): δ 11.98 (bs, 1H), 9.02 (s, 2H), 7.45 (m, 1H), 7.33 (m, 1H), 7.13 (m, 1H), 6.81 (m, 1H), 4.96 (s, 2H), 2.27 (m, 2H), 1.23 (s, 9H), 0.81 (m, 2H). |
| A28M2B01 | ¹H NMR (400 MHz, DMSO-d₆): δ 11.83 (bs, 1H), 9.03 (s, 1H), 4.87 (s, 2H), 3.41 (m, 4H), 2.23 (m, 2H), 1.58 (m, 2H), 1.49 (m, 4H), 1.22 (s, 9H), 0.76 (m, 2H). |
| A30M1B01 | ¹H NMR (400 MHz, DMSO-d₆): δ ppm 1.2 (s, 9 H) 1.7 (s, 6 H) 4.9 (s, 2 H) 7.4-8.1 (m, 5 H) 11.2 (s, 1 H) 12.5 (s, 1 H) |
| A31M1B01 | ¹H NMR (400 MHz, DMSO-d₆): δ ppm 1.2 (s, 9 H) 1.7 (s, 6 H) 1.7 (m, 2 H) 2.0 (m, 2 H) 2.2 (s, 3 H) 2.3 (m, 2 H) 2.7 (m, 2 H) 4.5 (m, 1 H) 4.9 (s, 2 H) 7.0 (d, J = 7.9 Hz, 2 H) 8.0 (d, J = 7.9 Hz, 2 H) 10.7 (s, 1 H) 12.4 (s, 1 H) |
| A32M1B01•HCl | ¹H NMR (400 MHz, DMSO-d₆): (mixture of two conformers) δ ppm 1.25 (s, 18 H) 1.68 (s, 12 H) 1.84 (m, 2 H) 2.07 (m, 4 H) 2.29 (d, J = 14.0 Hz, 2 H) 2.80 (d, J = 5.0 Hz, 3 H) 2.82 (d, J = 5.0 Hz, 3 H) 3.11 (m, 2 H) 3.20 (m, 3 H) 3.40 (m, 2 H) 3.52 (d, J = 14.0 Hz, 2 H) 4.67 (m, 1 H) 4.87 (m, 1 H) 4.89 (s, 4 H) 7.21 (dd, J = 8.8, 2.3 Hz, 1H) 7.25 (dd, J = 8.8, 2.3 Hz, 1H) 7.45 (m, 2 H) 7.5-7.7 (m, 4 H) 9.90 (bs, 1 H) 9.97 (bs, 1 H) 10.93 (s, 2 H) 12-13 (bs, 2 H). |
| A33M1B01•2HCl | ¹H NMR (400 MHz, DMSO-d₆): δ ppm 1.3 (s, 9 H) 1.7 (s, 6 H) 2.8 (s, 3 H) 3.4 (m, 10 H) 4.9 (s, 2 H) 7.6 (s, 2 H) 8.1 (d, J = 7.9 Hz, 2 H) 10.4 (s, 1 H) 11.0 (s, 1 H) |
| A34M1B01•HCl | ¹H NMR (400 MHz, DMSO-d₆): δ ppm 1.3 (s, 9 H) 1.7 (s, 6 H) 1.9 (m, 4 H) 3.4 (m, 4 H) 4.9 (m, 1 H) 4.9 (s, 2 H) 7.0 (d, J = 9.1 Hz, 2 H) 7.9 (d, J = 9.0 Hz, 2 H) 10.6 (s, 1 H) |
| A35M1B01 | ¹H NMR (400 MHz, DMSO-d₆): δ ppm 1.2 (s, 9 H) 1.6 (s, 6 H) 2.3 (s, 3 H) 2.5 (m, 4 H) 3.1 (m, 2 H) 3.3 (m, 2 H) 4.8 (s, 2 H) 6.9 (d, J = 8.2 Hz, 2 H) 7.9 (d, J = 8.4 Hz, 2 H) 10.5 (s, 1 H) 12.3 (s, 1 H) |
| A36M1B01 | ¹H NMR (400 MHz, DMSO-d₆): δ ppm 1.2 (s, 9 H) 1.6 (s, 6 H) 2.1 (m, 2 H) 2.5 (t, J = 8.0 Hz, 2 H) 3.9 (t, J = 7.0 Hz, 2 H) 4.8 (s, 2 H) 7.8 (d, J = 8.9 Hz, 2 H) 8.0 (d, J = 8.8 Hz, 2 H) 10.8 (s, 1 H) 12.4 (s, 1 H) |
| A37M1B01 | ¹H NMR (400 MHz, DMSO-d₆): δ ppm 1.3 (s, 9 H) 1.7 (s, 6 H) 4.1 (m, 2 H) 4.5 (m, 2 H) 4.9 (s, 2 H) 7.7 (d, J = 8.2 Hz, 2 H) 8.1 (d, J = 7.8 Hz, 2 H) 10.9 (s, 1 H) 12.4 (s, 1 H) |
| A38M1B01 | ¹H NMR (400 MHz, DMSO-d₆): δ ppm 1.3 (s, 9 H) 1.7 (s, 6 H) 3.8 (s, 3 H) 3.9 (s, 3 H) 4.9 (s, 2 H) 7.1 (d, J = 8.5 Hz, 1 H) 7.6 (d, J = 1.2 Hz, 1 H) 7.7 (dd, J = 8.5, 2.0 Hz, 1 H) 10.8 (s, 1 H) 12.4 (s, 1 H) |
| A38M2B01 | ¹H NMR (400 MHz, DMSO-d₆): δ ppm 0.8 (m, 2 H) 1.2 (s, 9 H) 2.3 (m, 2 H) 3.8 (s, 3 H) 3.9 (s, 3 H) 5.0 (s, 2 H) 7.1 (m, 1 H) 7.6 (m, 1 H) 7.7 (m, 1 H) 10.8 (s, 1 H) 12.2 (s, 1 H) |
| A39M1B01 | ¹H NMR (400 MHz, DMSO-d₆): δ ppm 1.3 (s, 9 H) 1.7 (s, 6 H) 4.9 (s, 2 H) 7.5 (s, 1 H) 8.0 (d, J = 7.3 Hz, 2 H) 8.05 (d, J = 7.3 Hz, 2 H) 8.11 (s, 1 H) 11.0 (s, 1 H) 12.5 (s, 1 H) |
| A40M1B01 | ¹H NMR (400 MHz, DMSO-d₆): δ ppm 1.2 (s, 9 H) 1.6 (s, 3 H) 4.9 (s, 2 H) 8.0 (d, J = 8.4 Hz, 2 H) 8.1 (d, J = 8.5 Hz, 2 H) 11.2 (s, 1 H) 12.5 (s, 1 H) |
| A41M1B01 | ¹H NMR (400 MHz, DMSO-d₆): δ ppm 1.2 (s, 9 H) 1.7 (s, 6 H) 4.9 (s, 2 H) 7.7 (t, J = 7.6 Hz, 1 H) 8.1 (d, J = 7.6 Hz, 1 H) 8.3 (d, J = 7.9 Hz, 1 H) 8.4 (s, 1 H) 11.2 (s, 1 H) 12.5 (s, 1 H) |

TABLE III-continued

| | |
|---|---|
| A43M1B01 | $^1$H NMR (400 MHz, DMSO-d$_6$): δ ppm 1.2 (s, 9 H) 1.7 (s, 6 H) 4.9 (s, 2 H) 7.3 (m, 2 H) 7.6 (m, 1 H) 7.7 (m, 1 H) 10.9 (s, 1 H) 12.4 (s, 1 H) |
| A44M1B01 | $^1$H NMR (400 MHz, DMSO-d$_6$): δ ppm 1.25 (s, 9 H) 1.68 (s, 6 H) 3.85 (s, 3 H) 4.88 (s, 2 H) 7.03 (m, 2 H) 8.01 (d, J = 8.29 Hz, 2 H) 10.74 (s, 1 H) 12.40 (s, 1 H) |
| A45M1B01 | $^1$H NMR (400 MHz, DMSO-d$_6$): δ ppm 1.3 (s, 9 H) 1.7 (s, 6 H) 3.8 (s, 3 H) 4.9 (s, 2 H) 7.2 (m, 1 H) 7.4 (m, 1 H) 7.6 (m, 2 H) 10.9 (s, 1 H) 12.5 (s, 1 H) |
| A46M1B01 | $^1$H NMR (400 MHz, DMSO-d$_6$): δ ppm 1.3 (s, 9 H) 1.7 (s, 6 H) 4.0 (s, 3 H) 4.9 (s, 2 H) 7.1 (t, J = 7.4 Hz, 1 H) 7.2 (d, J = 8.3 Hz, 1 H) 7.6 (t, J = 7.8 Hz, 1 H) 7.8 (dd, J = 7.7, 1.7 Hz, 1 H) 10.3 (s, 1 H) 12.4 (s, 1 H) |
| A47M1B01 | $^1$H NMR (400 MHz, DMSO-d$_6$): δ ppm 1.2 (s, 9 H) 1.6 (s, 6 H) 3.6 (s, 2 H) 4.8 (s, 2 H) 7.25 (m, 1 H) 7.32 (m, 4 H) 10.7 (s, 1 H) 12.3 (s, 1 H) |
| A48M1B01 | $^1$H NMR (400 MHz, DMSO-d$_6$): δ ppm 1.16 (s, 9 H) 1.60 (s, 6 H) 3.78 (s, 2 H) 4.75 (s, 2 H) 7.47 (m, 3 H) 7.80 (s, 1 H) 7.86 (m, 3 H) 10.74 (s, 1 H) 12.30 (s, 1 H) |
| A49M1B01 | $^1$H NMR (400 MHz, DMSO-d$_6$): δ ppm 1.23 (s, 9 H) 1.67 (m, 14 H) 2.79 (m, 1 H) 4.80 (s, 2 H) 10.37 (s, 1 H) 12.23 (s, 1 H) |
| A50M1B01 | $^1$H NMR (400 MHz, DMSO-d$_6$): δ ppm 1.32 (m, 6 H) 1.23 (s, 9 H) 1.74 (m, 4 H) 1.64 (s, 6 H) 2.36 (m, 1 H) 4.79 (s, 2 H) 10.30 (s, 1 H) 12.21 (s, 1 H) |
| A51M1B01 | $^1$H NMR (400 MHz, DMSO-d$_6$): δ ppm 1.2 (s, 9 H) 1.6 (s, 6 H) 2.0 (m, 4 H) 3.9 (m, 2 H) 4.4 (dd, J = 8.2, 5.6 Hz, 1 H) 4.8 (s, 2 H) 10.1 (s, 1 H) 12.3 (s, 1 H) |
| A52M1B01•HCl | $^1$H NMR (400 MHz, DMSO-d$_6$): δ ppm 1.2 (s, 9 H) 1.6 (s, 6 H) 1.9 (m, 4 H) 2.6 (m, 1 H) 2.8 (m, 3 H) 3.0 (m, 2 H) 3.4 (m, 2 H) 4.8 (s, 2 H) 9.6 (s, 1 H) 10.6 (s, 1 H) 12.4 (s, 1 H) |
| A53M1B01 | $^1$H NMR (400 MHz, DMSO-d$_6$): δ ppm 1.2 (s, 9 H) 1.4 (m, 1 H) 1.5 (m, 1 H) 1.6 (s, 6 H) 1.7 (m, 2 H) 2.0 (s, 3 H) 2.6 (m, 2 H) 3.0 (t, J = 13.0 Hz, 1 H) 3.8 (d, J = 13.7 Hz, 1 H) 4.4 (d, J = 12.9 Hz, 1 H) 4.8 (s, 2 H) 10.4 (s, 1 H) 12.3 (s, 1 H) |
| A54M1B01 | $^1$H NMR (400 MHz, DMSO-d$_6$): δ 12.52 (bs, 1H), 11.23 (s, 1H), 8.30 (m, 2H), 7.96 (m, 1H), 7.76 (m, 1H), 4.91 (bs, 2H), 1.69 (s, 6H), 1.25 (s, 9H). |
| A01M1B02 | $^1$H NMR (400 MHz, DMSO-d$_6$): δ ppm 1.65 (s, 6 H), 2.0 (m, 4 H) 3.79 (m, 2 H), 4.53 (t, 1 H), 4.83 (m, 2 H), 7.3 (m, 2 H), 8.05 (m, 2 H), 10.92 (s, 1 H), 12.45 (s, 1 H). |
| A48M1B02 | $^1$H NMR (400 MHz, DMSO-d$_6$): δ ppm 1.59 (s, 3 H) 1.60 (s, 3 H) 1.86 (m, 4 H) 3.70 (m, 2 H) 3.76 (s, 2 H) 4.44 (t, J = 6.52 Hz, 1 H) 4.55 (d, J = 12.44 Hz, 1 H) 4.72 (d, J = 12.56 Hz, 1 H) 7.46 (m, 3 H) 7.78 (s, 1 H) 7.86 (m, 3 H) 10.74 (s, 1 H) 12.32 (s, 1 H) |
| A03M1B14 | $^1$H NMR (400 MHz, DMSO-d$_6$): δ ppm 1.7 (s, 6 H) 2.0 (m, 4 H) 3.8 (m, 2 H) 4.6 (t, J = 6.6 Hz, 1 H) 4.7 (d, J = 12.4 Hz, 1 H) 4.9 (d, J = 12.4 Hz, 1 H) 7.6 (ddd, J = 10.5, 8.5, 8.4 Hz, 1 H) 7.9 (m, 1 H) 8.1 (m, 1 H) 11.1 (s, 1 H) 12.5 (s, 1 H)<br>α$_D$ + 24.5 (c = 1.08, MeOH) |
| A12M1B14 | $^1$H NMR (400 MHz, DMSO-d$_6$): δ ppm 0.92 (d, J = 6.58 Hz, 6 H) 1.65 (d, J = 2.44 Hz, 6 H) 1.96 (m, 6 H) 2.16 (d, J = 6.95 Hz, 2 H) 3.80 (m, 2 H) 4.53 (dd, J = 6.95, 6.10 Hz, 1 H) 4.68 (m, 2 H) 10.37 (s, 1 H) 12.30 (s, 1 H)<br>α$_D$ + 24.0 (c = 1.00, MeOH) |
| A13M1B14 | $^1$H NMR (400 MHz, DMSO-d$_6$): δ ppm 1.64 (s, 6 H) 1.97 (m, 10 H) 3.25 (m, 1 H) 3.80 (m, 2 H) 4.55 (t, J = 6.58 Hz, 1 H) 4.70 (m, 2 H) 10.26 (s, 1 H) 12.28 (s, 1 H)<br>α$_D$ + 24.7 (c = 1.09, MeOH) |
| A32M1B14.HCl | $^1$H NMR (400 MHz, DMSO-d$_6$): (mixture of two conformers) δ ppm 1.68 (s, 12 H) 1.8-2.1 (m, 10 H) 2.30 (d, J = 14.0 Hz, 2 H) 2.80 (d, J = 5.0 Hz, 3H) 2.83 (d, J = 5.0 Hz, 3 H) 3.1-3.3 (m, 4 H) 3.45 (m, 2 H) 3.52 (d, J = 14.0 Hz, 2 H) 3.7-3.8 (m, 4 H) 4.56 (dd, J = 7.0, 6.0 Hz, 2 H) 4.66 (m, 1 H) 4.71, 4.88 (2 d, J = 13 Hz, 4 H) 4.87 (m, 1H) 7.21 (dd, J = 8.0, 2.3 Hz, 1H) 7.26 (dd, J = 8.8, 2.3 Hz, 1H) 7.46 (m, 2 H) 7.5-7.7 (m, 4 H) 9.89 (bs, 2 H) 10.94 (s, 2 H) 12-13 (bs, 2 H).<br>α$_D$ + 17.4 (c = 1.02, MeOH) |
| A33M1B14•2HCl | $^1$H NMR (400 MHz, DMSO-d$_6$): δ ppm 1.7 (s, 3 H) 1.7 (s, 3 H) 2.0 (m, 4 H) 2.8 (s, 3 H) 3.7 (m, 10 H) 3.8 (m, 2 H) 4.6 (dd, J = 7.3, 5.9 Hz, 1 H) 4.7 (d, J = 12.4 Hz, 1 H) 4.9 (d, J = 12.4 Hz, 1 H) 7.6 (d, J = 7.3 Hz, 2 H) 8.0 (d, J = 8.2 Hz, 2 H) 10.3 (s, 1 H) 11.0 (s, 1 H)<br>α$_D$ + 14.7 (c = 1.09, MeOH) |
| A31M1B14 | $^1$H NMR (400 MHz, DMSO-d$_6$): δ ppm 1.7 (s, 6 H) 2.1 (m, 8 H) 2.8 (m, 3 H) 3.3 (m, 4 H) 3.8 (m, 2 H) 4.6 (dd, J = 7.2, 6.1 Hz, 1 H) 4.7 (m, 1 H) 4.7 (d, J = 12.6 Hz, 1 H) 4.9 (d, J = 12.6 Hz, 1 H) 7.1 (m, 2 H) 8.0 (m, 2 H) 9.9 (m, 1 H) 10.8 (s, 1 H) 12.2 (s, 1 H)<br>α$_D$ (as hydrochloride salt) + 17.0 (c = 1.08, MeOH) |
| A01M2B14 | $^1$H NMR (400 MHz, DMSO-d$_6$): δ 12.25 (bs, 1H), 10.98 (bs, 1H), 8.11 (m, 2H), 7.34 (m, 2H), 4.96 (m, 2H), 4.56 (t, 1H), 3.77 |

TABLE III-continued

| | |
|---|---|
| | (m, 2H) 2.24 (m, 2H), 2.03 (m, 2H), 1.87 (m, 2H), 0.93 (s, 2H). $\alpha_D$ + 15.9 (c = 1.06, MeOH) |
| A12M1B21•HCO$_2$H | $^1$H NMR (400 MHz, DMSO-d$_6$): δ ppm 0.9 (d, J = 6.6 Hz, 6 H) 1.2 (s, 3 H) 1.5 (m, 2 H) 1.7 (s, 6 H) 2.2 (m, 12 H) 4.7 (s, 2 H) 8.2 (s, 1 H) 10.4 (s, 1 H) 12.3 (s, 1 H) |
| A01M1B21•HCl | $^1$H NMR (400 MHz, DMSO-d$_6$): (mixture of two conformers) δ ppm 1.29 (s, 3 H) 1.38 (s, 3 H) 1.65 (m, 2 H) 1.70 (s, 3 H) 1.73 (s, 3 H) 1.95 (d, J = 14.0 Hz, 2 H) 2.08 (m, 2 H) 2.46 (d, J = 14.0 Hz, 2 H) 2.74 (d, J = 5.0 Hz, 3 H) 2.79 (d, J = 5.0 Hz, 3 H) 2.87 (m, 2 H) 3.13 (m, 2 H) 3.3-3.5 (m, 4 H) 4.86 (s, 4 H) 7.35 (t, J = 8.9 Hz, 4 H) 8.09 (dd, J = 8.9, 5.5 Hz, 4H) 9.5 (bs, 1 H) 9.7 (bs, 1 H) 11.01 (s, 1 H) 11.03 (s, 1 H) 12-13 (bs, 2 H). |
| A01M1B22•HCl | $^1$H NMR (400 MHz, DMSO-d$_6$): δ ppm 1.69 (s, 6 H) 2.16 (m, 6 H) 3.32 (m, 6 H) 4.89 (s, 2 H) 7.36 (t, J = 8.66 Hz, 2 H) 8.08 (dd, J = 9.02, 5.49 Hz, 2 H) 9.58 (s, 1 H) 11.01 (s, 1 H) 12.55 (s, 1 H) |
| A48M1B43 | $^1$H NMR (400 MHz, DMSO-d$_6$): δ ppm 1.16 (t, J = 7.13 Hz, 3 H) 1.57 (s, 6 H) 3.76 (s, 2 H) 4.00 (q, J = 7.07 Hz, 2 H) 4.38 (s, 2 H) 7.48 (m, 3 H) 7.79 (s, 1 H) 7.87 (m, 3 H) 10.73 (s, 1H) 12.32 (s, 1H) |

EXAMPLE 18

N-{6,6-dimethyl-5-[(1-methylpiperidin-4-yl)carbonyl]-2,4,5,6-tetrahydropyrrolo[3,4-c]pyrazol-3-yl}-4-fluorobenzamide Ethyl 3-[(4-fluorobenzoyl)amino]-6,6-dimethyl-5,6-dihydropyrrolo[3,4-c]pyrazole-1(4H)-carboxylate hydrochloride (0.5 g, 1.3 mmol), in dichloromethane (25 ml), was treated with N,N-diisopropylethylamine (1.13 ml, 6.5 mmol, 5 eq) and TBTU (0.542 g, 1.69 mmol, 1.3 eq), at room temperature for 1 hour, and then 1-methyl-piperidine-4-carboxylic acid hydrochloride (0.29 g, 1.61 mmol, 1.2 eq) was added. The reaction was stirred overnight (TLC: CH$_2$Cl$_2$/MeOH 90/10). The solution was washed with saturated sodium hydrogencarbonate aqueous solution and brine, the organic phase was dried over sodium sulfate and concentrated. The residue was dissolved in methanol (16 ml), treated with TEA (2 ml, 14.3 mmol, 11 eq) and stirred overnight at room temperature. (TLC: CH$_2$Cl$_2$/MeOH/NH$_4$OH 90/10/1). After evaporation, the solid was purified by flash chromatography (eluent: CH$_2$Cl$_2$/MeOH/NH$_4$OH 90/10/2). The solid was treated with diisopropylether and filtered to afford 0.36 g of the title compound in 69% yield.

ESI MS: m/z 400 (MH+);
$^1$H NMR (400 MHz, DMSO-d$_6$): δ 12.48 (bs, 1H), 10.97 (bs, 1H), 8.09 (m, 2H), 7.35 (m, 2H), 4.75 (bs, 2H), 2.87 (m, 2H), 2.40 (m, 1H), 2.24 (s, 3H), 2.05 (m, 2H), 1.67 (m, 10H).

By working in an analogous manner the following compound was prepared:

N-[5-[(1-methylpiperidin-4-yl)carbonyl]-2,4,5,6-tetrahydropyrrolo[3,4-c]pyrazol-6-spirocyclopropan-3-yl]-4-fluorobenzamide ESI MS: m/z 398 (MH+);
$^1$H NMR (400 MHz, DMSO-d$_6$): δ 12.20 (bs, 1H), 11.00 (s, 1H), 8.10 (m, 2H), 7.36 (m, 2H), 4.91 (s, 2H), 2.84 (m, 2H), 2.40 (m, 1H), 2.23 (m, 5H), 2.0 (m, 2H), 1.65 (m, 4H), 0.89 (m, 2H).

By working in analogous manner and by using the proper starting material and any suitable reactant, as per the aforementioned process, additional compounds of formula (Ia) and (Ib) were also prepared, as reported in the following table IV

TABLE IV

| | |
|---|---|
| A01M1B03.HCl | $^1$H NMR (400 MHz, DMSO-d$_6$): δ 11.02 (s, 1H), 9.56 (bs, 1H), 8.11 (m, 2H), 7.36 (m, 2H), 4.80 (bs, 2H), 3.43 (m, 2H), 3.07 (m, 2H) 2.75 (d, 3H), 2.69 (m, 1H), 1.94 (m, 4H), 1.67 (m, 6H). |
| A02M1B03.HCl | $^1$H NMR (400 MHz, DMSO-d6) δ ppm 1.68 (m, 6H) 1.93 (m, 4H) 2.74 (m, 4H) 3.07 (m, 2H) 3.42 (m, 2H) 4.81 (s, 2H) 7.46 (m, 1H) 7.59 (td, J = 7.96, 5.91 Hz, 1H) 7.82 (ddd, J = 10.00, 2.32, 1.59 Hz, 1H) 7.87 (dt, J = 7.90, 1.11 Hz, 1H) 9.49 (s, 1H) 11.09 (s, 1H) |
| A03M1B03.HCl | $^1$H NMR (400 MHz, DMSO-d6) δ ppm 1.69 (m, 6H) 1.93 (m, 4H) 2.74 (m, 4H) 3.02 (m, 2H) 3.34 (m, 2H) 4.79 (s, 2H) 7.40 (m, 1H) 7.53 (m, 1H) 7.60 (m, 1H) 9.48 (s, 1H) 11.11 (s, 1H) |
| A04M1B03 | $^1$H NMR (400 MHz, DMSO-d$_6$): δ 12.48 (bs, 1H), 10.93 (s, 1H), 7.75 (m, 1H), 7.40 (m, 1H), 7.22 (m, 1H), 4.75 (bs, 2H), 2.85 (m, 2H), 2.38 (m, 1H), 2.21 (bs, 3H), 2.01 (m, 2H), 1.67 (m, 10H). |
| A05M1B03.HCl | $^1$H NMR (400 MHz, DMSO-d$_6$): δ 12.6 (bs, 1H), 11.19 (s, 1H), 9.49 (bs, 1H), 7.72 (m, 2H), 7.51 (m, 1H), 4.80 (bs, 2H), 3.46 (m, 2H), 3.06 (m, 2H), 2.76 (bd, 3H), 2.71 (m, 1H), 1.97 (m, 2H), 1.81 (m, 2H), 1.67 (s, 6H). |
| A06M1B03.HCl | $^1$H NMR (400 MHz, DMSO-d$_6$): δ 12.55 (bs, 1H), 11.06 (s, 1H), 9.66 (bs, 1H), 8.02 (m, 2H), 7.63 (m, 2H), 4.81 (s, 2H), 3.4 (m, 2H), 3.01 (m, 2H), 2.75 (bs, 3H), 2.68 (m, 1H), 1.95 (m, 2H), 1.84 (m, 2H), 1.67 (s, 6H). |
| A07M1B03.HCl | $^1$H NMR (400 MHz, DMSO-d$_6$): δ 12.60 (bs, 1H), 11.25 (s, 1H), 9.50 (bs, 1H), 8.19 (d, 2H, J = 7.9 Hz), 7.92 (d, 2H, J = 7.9 Hz), |

TABLE IV-continued

| | |
|---|---|
| | 4.83 (s, 2H), 3.4 (m, 2H), 3.01 (m, 2H), 2.78 (bd, 3H), 2.75 (m, 1H), 1.9 (m, 2H), 1.8 (m, 2H), 1.67 (s, 6H). |
| A09M1B03.2HCl | 1H NMR (400 MHz, DMSO-d6) δ ppm 11.38 (s, 1H), 9.68 (s, 1H), 8.83 (d, J = 6.22 Hz, 2H), 7.98 (d, J = 6.22 Hz, 2H), 4.82 (s, 2H), 3.4 (m, 2H), 3.07 (m, 2H), 2.75 (bd, 3H), 2.69 (m, 1H), 1.90 (m, 4H), 1.69 (s, 6H) |
| A10M1B03.HCl | $^1$H NMR (400 MHz, DMSO-$d_6$): δ 12.52 (bs, 1H), 11.07 (s, 1H), 9.50 (bs, 1H), 8.12 (m, 1H), 7.86 (m, 1H), 7.22 (m, 1H), 4.79 (bs, 2H), 3.42 (m, 2H), 3.08 (m, 2H), 2.76 (m, 4H), 1.94 (m, 2H), 1.82 (m, 2H), 1.67 (s, 6H). |
| A11M1B03.HCl | $^1$H NMR (400 MHz, DMSO-$d_6$): δ 12.41 (bs, 1H), 10.83 (s, 1H), 9.55 (s, 1H), 8.43 (dd, J = 2.80, 1.46 Hz, 1H), 7.67 (dd, J = 5.12, 1.46 Hz, 1H), 7.65 (dd, J = 5.12, 2.80 Hz, 1H), 4.79 (s, 2H), 3.47 (m, 2H), 3.06 (m, 2H), 2.74 (m, 4H), 1.88 (m, 4H), 1.68 (s, 6H). |
| A12M1B03 | $^1$H NMR (400 MHz, DMSO-$d_6$): δ 12.29 (bs, 1H), 10.40 (s, 1H), 4.65 (s, 2H), 2.86 (m, 2H), 2.35 (m, 1H), 2.22 (bs, 3H), 2.17 (d, 2H, J = 7.07 Hz), 2.02 (m, 3H), 1.64 (m, 10H), 0.92 (d, 6H, J = 6.6 Hz). |
| A12M1B03.HCl | $^1$H NMR (400 MHz, DMSO-$d_6$): δ 12.29 (s, 1H), 10.41 (bs, 1H), 9.57 (s, 1H), 4.71 (s, 2H), 3.46 (m, 2H), 3.07 (m, 2H), 2.75 (bd, 3H), 2.69 (m, 1H), 2.17 (d, 2H, J = 6.95 Hz), 2.04 (m, 1H), 1.92 (m, 4H), 1.67 (s, 6H), 0.92 (d, 6H, J = 6.7 Hz). |
| A13M1B03 | $^1$H NMR (400 MHz, DMSO-$d_6$): δ 12.29 (bs, 1H), 10.27 (s, 1H), 4.69 (s, 2H), 3.35 (m, 1H), 2.87 (m, 2H), 2.38 (m, 1H), 2.24 (bs, 3H), 2.20 (m, 6H), 2.07 (m, 2H), 1.63 (m, 10H). |
| A13M1B03.HCl | $^1$H NMR (400 MHz, DMSO-$d_6$): δ 12.34 (bs, 1H), 10.30 (s, 1H), 9.48 (bs, 1H), 4.75 (s, 2H), 3.47 (m, 2H), 3.31 (m, 1H), 3.09 (m, 2H), 2.75 (bd, 3H), 2.70 (m, 1H), 2.23-1.76 (m, 10H), 1.64 (s, 6H). |
| A13M1B03.CH$_3$SO$_3$H | $^1$H NMR (400 MHz, DMSO-$d_6$): δ 12.33 (bs, 1H), 10.31 (s, 1H), 9.21 (bs, 1H), 4.75 (s, 2H), 3.44 (m, 2H), 3.24 (m, 1H), 3.09 (m, 2H), 2.78 (bd, 3H), 2.72 (m, 1H), 2.35 (s, 3H), 2.23-1.72 (m, 10H), 1.64 (s, 6H). |
| A14M1B03 | $^1$H NMR (400 MHz, DMSO-$d_6$): δ 12.30 (bs, 1H), 10.72 (s, 1H), 4.63 (s, 2H), 2.86 (m, 2H), 2.34 (m, 1H), 2.23 (bs, 3H), 2.04 (m, 2H), 1.83 (m, 1H), 1.63 (m, 10H), 0.79 (m, 4H). |
| A16M1B03 | $^1$H NMR (400 MHz, DMSO-$d_6$): δ 12.30 (bs, 1H), 11.10 (s, 1H), 8.13 (d, 2H, J = 7.9 Hz), 7.51 (d, 2H, J = 7.9 Hz), 4.75 (s, 2H), 2.86 (m, 2H), 2.39 (m, 1H), 2.22 (s, 3H), 2.03 (m, 2H), 1.69 (m, 10H). |
| A17M1B03 | $^1$H NMR (400 MHz, DMSO-$d_6$): δ 12.48 (bs, 1H), 10.98 (s, 1H), 7.79 (m, 1H), 7.61 (m, 1H), 7.54 (m, 1H), 7.45 (m, 2H), 7.25 (m, 2H), 7.10 (m, 2H), 4.72 (s, 2H), 2.82 (m, 2H), 2.34 (m, 1H), 2.19 (s, 3H), 1.96 (m, 2H), 1.66 (m, 10H). |
| A19M1B03.HCl | $^1$H NMR (400 MHz, DMSO-$d_6$): δ 10.87 (s, 1H), 9.55 (bs, 1H), 7.93 (dd, J = 1.71, 0.85 Hz, 1H), 7.44 (dd, J = 3.48, 0.79 Hz, 1H), 6.70 (dd, J = 3.48, 1.77 Hz, 1H), 4.77 (bs, 2H), 3.30 (m, 2H), 3.05 (m, 2H), 2.74 (m, 4H), 1.93 (m, 2H), 1.84 (m, 2H), 1.67 (s, 6H). |
| A21M1B03 | $^1$H NMR (400 MHz, DMSO-$d_6$): δ 12.40 (bs, 1H), 11.00 (s, 1H), 8.65 (d, 1H, J = 2.5 Hz), 8.16 (d, 2H, J = 8.3 Hz), 8.01 (d, 2H, J = 8.3 Hz), 7.83 (d, 1H, J = 1.6 Hz), 6.62 (dd, 1H, J = 2.5 Hz), 4.47 (s, 2H), 2.86 (m, 2H), 2.38 (m, 1H), 2.22 (s, 3H), 2.03 (m, 2H), 1.69 (m, 10H). |
| A22M1B03 | $^1$H NMR (400 MHz, DMSO-$d_6$): δ 12.44 (bs, 1H), 11.12 (s, 1H), 8.25 (m, 1H), 8.09 (m, 1H), 8.03 (m, 1H), 7.75 (m, 1H), 7.60 (m, 3H), 4.82 (bs, 2H), 2.84 (m, 2H), 2.38 (m, 1H), 2.19 (s, 3H), 1.98 (m, 2H), 1.70 (m, 10H). |
| A23M1B03 | $^1$H NMR (400 MHz, DMSO-$d_6$): δ 12.51 (bs, 1H), 11.11 (s, 1H), 8.67 (bs, 1H), 8.07 (m, 4H), 7.66 (m, 2H), 4.80 (bs, 2H), 2.86 (m, 2H), 2.38 (m, 1H), 2.22 (s, 3H), 2.02 (m, 2H), 1.69 (m, 10H). |
| A24M1B03 | $^1$H NMR (400 MHz, DMSO-$d_6$): δ 12.11 (bs, 1H), 8.82 (s, 1H), 7.19 (m, 4H), 6.81 (m, 1H), 4.61 (s, 2H), 4.29 (d, 2H, J = 5.80 Hz), 2.85 (m, 2H), 2.33 (m, 1H), 2.30 (s, 3H), 2.21 (s, 3H), 2.03 (m, 2H), 1.63 (m, 10H). |
| A25M1B03 | $^1$H NMR (400 MHz, DMSO-$d_6$): δ 12.08 (bs, 1H), 8.85 (s, 1H), 7.30 (m, 5H), 6.91 (bs, 1H), 4.61 (s, 2H), 4.32 (d, 2H, J = 5.90 Hz), 2.86 (m, 2H), 2.35 (m, 1H), 2.30 (s, 3H), 2.05 (m, 2H), 1.63 (m, 10H). |
| A26M1B03 | $^1$H NMR (400 MHz, DMSO-$d_6$): δ 12.00 (bs, 1H), 8.67 (s, 1H), 6.45 (bs, 1H), 4.59 (s, 2H), 3.06 (m, 2H), 2.83 (m, 2H), 2.34 (m, 1H), 2.19 (s, 3H), 1.96 (m, 2H), 1.65 (m, 4H), 1.62 (s, 6H), 1.43 (m, 2H), 0.88 (t, 3H). |
| A27M1B03 | $^1$H NMR (400 MHz, DMSO-$d_6$): δ 12.25 (bs, 1H), 9.05 (s, 1H), 7.45 (m, 1H), 7.33 (m, 1H), 7.13 (m, 1H), 6.81 (m, 1H), 4.68 (s, 2H), 2.89 (m, 2H), 2.40 (m, 1H), 2.26 (s, 3H), 2.1 (m, 2H), 1.65 (m, 10H). |

TABLE IV-continued

| | |
|---|---|
| A28M1B03.HCl | $^1$H NMR (400 MHz, DMSO-d$_6$): δ 12.13 (bs, 1H), 9.05 (bs, 1H), 4.64 (s, 2H), 3.5-3.2 (m, 8H), 2.75 (m, 4H), 1.94 (m, 2H), 1.82 (m, 2H), 1.63 (m, 12H). |
| A30M01B03 | $^1$H NMR (400 MHz, DMSO-d$_6$): δ 12.48 (bs, 1H), 10.93 (bs, 1H), 8.0 (m, 2H), 7.61 (m, 1H), 7.51 (m, 2H), 4.76 (bs, 2H), 2.86 (m, 2H), 2.38 (m, 1H), 2.23 (bs, 3H), 2.03 (m, 2H), 1.67 (m, 10H). |
| A01M1B04.HCl | $^1$H NMR (400 MHz, DMSO-d$_6$): δ 1.24 (t, J = 7.32 Hz, 3H) 1.69 (s, 6H) 1.98 (m, 4H) 2.78 (m, 1H) 3.09 (dd, J = 7.32, 5.00 Hz, 4H) 3.50 (d, J = 11.71 Hz, 2H) 4.80 (s, 2H) 7.36 (t, J = 8.78 Hz, 2H) 8.09 (m, 2H) 9.30 (s, 1H) 11.01 (s, 1H) 12.56 (s, 1 H). |
| A03M1B04.HCl | $^1$H NMR (400 MHz, DMSO-d$_6$): δ 1.24 (t, J = 7.32 Hz, 3H) 1.69 (s, 6H) 1.91 (m, 4H) 2.77 (m, 1H) 3.31 (m, 6H) 4.80 (s, 2H) 7.61 (m, 1H) 7.91 (m, 1H) 8.07 (m, 1H) 9.24 (s, 1H) 11.11 (s, 1H) 12.59 (s, 1H). |
| A12M01B04.HCl | $^1$H NMR (400 MHz, DMSO-d$_6$): δ 0.92 (d, J = 6.58 Hz, 6H) 1.24 (t, J = 7.26 Hz, 3H) 1.65 (s, 6H) 1.88 (m, 4H) 2.06 (m, 1 H) 2.17 (d, J = 7.07 Hz, 2H) 2.70 (m, 1H) 3.23 (m, 6H) 4.72 (s, 2H) 9.32 (s, 1H) 10.41 (s, 1H) 12.34 (s, 1H). |
| A13M01B04.HCl | $^1$H NMR (400 MHz, DMSO-d$_6$): δ 1.25 (t, J = 7.32 Hz, 3H) 1.65 (s, 6H) 2.03 (m, 10H) 2.77 (m, 1H) 3.28 (m, 7H) 4.75 (s, 2H) 9.31 (s, 1H) 10.30 (s, 1H) 12.35 (s, 1H). |
| A27M01B04.HCl | $^1$H NMR (400 MHz, DMSO-d$_6$): δ 1.24 (t, J = 7.32 Hz, 3H) 1.66 (s, 6H) 1.89 (m, 4H) 2.75 (m, 1H) 3.18 (m, 6H) 4.73 (s, 2H) 6.80 (m, 1H) 7.08 (ddd, J = 8.17, 1.95, 0.73 Hz, 1H) 7.32 (td, J = 8.17, 6.95 Hz, 1H) 7.52 (dt, J = 11.89, 2.35 Hz, 1H) 9.10 (s, 1H) 9.22 (s, 1H) 9.27 (s, 1H) 12.24 (s, 1H) |
| A01M1B05 | $^1$H NMR (400 MHz, DMSO-d$_6$): δ 12.48 (bs, 1H), 10.97 (s, 1H), 8.09 (m, 2H), 7.35 (m, 2H), 4.75 (s, 2H), 3.00 (m, 2H), 2.44 (m, 1H), 2.24 (m, 2H), 1.8-1.5 (m, 5H), 1.67 (s, 6H), 0.38 (m, 4H). |
| A03M1B05.HCl | $^1$H NMR (400 MHz, DMSO-d$_6$): δ 0.82 (m, 2H) 0.99 (s, 2H) 1.68 (s, 6H) 1.91 (m, 4H) 2.79 (m, 1H) 3.38 (m, 5H) 4.81 (s, 2H) 7.62 (m, 1H) 7.92 (ddd, J = 8.72, 4.27, 1.40 Hz, 1H) 8.08 (ddd, J = 11.52, 7.80, 2.13 Hz, 1H) 9.14 (s, 1H) 11.12 (s, 1H) 12.57 (s, 1H) |
| A12M1B05.HCl | $^1$H NMR (400 MHz, DMSO-d$_6$): δ 0.82 (m, 2H) 0.93 (d, J = 6.58 Hz, 6H) 1.00 (s, 2H) 1.65 (s, 6H) 1.90 (m, 4H) 2.06 (m, 1H) 2.17 (d, J = 7.07 Hz, 2H) 2.76 (m, 1H) 3.36 (m, 5H) 4.73 (s, 2H) 9.20 (s, 1H) 10.41 (s, 1H) 12.35 (s, 1H) |
| A13M1B05.HCl | $^1$H NMR (400 MHz, DMSO-d$_6$): δ 0.82 (m, 2H) 1.01 (s, 2H) 1.65 (s, 6H) 2.01 (m, 10H) 2.78 (m, 1H) 3.33 (m, 6H) 4.77 (s, 2H) 9.23 (s, 1H) 10.30 (s, 1H) 12.25 (s, 1H) |
| A27M1B05.HCl | $^1$H NMR (400 MHz, DMSO-d$_6$): δ 0.82 (q, J = 6.87 Hz, 2H) 1.00 (m, 2H) 1.66 (s, 6H) 1.88 (m, 4H) 2.77 (m, 1H) 3.40 (m, 5H) 4.75 (s, 2H) 6.81 (m, 1H) 7.09 (ddd, J = 8.11, 1.95, 0.79 Hz, 1H) 7.32 (td, J = 8.20, 7.01 Hz, 1H) 7.52 (dt, J = 11.77, 2.23 Hz, 1H) 9.10 (s, 1H) 9.17 (m, 1H) 9.21 (s, 1H) 12.99 (s, 1H) |
| A01M1B06.HCl | $^1$H NMR (400 MHz, DMSO-d$_6$): δ 1.68 (s, 6H) 1.80 (m, 4H) 2.81 (m, 1H) 3.01 (m, 2H) 3.38 (m, 2H) 4.78 (s, 2H) 7.36 (t, J = 8.84 Hz, 2H) 8.09 (dd, J = 8.96, 5.43 Hz, 2H) 8.35 (m, 1H) 8.62 (d, J = 9.88 Hz, 1H) 11.00 (s, 1H) 12.52 (s, 1H) |
| A03M1B06.HCl | $^1$H NMR (400 MHz, DMSO-d$_6$): δ 1.68 (s, 6H) 1.83 (m, 4H) 2.80 (m, 1H) 3.00 (m, 2H) 3.37 (m, 2H) 4.78 (s, 2H) 7.61 (m, 1H) 7.92 (m, 1H) 8.07 (ddd, J = 11.49, 7.83, 2.13 Hz, 1H) 8.45 (m, 2H) 11.11 (s, 1H) 12.57 (s, 1H) |
| A04M1B07 | $^1$H NMR (400 MHz, DMSO-d$_6$): δ ppm 1.81 (s, 6H) 2.21 (s, 3 H) 4.51 (s, 2H) 6.96 (d, J = 4.88 Hz, 1H) 7.16 (t, J = 7.68 Hz, 1 H) 7.35 (t, J = 10.97 Hz, 1H) 7.54 (d, J = 5.00 Hz, 1H) 7.69 (m, 1H) 10.88 (s, 1H) 12.56 (s, 1H) |
| A12M1B07 | $^1$H NMR (400 MHz, DMSO-d$_6$): δ 12.37 (bs, 1H), 10.35 (s, 1H), 7.54 (d, 1H, J = 5.0 Hz), 6.96 (d, 1H, J = 5.0 Hz), 4.42 (s, 2H), 2.20 (s, 3H), 2.10 (d, 2H, J = 7.19 Hz), 1.98 (m, 1H), 1.77 (s, 3H), 0.87 (d, 6H, J = 6.47 Hz). |
| A13M1B07 | $^1$H NMR (400 MHz, DMSO-d$_6$): δ ppm 1.74 (m, 1H) 1.77 (s, 6 H) 1.88 (m, 1H) 2.02 (m, 2H) 2.14 (m, 2H) 2.20 (s, 3H) 3.18 (m, 1H) 4.44 (s, 2H) 6.97 (d, J = 5.00 Hz, 1H) 7.55 (d, J = 4.88 Hz, 1H) 10.25 (s, 1H) 12.36 (s, 1H) |
| A14M1B07 | $^1$H NMR (400 MHz, DMSO-d$_6$): δ ppm 0.72 (m, 4H) 1.77 (s, 7 H) 2.18 (s, 3H) 4.39 (s, 2H) 6.95 (d, J = 5.00 Hz, 1H) 7.54 (d, J = 5.00 Hz, 1H) 10.69 (s, 1H) 12.37 (s, 1H) |
| A21M1B07 | $^1$H NMR (400 MHz, DMSO-d$_6$): δ ppm 1.82 (s, 6H) 2.23 (s, 3 H) 4.53 (s, 2H) 6.61 (s, 1H) 6.98 (d, J = 5.00 Hz, 1H) 7.56 (d, J = 4.88 Hz, 1H) 7.82 (s, 1H) 7.96 (m, 2H) 8.10 (d, J = 7.44 Hz, 2H) 8.64 (d, J = 2.44 Hz, 1H) 10.98 (s, 1H) 12.57 (s, 1H) |
| A23M1B07 | $^1$H NMR (400 MHz, DMSO-d$_6$): δ ppm 1.83 (s, 6H) 2.23 (s, 3 H) 4.57 (s, 2H) 6.98 (d, J = 5.00 Hz, 1H) 7.56 (d, J = 4.88 Hz, 1 |

TABLE IV-continued

| | |
|---|---|
| | H) 7.63 (m, 2H) 8.01 (m, 4H) 8.63 (m, 1H) 11.07 (s, 1H) 12.58 (s, 1H) |
| A25M1B07 | ¹H NMR (400 MHz, DMSO-d₆): δ ppm 1.76 (s, 6H) 2.19 (s, 3 H) 4.26 (d, J = 5.85 Hz, 2H) 4.36 (s, 2H) 6.86 (s, 1H) 6.95 (d, J = 4.88 Hz, 1H) 7.22 (s, 3H) 7.32 (m, 2H) 7.53 (d, J = 4.88 Hz, 1H) 8.82 (s, 1H) 12.14 (s, 1H) |
| A27M1B07 | ¹H NMR (400 MHz, DMSO-d₆): δ ppm 1.79 (s, 6H) 2.21 (s, 3 H) 4.44 (s, 2H) 6.78 (m, 1H) 6.97 (d, J = 4.88 Hz, 1H) 7.07 (m, 1H) 7.29 (m, 1H) 7.35 (m, 1H) 7.55 (d, J = 5.00 Hz, 1H) 9.04 (s, 1H) 12.32 (s, 1H) |
| A30M1B07 | ¹H NMR (400 MHz, DMSO-d₆): δ ppm 1.81 (s, 6H) 2.22 (s, 3 H) 4.52 (s, 2H) 6.97 (d, J = 5.00 Hz, 1H) 7.48 (m, 2H) 7.56 (m, 1H) 7.56 (d, J = 5.00 Hz, 1H) 7.95 (d, J = 7.32 Hz, 2H) 10.92 (s, 1H) 12.55 (s, 1H) |
| A48M1B07 | ¹H NMR (400 MHz, DMSO-d₆): δ ppm 1.73 (s, 6H) 2.13 (s, 3 H) 3.71 (s, 2H) 4.35 (s, 2H) 6.89 (d, J = 4.88 Hz, 1H) 7.40 (dd, J = 8.47, 1.65 Hz, 1H) 7.47 (m, 3H) 7.74 (s, 1H) 7.84 (m, 3H) 10.74 (s, 1H) 12.40 (s, 1H) |
| A53M1B07 | ¹H NMR (400 MHz, DMSO-d₆): δ ppm 1.34 (m, 1H) 1.50 (m, 1H) 1.72 (m, 2H) 1.77 (s, 6H) 1.98 (s, 3H) 2.19 (s, 3H) 2.55 (m, 2H) 3.00 (m, 1H) 3.81 (d, J = 12.56 Hz, 1H) 4.35 (d, J = 12.07 Hz, 1H) 4.42 (s, 2H) 6.96 (d, J = 5.00 Hz, 1H) 7.54 (d, J = 4.88 Hz, 1H) 10.45 (s, 1H) 12.40 (s, 1H) |
| A54M1B07 | ¹H NMR (400 MHz, DMSO-d₆): δ ppm 1.82 (s, 6H) 2.22 (s, 3 H) 4.53 (s, 2H) 6.97 (d, J = 5.00 Hz, 1H) 7.56 (d, J = 5.00 Hz, 1 H) 7.72 (m, 1H) 7.91 (m, 1H) 8.24 (m, 2H) 11.24 (s, 1H) 12.62 (s, 1H) |
| A31M01B19.HCl | ¹H NMR (400 MHz, DMSO-d₆): δ 1.80 (s, 6H) 2.07 (m, 4H) 2.81 (m, 3H) 3.14 (m, 4H) 4.75 (m, 1H) 4.99 (s, 2H) 7.13 (m, 2H) 7.20 (dd, J = 4.94, 3.84 Hz, 1H) 7.63 (dd, J = 3.72, 0.79 Hz, 1H) 7.80 (d, J = 5.00 Hz, 1H) 8.02 (m, 2H) 10.07 (m, 1H) 10.86 (s, 1H) 11.99 (s, 1H) |
| A31M1B20.HCl | ¹H NMR (400 MHz, DMSO-d₆): (mixture of two conformers) δ ppm 1.63 (m, 8H) 1.67 (s, 12H) 1.86 (m, 2H) 2.10 (m, 4H) 2.28 (d, J = 14.0 Hz, 2H) 2.68 (m, 2H) 2.79 (d, J = 5.0 Hz, 3 H) 2.81 (d, J = 5.0 Hz, 3H)) 3.1-3.3 (m, 4H) 3.46 (m, 2H) 3.52 (d, J = 14.0 Hz, 2H) 3.90 (m, 8H) 4.68 (m, 1H) 4.76 (m, 4H) 4.89 (m, 1H) 7.11 (d, J = 8.9 Hz, 2H) 7.14 (d, J = 8.9 Hz, 2H) 8.01 (d, J = 8.9 Hz, 2H) 8.03 (d, J = 8.9 Hz, 2 H) 10.02 (bs, 2H) 10.81 (bs, 2H) |
| A33M1B20.HCl | ¹H NMR (400 MHz, DMSO-d₆): δ ppm 1.65 (m, 4H) 1.68 (s, 6 H) 2.70 (m, 1H) 2.81 (s, 3H) 2.9-3-8 (bs, 8H) 3.90 (m, 4 H) 4.06 (bs, 2H) 4.77 (s, 2H) 7.62 (bs, 2H) 8.07 (d, J = 7.8 Hz, 2H) 10.60 (bs, 1H) 11.01 (s, 1H) |
| A12M1B44 | ¹H NMR (400 MHz, DMSO-d₆): δ ppm 0.14 (m, 2H) 0.46 (m, 2H) 0.91 (d, J = 6.58 Hz, 6H) 1.01 (m, 1H) 1.66 (s, 6H) 2.05 (m, 1H) 2.16 (d, J = 7.07 Hz, 2H) 2.24 (d, J = 6.58 Hz, 2H) 4.54 (s, 2H) 10.35 (s, 1H) 12.27 (s, 1H) |
| A13M1B44 | ¹H NMR (400 MHz, DMSO-d₆): δ ppm 0.15 (m, 2H) 0.47 (m, 2H) 1.01 (m, 1H) 1.66 (s, 6H) 1.80 (m, 1H) 1.92 (m, 1H) 2.08 (m, 2H) 2.17 (m, 2H) 2.26 (d, J = 6.46 Hz, 2H) 3.25 (m, 1 H) 4.58 (s, 2H) 10.25 (s, 1H) 12.26 (s, 1H) |
| A14M1B44 | ¹H NMR (400 MHz, DMSO-d₆): δ ppm 0.13 (m, 2H) 0.44 (m, 2H) 0.76 (m, 4H) 0.98 (m, 1H) 1.65 (s, 6H) 1.81 (m, 1H) 2.22 (d, J = 6.58 Hz, 2H) 4.51 (s, 2H) 10.69 (s, 1H) 12.27 (s, 1 H) |
| A25M1B44 | ¹H NMR (400 MHz, DMSO-d₆): δ ppm 0.13 (m, 2H) 0.45 (m, 2H) 0.99 (m, 1H) 1.65 (s, 6H) 2.23 (d, J = 6.46 Hz, 2H) 4.31 (d, J = 5.85 Hz, 2H) 4.49 (s, 2H) 6.89 (s, 1H) 7.25 (m, 1H) 7.28 (d, J = 7.07 Hz, 2H) 7.34 (m, 2H) 8.83 (s, 1H) 12.04 (s, 1 H) |
| A26M1B44 | ¹H NMR (400 MHz, DMSO-d₆): δ ppm 0.14 (m, 2H) 0.47 (m, 2H) 0.87 (t, J = 7.44 Hz, 3H) 1.00 (m, 1H) 1.43 (m, 2H) 1.64 (s, 6H) 2.23 (d, J = 6.58 Hz, 2H) 3.04 (m, 2H) 4.48 (s, 2H) 6.43 (s, 1H) 8.65 (s, 1H) 12.00 (s, 1H) |
| A30M1B44 | ¹H NMR (400 MHz, DMSO-d₆): δ ppm 0.16 (m, 2H) 0.47 (m, 2H) 1.02 (m, 1H) 1.70 (s, 6H) 2.28 (d, J = 6.58 Hz, 2H) 4.65 (s, 2H) 7.51 (m, 2H) 7.59 (m, 1H) 8.01 (d, J = 7.44 Hz, 2H) 10.91 (s, 1H) 12.46 (s, 1H) |
| A54M1B44 | ¹H NMR (400 MHz, DMSO-d₆): δ ppm 0.16 (m, 2H) 0.47 (m, 2H) 1.02 (m, 1H) 1.70 (s, 6H) 2.28 (d, J = 6.58 Hz, 2H) 4.65 (s, 2H) 7.78 (m, 1H) 7.98 (m, 1H) 8.35 (m, 2H) 11.25 (s, 1 H) 12.53 (s, 1H) |
| A04M1B45 | ¹H NMR (400 MHz, DMSO-d₆): δ ppm 0.60 (m, 1H) 0.97 (m, 1H) 1.12 (d, J = 5.97 Hz, 3H) 1.19 (m, 1H) 1.51 (m, 1H) 1.66 (s, 6H) 4.86 (s, 2H) 7.20 (m, 1H) 7.40 (m, 1H) 7.76 (m, 1H) 10.89 (s, 1H) 12.48 (s, 1H) |
| A30M1B45 | ¹H NMR (400 MHz, DMSO-d₆): δ ppm 0.61 (m, 1H) 0.96 (m, 1H) 1.13 (d, J = 5.85 Hz, 3H) 1.20 (m, 1H) 1.53 (m, 1H) |

TABLE IV-continued

| | |
|---|---|
| | 1.67 (s, 6H) 4.87 (s, 2H) 7.51 (m, 2H) 7.60 (m, 1H) 8.02 (d, J = 7.07 Hz, 2H) 10.92 (s, 1H) 12.47 (s, 1H) |
| A54M1B45 | $^1$H NMR (400 MHz, DMSO-d$_6$): δ ppm 0.61 (m, 1H) 0.96 (m, 1H) 1.13 (d, J = 5.85 Hz, 3H) 1.20 (m, 1H) 1.53 (m, 1H) 1.67 (s, 6H) 4.88 (s, 2H) 7.77 (m, 1H) 7.96 (m, 1H) 8.31 (d, 1H) 8.39 (m, 1H) 11.26 (s, 1H) 12.54 (s, 1H) |
| A01M1B47 | $^1$H NMR (400 MHz, DMSO-d$_6$): δ ppm 1.79 (s, 6H) 2.23 (s, 6 H) 3.52 (s, 2H) 4.43 (s, 2H) 7.26 (t, J = 8.78 Hz, 2H) 7.38 (m, 4H) 7.95 (dd, J = 8.84, 5.55 Hz, 2H) 10.90 (s, 1H) 12.50 (s, 1 H) |
| A48M1B47 | $^1$H NMR (400 MHz, DMSO-d$_6$): δ ppm 1.79 (s, 6H) 2.14 (s, 6 H) 3.41 (s, 2H) 3.67 (s, 2H), 4.33 (s, 2H) 7.30 (m, 5H) 7.45 (m, 2H) 7.70 (m, 1H) 7.80 (m, 3H) 10.70 (s, 1H) 12.37 (s, 1 H) |
| A48M1B48 | $^1$H NMR (400 MHz, DMSO-d$_6$): δ ppm 1.76 (s, 6H) 2.18 (s, 3 H) 2.35 (m, 8H), 3.45 (s, 2H) 3.68 (s, 2H) 4.34 (s, 2H) 7.30 (m, 5H) 7.47 (m, 2H) 7.70 (m, 1H) 7.81 (m, 3H) 10.70 (s, 1 H) 12.37 (s, 1H) |
| A01M1B50 | $^1$H NMR (400 MHz, DMSO-d$_6$): δ ppm 0.87 (t, J = 7.44 Hz, 3 H) 1.49 (m, 2H) 1.68 (s, 6H) 2.27 (t, J = 7.38 Hz, 2H) 4.64 (s, 2H) 7.30 (m, 2H) 8.04 (m, 2H) 10.92 (s, 1H) 12.43 (s, 1H) |
| A04M1B50 | $^1$H NMR (400 MHz, DMSO-d$_6$): δ ppm 0.93 (t, J = 7.44 Hz, 3 H) 1.56 (m, 2H) 1.68 (s, 6H) 2.28 (t, J = 7.38 Hz, 2H) 4.68 (s, 2H) 7.22 (m, 1H) 7.40 (m, 1H) 7.75 (m, 1H) 10.88 (s, 1H) 12.47 (s, 1H) |
| A13M1B50 | $^1$H NMR (400 MHz, DMSO-d$_6$): δ ppm 0.93 (t, J = 7.38 Hz, 3 H) 1.55 (m, 2H) 1.64 (s, 6H) 1.80 (m, 1H) 1.93 (m, 1H) 2.07 (m, 2H) 2.18 (m, 2H) 2.27 (t, J = 7.38 Hz, 2H) 3.23 (m, 1H) 4.61 (s, 2H) 10.24 (s, 1H) 12.27 (s, 1H) |
| A14M1B50 | $^1$H NMR (400 MHz, DMSO-d$_6$): δ ppm 0.78 (d, J = 1.95 Hz, 4 H) 0.91 (t, J = 7.38 Hz, 3H) 1.52 (m, 2H) 1.64 (s, 6H) 1.82 (m, 1H) 2.24 (t, J = 7.38 Hz, 2H) 4.55 (s, 2H) 10.70 (s, 1H) 12.27 (s, 1H) |
| A30M1B50 | $^1$H NMR (400 MHz, DMSO-d$_6$): δ ppm 0.94 (t, J = 7.44 Hz, 3 H) 1.57 (m, 2H) 1.69 (s, 6H) 2.30 (t, J = 7.38 Hz, 2H) 4.68 (s, 2H) 7.52 (m, 2H) 7.60 (m, 1H) 8.01 (d, J = 7.80 Hz, 2H) 10.92 (s, 1H) 12.46 (s, 1H) |
| A54M1B50 | $^1$H NMR (400 MHz, DMSO-d$_6$): δ ppm 0.94 (t, J = 7.44 Hz, 3 H) 1.57 (m, 2H) 1.69 (s, 6H) 2.29 (t, J = 7.38 Hz, 2H) 4.70 (s, 2H) 8.31 (m, 4H) 11.25 (s, 1H) 12.53 (s, 1H) |
| A04M1B51 | $^1$H NMR (400 MHz, DMSO-d$_6$): δ ppm 1.68 (s, 6H) 2.03 (m, 2 H) 3.27 (m, 1H) 3.73 (m, 3H) 3.93 (t, J = 8.11 Hz, 1H) 4.76 (m, 2H) 7.21 (m, 1H) 7.39 (m, 1H) 7.74 (m, 1H) 10.90 (s, 1 H) 12.49 (s, 1H) |
| A12M1B51 | $^1$H NMR (400 MHz, DMSO-d$_6$): δ ppm 0.92 (d, J = 6.58 Hz, 6 H) 1.65 (s, 6H) 2.03 (m, 2H) 2.17 (d, J = 7.07 Hz, 2H) 3.21 (m, 1H) 3.73 (m, 3H) 3.91 (t, J = 8.11 Hz, 1H) 4.66 (m, 2H) 10.38 (s, 1H) 12.30 (s, 1H) |
| A13M1B51 | $^1$H NMR (400 MHz, DMSO-d$_6$): δ ppm 1.65 (s, 6H) 1.80 (m, 1 H) 1.96 (m, 3H) 2.07 (m, 2H) 2.19 (m, 2H) 3.26 (m, 2H) 3.74 (m, 3H) 3.92 (t, J = 8.11 Hz, 1H) 4.70 (m, 2H) 10.27 (s, 1 H) 12.29 (s, 1H) |
| A14M1B51 | $^1$H NMR (400 MHz, DMSO-d$_6$): δ ppm 0.78 (m, 4H) 1.64 (s, 6 H) 1.83 (m, 1H) 2.01 (m, 2H) 3.20 (m, 1H) 3.72 (m, 3H) 3.90 (t, J = 8.05 Hz, 1H) 4.64 (m, 2H) 10.71 (s, 1H) 12.29 (s, 1 H) |
| A01M1B52 | $^1$H NMR (400 MHz, DMSO-d$_6$): δ ppm 1.79 (s, 6H) 4.43 (s, 2 H) 7.2-7.95 (m, 9H) 10.90 (s, 1H) 12.50 (s, 1H) |
| A01M1B53 | $^1$H NMR (400 MHz, DMSO-d$_6$): δ ppm 1.82 (s, 6H) 4.43 (s, 2 H) 7.15 (m,H) 7.27 (m,H) 7.34 (m,H) 7.58 (m,H) 7.68 (m, H) 10.93 (s, 1H) 12.62 (s, 1H) |
| A04M1B53 | $^1$H NMR (400 MHz, DMSO-d$_6$): δ ppm 1.82 (s, 6H) 4.43 (s, 2 H) 7.15 (m, 1H) 7.27 (m, 2H) 7.34 (m, 1H) 7.58 (m, 1H) 7.68 (m, 1H) 10.93 (s, 1H) 12.62 (s, 1H) |
| A48M1B53 | $^1$H NMR (400 MHz, DMSO-d$_6$): δ ppm 1.73 (s, 6H) 3.69 (s, 2 H) 4.27 (s, 2H) 7.18 (m, 2H) 7.38 (m, 1H) 7.45 (m, 3H) 7.71 (m, 1H) 7.80 (m, 3H) 10.76 (s, 1H) 12.45 (s, 1H) |
| A54M1B53 | $^1$H NMR (400 MHz, DMSO-d$_6$): δ ppm 1.83 (s, 6H) 4.46 (s, 2 H) 7.28 (m, 2H) 7.59 (m, 1H) 7.71 (m, 1H) 7.92 (m, 1H) 8.21 (m, 1H) 8.29 (m, 1H) 11.26 (s, 1H) 12.68 (s, 1H) |
| A01M1B54 | $^1$H NMR (400 MHz, DMSO-d$_6$): δ ppm 1.81 (s, 6H) 4.43 (s, 2 H) 7.24 (m, 2H) 7.42 (m, 2H) 7.63 (d, J = 8.26 Hz, 2H) 7.87 (d, J = 8.26 Hz, 2H) 7.95 (m, 2H) 10.93 (s, 1H) 12.62 (s, 1H) |
| A48M1B54 | $^1$H NMR (400 MHz, DMSO-d$_6$): δ ppm 1.77 (s, 6H) 3.69 (s, 2 H) 4.33 (s, 2H) 7.32-7.89 (m, 13H) 10.75 (s, 1H) 12.41 (s, 1 H) |
| A01M2B03 | $^1$H NMR (400 MHz, DMSO-d$_6$): δ 12.20 (bs, 1H), 11.00 (s, 1H), 8.10 (m, 2H), 7.36 (m, 2H), 4.91 (s, 2H), 2.84 (m, 2H), 2.4 (m, 1H), 2.23 (m, 5H), 2.0 (m, 2H), 1.65 (m, 4H), 0.89 (m, 2H). |

TABLE IV-continued

| | |
|---|---|
| A02M2B03 | ¹H NMR (400 MHz, DMSO-d₆): δ 12.28 (bs, 1H), 11.08 (s, 1H), 7.88 (m, 2H), 7.51 (m, 2H), 4.92 (s, 2H), 2.84 (m, 2H), 2.41 (m, 1H), 2.25 (m, 5H), 2.05 (m, 2H), 1.68 (m, 4H), 0.91 (m, 2H). |
| A04M2B03 | ¹H NMR (400 MHz, DMSO-d₆): δ 12.24 (bs, 1H), 10.91 (s, 1H), 7.75 (m, 1H), 7.41 (m, 1H), 7.22 (m, 1H), 4.91 (s, 2H), 2.79 (m, 2H), 2.34 (m, 1H), 2.24 (m, 2H), 2.16 (s, 3H), 1.91 (m, 2H), 1.65 (m, 4H), 0.89 (m, 2H). |
| A05M2B03 | ¹H NMR (400 MHz, DMSO-d₆): δ 12.31 (bs, 1H), 11.16 (s, 1H), 7.75 (m, 2H), 7.51 (m, 1H), 4.91 (s, 2H), 2.79 (m, 2H), 2.35 (m, 1H), 2.25 (m, 2H), 2.17 (s, 3H), 1.90 (m, 2H), 1.65 (m, 4H), 0.90 (m, 2H). |
| A06M2B03 | ¹H NMR (400 MHz, DMSO-d₆): δ 12.45 (bs, 1H), 11.06 (s, 1H), 8.03 (m, 2H), 7.61 (m, 2H), 4.91 (s, 2H), 2.84 (m, 2H), 2.41 (m, 1H), 2.21 (m, 5H), 2.0 (m, 2H), 1.65 (m, 4H), 0.89 (m, 2H). |
| A07M2B03 | ¹H NMR (400 MHz, DMSO-d₆): δ 12.30 (bs, 1H), 11.25 (s, 1H), 8.20 (m, 2H), 7.92 (m, 2H), 4.94 (s, 2H), 2.95 (m, 2H), 2.45 (m, 1H), 2.27 (m, 5H), 2.2 (m, 2H), 1.73 (m, 4H), 0.91 (m, 2H). |
| A10M2B03 | ¹H NMR (400 MHz, DMSO-d₆): δ 12.25 (bs, 1H), 11.04 (s, 1H), 8.15 (m, 1H), 7.87 (m, 1H), 7.22 (m, 1H), 4.89 (s, 2H), 2.82 (m, 2H), 2.37 (m, 1H), 2.22 (m, 5H), 1.9 (m, 2H), 1.65 (m, 4H), 0.91 (m, 2H). |
| A11M2B03 | ¹H NMR (400 MHz, DMSO-d₆): δ 12.22 (bs, 1H), 10.81 (s, 1H), 8.45 (m, 1H), 7.69 (m, 2H), 4.90 (s, 2H), 2.82 (m, 2H), 2.37 (m, 1H), 2.24 (m, 2H), 2.18 (m, 3H), 1.93 (m, 2H), 1.66 (m, 4H), 0.89 (m, 2H). |
| A12M2B03 | ¹H NMR (400 MHz, DMSO-d₆): δ 12.06 (bs, 1H), 10.04 (s, 1H), 4.82 (s, 2H), 2.85 (m, 2H), 2.34 (m, 1H), 2.22 (m, 7H), 2.05 (m, 3H), 1.65 (m, 4H), 0.93 (d, 6H, J = 6.58 Hz), 0.85 (m, 2H). |
| A13M2B03 | ¹H NMR (400 MHz, DMSO-d₆): δ 12.04 (bs, 1H), 10.08 (s, 1H), 4.85 (s, 2H), 3.25 (m, 1H), 2.85 (m, 2H), 2.39 (m, 1H), 2.25-1.75 (m, 13H), 1.67 (m, 4H), 0.85 (m, 2H). |
| A19M2B03 | ¹H NMR (400 MHz, DMSO-d₆): δ 12.24 (bs, 1H), 10.84 (s, 1H), 7.94 (m, 1H), 7.51 (m, 1H), 6.70 (m, 1H), 4.88 (s, 2H), 2.85 (m, 2H), 2.40 (m, 1H), 2.22 (m, 5H), 2.01 (m, 2H), 1.67 (m, 4H), 0.89 (m, 2H). |
| A38M2B03 | ¹H NMR (400 MHz, DMSO-d₆): δ 12.21 (bs, 1H), 10.81 (s, 1H), 7.66 (m, 2H), 7.08 (m, 1H), 4.92 (s, 2H), 3.86 (s, 6H), 2.81 (m, 2H), 2.38 (m, 1H), 2.25 (m, 2H), 2.18 (s, 3H), 1.94 (m, 2H), 1.66 (m, 4H), 0.90 (m, 2H). |
| A01M2B04 | ¹H NMR (400 MHz, DMSO-d₆): δ 12.45 (bs, 1H), 11.00 (s, 1H), 8.10 (m, 2H), 7.36 (m, 2H), 4.91 (s, 2H), 2.95 (m, 2H), 2.42 (m, 3H), 2.24 (m, 2H), 1.95 (m, 2H), 1.7 (m, 4H), 1.02 (t, 3H), 0.89 (m, 2H). |
| A02M2B04 | ¹H NMR (400 MHz, DMSO-d₆): δ 12.27 (bs, 1H), 11.07 (s, 1H), 7.85 (m, 2H), 7.68 (m, 1H), 7.45 (m, 1H), 4.91 (s, 2H), 2.90 (m, 2H), 2.34 (m, 3H), 2.25 (m, 2H), 1.92 (m, 2H), 1.65 (m, 4H), 1.0 (t, 3H), 0.90 (m, 2H). |
| A04M2B04 | ¹H NMR (400 MHz, DMSO-d₆): δ 12.23 (bs, 1H), 10.91 (s, 1H), 7.78 (m, 1H), 7.41 (m, 1H), 7.22 (m, 1H), 4.91 (s, 2H), 2.91 (m, 2H), 2.35 (m, 3H), 2.24 (m, 2H), 1.91 (m, 2H), 1.65 (m, 4H), 1.00 (t, 3H), 0.89 (m, 2H). |
| A05M2B04 | ¹H NMR (400 MHz, DMSO-d₆): δ 12.31 (bs, 1H), 11.16 (s, 1H), 7.75 (m, 2H), 7.54 (m, 1H), 4.92 (s, 2H), 2.92 (m, 2H), 2.35 (m, 3H), 2.25 (m, 2H), 1.92 (m, 2H), 1.65 (m, 4H), 1.01 (t, 3H), 0.90 (m, 2H). |
| A06M2B04 | ¹H NMR (400 MHz, DMSO-d₆): δ 12.25 (bs, 1H), 11.05 (s, 1H), 8.03 (m, 2H), 7.6 (m, 2H), 4.91 (s, 2H), 2.90 (m, 2H), 2.45-2.20 (m, 5H), 1.85 (m, 2H), 1.67 (m, 4H), 1.02 (t, 3H), 0.89 (m, 2H). |
| A07M2B04 | ¹H NMR (400 MHz, DMSO-d₆): δ 12.31 (bs, 1H), 11.34 (s, 1H), 8.20 (m, 2H), 7.91 (m, 2H), 4.95 (s, 2H), 3.15-1.5 (m, 13H), 1.06 (t, 3H), 0.91 (m, 2H). |
| A10M2B04 | ¹H NMR (400 MHz, DMSO-d₆): δ 12.25 (bs, 1H), 11.04 (s, 1H), 8.15 (m, 1H), 7.88 (m, 1H), 7.22 (m, 1H), 4.89 (s, 2H), 2.92 (m, 2H), 2.45-2.20 (m, 5H), 1.9 (m, 2H), 1.65 (m, 4H), 1.01 (t, 3H), 0.89 (m, 2H). |
| A11M2B04 | ¹H NMR (400 MHz, DMSO-d₆): δ 12.22 (bs, 1H), 10.81 (s, 1H), 8.46 (m, 1H), 7.69 (m, 2H), 4.90 (s, 2H), 2.92 (m, 2H), 2.34 (m, 3H), 2.25 (m, 2H), 1.92 (m, 2H), 1.65 (m, 4H), 1.01 (t, 3H), 0.89 (m, 2H). |
| A13M2B04 | ¹H NMR (400 MHz, DMSO-d₆): δ 12.04 (bs, 1H), 10.27 (s, 1H), 4.86 (s, 2H), 2.89 (m, 2H), 2.45-1.75 (m, 14H), 1.65 (m, 4H), 1.00 (t, 3H), 0.85 (m, 2H). |

TABLE IV-continued

| | |
|---|---|
| A14M2B04 | ¹H NMR (400 MHz, DMSO-d$_6$): δ 12.05 (bs, 1H), 10.71 (s, 1H), 4.79 (s, 2H), 2.88 (m, 2H), 2.31 (m, 3H), 2.21 (m, 2H), 1.89 (m, 3H), 1.62 (m, 4H), 0.99 (t, 3H), 0.82 (m, 6H). |
| A19M2B04 | ¹H NMR (400 MHz, DMSO-d$_6$): δ 12.24 (bs, 1H), 10.84 (s, 1H), 7.94 (m, 1H), 7.51 (m, 1H), 6.71 (m, 1H), 4.88 (s, 2H), 2.97 (m, 2H), 2.40 (m, 3H), 2.24 (m, 2H), 2.01 (m, 2H), 1.68 (m, 4H), 1.02 (t, 3H), 0.89 (m, 2H). |
| A38M2B04 | ¹H NMR (400 MHz, DMSO-d$_6$): δ 12.20 (bs, 1H), 10.81 (s, 1H), 7.66 (m, 2H), 7.08 (m, 1H), 4.92 (s, 2H), 3.86 (s, 6H), 2.92 (m, 2H), 2.45-2.20 (m, 5H), 1.84 (m, 2H), 1.66 (m, 4H), 1.01 (t, 3H), 0.89 (m, 2H). |
| A01M2B05 | ¹H NMR (400 MHz, DMSO-d$_6$): δ 12.25 (bs, 1H), 11.00 (s, 1H), 8.11 (m, 2H), 7.36 (m, 2H), 4.92 (s, 2H), 3.00 (m, 2H), 2.44 (m, 1H), 2.24 (m, 4H), 1.6 (m, 5H), 0.89 (m, 2H), 0.38 (m, 4H). |
| A06M2B05 | ¹H NMR (400 MHz, DMSO-d$_6$): δ 12.3 (bs, 1H), 11.06 (s, 1H), 8.05 (m, 2H), 7.6 (m, 2H), 4.92 (s, 2H), 3.00 (m, 2H), 2.44 (m, 1H), 2.24 (m, 4H), 1.62 (m, 5H), 0.89 (m, 2H), 0.39 (m, 4H). |
| A07M2B05 | ¹H NMR (400 MHz, DMSO-d$_6$): δ 12.3 (bs, 1H), 11.24 (s, 1H), 8.21 (m, 2H), 7.9 (m, 2H), 4.94 (s, 2H), 2.99 (m, 2H), 2.44 (m, 1H), 2.25 (m, 4H), 1.59 (m, 5H), 0.89 (m, 2H), 0.37 (m, 4H). |
| A01M2B06.HCl | ¹H NMR (400 MHz, DMSO-d$_6$): δ 0.92 (m, 2H), 1.78 (m, 4H) 2.24 (m, 2H), 2.81 (m, 1H) 3.01 (m, 2H) 3.38 (m, 2H) 4.95 (s, 2H) 7.37 (t, J = 8.84 Hz, 2H) 8.10 (dd, J = 8.96, 5.43 Hz, 2 H) 8.35 (m, 1H) 8.65 (d, J = 9.88 Hz, 1H) 11.00 (s, 1H) 12.52 (s, 1H) |
| A01M2B47 | ¹H NMR (400 MHz, DMSO-d$_6$): δ ppm 1.01 (m, 2H) 2.18 (s, 6 H) 2.36 (m, 2H) 3.46 (s, 2H) 4.62 (s, 2H) 7.28 (m, 2H) 7.36 (m, 2H) 7.41 (m, 2H) 7.98 (m, 2H) 10.93 (s, 1H) 12.27 (s, 1 H) |
| A48M2B53 | ¹H NMR (400 MHz, DMSO-d$_6$): δ ppm 1.13 (m, 2H) 2.29 (m, 2H) 3.72 (s, 2H) 4.43 (s, 2H) 7.18 (m, 2H) 7.38 (m, 1H) 7.45 (m, 3H) 7.71 (m, 1H) 7.80 (m, 3H) 10.79 (s, 1H) 12.23 (s, 1H) |

EXAMPLE 19

N-{6,6-dimethyl-5-[(4-methylpiperazin-1-yl)carbonyl]-2,4,5,6-tetrahydro pyrrolo[3,4-c]pyrazol-3-yl}-4-fluorobenzamide To a solution of triphosgene (195 mg, 0.65 mmol, 0.56 eq) in DCM (15 ml) was added a solution of ethyl 3-[(4-fluorobenzoyl)amino]-6,6-dimethyl-5,6-dihydropyrrolo[3,4-c]pyrazole-2(4H)-carboxylate hydrochloride (442 mg, 1.15 mmol) in DCM (30 ml) followed by N,N-diisopropylethylamine (760 μl, 4.31 mmol, 3.75 eq). After 3 hours, a solution of N-methylpiperazine (195 μl, 1.72 mmol, 1.5 eq) and diisopropylethylamine (300 μl, 1.72 mmol, 1.5 eq) in DCM (8 ml) was added. The reaction was stirred overnight at room temperature (TLC:CH$_2$Cl$_2$/MeOH 90/10). The solution was washed with brine, the organic phase was dried over sodium sulfate and concentrated. The residue was dissolved in methanol (16 ml), treated with TEA (1.6 ml, 11.5 mmol, 10 eq) and stirred overnight at room temperature. (TLC: CH$_2$Cl$_2$/MeOH 90/10). After evaporation, the solid was purified by flash chromatography (eluent: CH$_2$Cl$_2$/MeOH 90/10). The solid was treated with diisopropylether and filtered to afford 0.294 g of the title compound in 64% yield.

ESI MS: m/z 401 (MH+);

¹H NMR (400 MHz, DMSO-d$_6$): δ 12.39 (bs, 1H), 10.39 (s, 1H), 8.04 (m, 2H, Ar), 7.31 (m, 2H), 4.53 (bs, 2H), 3.04 (m, 4H), 2.40 (m, 4H), 2.22 (bs, 3H), 1.60 (bs, 6H).

By working in an analogous manner the following compounds were prepared:

N-[5-[(4-methylpiperazin-1-yl)carbonyl]-2,4,5,6-tetrahydropyrrolo[3,4-c]pyrazol-6-spirocyclopropan-3-yl]-4-fluorobenzamide ESI MS: m/z 399 (MH+);

¹H NMR (400 MHz, DMSO-d$_6$): δ 12.19 (bs, 1H), 10.95 (s, 1H), 8.09 (m, 2H), 7.35 (m, 2H), 4.70 (bs, 2H), 3.18 (m, 4H), 2.34 (m, 7H), 1.92 (m, 2H), 0.97 (m, 2H).

EXAMPLE 20

4-Chloro-N-[6,6-dimethyl-5-(4-pyrrolidin-1-ylmethyl-piperidine-1-carbonyl)-1,4,5,6-tetrahydro-pyrrolo[3,4-c]pyrazol-3-yl]-benzamide, hydrochloride A mixture of N-[5-(4-aminomethyl-piperidine-1-carbonyl)-6,6-dimethyl-2,4,5,6-tetrahydro-pyrrolo[3,4-c]pyrazol-3-yl]-4-chloro-benzamide (310 mg, 0.7 mmoles), 1,4-dibromobutane (92 μl, 0.7 mmoles) and NaHCO$_3$ (600 mg, 7 mmoles) in absolute ethanol (15 ml) was heated at 150° C. for 15 minutes in a microwave oven. After cooling, the solution was evaporated. The residue was taken up with dichloromethane/MeOH (90:10) and water, the suspension obtained filtered and the organic layer was evaporated to dryness. The residue was purified by flash chromatography with dichloromethane/MeOH/30% NH$_4$OH aq (95/5/0.5). The product was obtained in 20% yield (71 mg).

The compound was dissolved in methanol (3 ml), a solution of 4N HCl in dioxane (40 μl, 0.16 mmoles) was added and then the solution was evaporated. The solid obtained was triturated in ether to give the title hydrochloride salt as a white powder.

ESI MS: m/z 485 (MH+);

1H NMR (400 MHz, DMSO-D6) δ ppm 1.24 (m, 2H) 1.63 (s, 6H) 1.92 (m, 7H) 2.67 (t, J=11.83 Hz, 2H) 3.01 (m, 2H) 3.09 (t, J=6.46 Hz, 2H) 3.47 (m, 4H) 4.56 (s, 2H) 7.59 (d, J=8.54 Hz, 2H) 8.01 (d, J=8.66 Hz, 2H) 9.49 (s, 1H) 11.02 (s, 1H) 12.50 (s, 1H)

By working in analogous manner and by using the proper starting material and any suitable reactant, as per the aforementioned process, additional compounds of formula (Ia) and (Ib) were also prepared, as reported in the following table V.

TABLE V

| | |
|---|---|
| A03M1B08.HCl | $^1$H NMR (400 MHz, DMSO-$d_6$): δ 1.65 (d, J = 9.15 Hz, 6H) 2.84 (d, J = 3.17 Hz, 3H) 3.06 (s, 4H) 3.58 (s, 4H) 4.62 (s, 2H) 7.61 (m, 1H) 7.91 (m, 1H) 8.07 (m, 1H) 9.98 (s, 1H) 11.08 (s, 1H) 12.61 (s, 1H) |
| A04M1B08 | $^1$H NMR (400 MHz, DMSO-$d_6$): δ 12.44 (bs, 1H), 10.85 (s, 1H), 7.74 (m, 1H), 7.18 (m, 1H), 7.20 (s, 1H), 4.59 (bs, 2H), 3.06 (m, 4H), 2.38 (m, 4H), 2.22 (bs, 3H), 1.64 (bs, 6H). |
| A06M1B08 | $^1$H NMR (400 MHz, DMSO-$d_6$): δ 12.46 (bs, 1H), 10.99 (s, 1H), 8.01 (m, 2H), 7.59 (m, 2H), 4.59 (bs, 2H), 3.07 (m, 4H), 2.40 (m, 4H), 2.25 (bs, 3H), 1.64 (bs, 6H). |
| A07M1B08 | $^1$H NMR (400 MHz, DMSO-$d_6$): δ 12.49 (bs, 1H), 11.16 (s, 1H), 8.19 (d, 2H, J = 7.80 Hz), 7.88 (d, 2H, J = 7.80 Hz), 4.60 (s, 2H), 3.06 (m, 4H), 2.38 (m, 4H), 2.22 (s, 3H), 1.64 (bs, 6H). |
| A12M1B08 | $^1$H NMR (400 MHz, DMSO-$d_6$): δ 12.24 (bs, 1H), 10.32 (s, 1H), 4.47 (s, 2H), 3.03 (m, 4H), 2.34 (m, 4H), 2.20 (s, 3H), 2.15 (d, 2H, J = 7.20 Hz), 2.05 (m, 1H), 1.59 (s, 6H), 0.92 (d, 6H, J = 6.59 Hz). |
| A13M1B08 | $^1$H NMR (400 MHz, DMSO-$d_6$): δ 12.23 (bs, 1H), 10.22 (s, 1H), 4.50 (bs, 2H), 3.32 (m, 1H), 3.04 (m, 4H), 2.35 (m, 4H), 2.21 (s, 3H), 1.91-1.8 (m, 6H), 1.59 (bs, 6H). |
| A14M1B08 | $^1$H NMR (400 MHz, DMSO-$d_6$): δ 12.23 (bs, 1H), 10.66 (s, 1H), 4.44 (bs, 2H), 3.02 (m, 4H), 2.33 (m, 4H), 2.19 (s, 3H), 1.82 (m, 1H), 1.59 (bs, 6H), 0.78 (m, 4H). |
| A16M1B08 | $^1$H NMR (400 MHz, DMSO-$d_6$): δ 12.46 (bs, 1H), 11.04 (s, 1H), 8.12 (m, 2H), 7.51 (m, 2H), 4.57 (bs, 2H), 3.06 (m, 4H), 2.36 (m, 4H), 2.20 (s, 3H), 1.64 (bs, 6H). |
| A17M1B08 | $^1$H NMR (400 MHz, DMSO-$d_6$): δ 12.44 (bs, 1H), 10.94 (s, 1H), 7.78 (m, 1H), 7.61 (bs, 1H), 7.51 (m, 1H), 7.45 (m, 2H), 7.20 (m, 2H), 7.09 (m, 2H), 4.55 (bs, 2H), 3.06 (m, 4H), 2.40 (m, 4H), 2.24 (bs, 3H), 1.63 (bs, 6H). |
| A18M1B08 | $^1$H NMR (400 MHz, DMSO-$d_6$): δ 12.44 (bs, 1H), 10.99 (s, 1H), 7.96 (m, 2H), 7.47-7.33 (m, 7H), 4.55 (bs, 2H), 3.03 (m, 4H), 2.52 (m, 4H), 2.28 (bs, 3H), 1.63 (bs, 6H). |
| A21M1B08 | $^1$H NMR (400 MHz, DMSO-$d_6$): δ 12.44 (bs, 1H), 10.95 (bs, 2H), 8.66 (m, 1H), 8.14 (m, 2H), 8.00 (m, 2H), 7.83 (m, 1H), 6.82 (m, 1H), 4.59 (s, 2H), 3.06 (m, 4H), 2.36 (m, 4H), 2.21 (s, 3H), 1.64 (bs, 6H). |
| A22M1B08 | $^1$H NMR (400 MHz, DMSO-$d_6$): δ 12.41 (bs, 1H), 11.06 (bs, 1H), 8.50-7.60 (m, 7H), 4.64 (s, 2H), 3.07 (m, 4H), 2.35 (m, 4H), 2.18 (s, 3H), 1.66 (bs, 6H). |
| A23M1B08 | $^1$H NMR (400 MHz, DMSO-$d_6$): δ 12.45 (bs, 1H), 11.05 (bs, 1H), 8.66 (bs, 1H), 7.07 (m, 4H), 7.65 (m, 2H), 4.62 (s, 2H), 3.07 (m, 4H), 2.37 (m, 4H), 2.21 (s, 3H), 1.65 (bs, 6H). |
| A24M1B08 | $^1$H NMR (400 MHz, DMSO-$d_6$): δ 12.02 (bs, 1H), 8.80 (s, 1H), 7.19 (m, 4H), 6.90 (bs, 1H), 4.42 (s, 2H), 4.31 (d, 2H J = 5.73 Hz), 3.02 (m, 4H), 2.34 (m, 4H), 2.30 (s, 3H), 2.20 (s, 3H), 1.59 (s, 6H). |
| A25M1B08 | $^1$H NMR (400 MHz, DMSO-$d_6$): δ 12.02 (bs, 1H), 8.83 (s, 1H), 7.31 (m, 5H), 6.99 (bs, 1H), 4.42 (s, 2H), 4.33 (d, 2H J = 5.85 Hz), 3.02 (m, 4H), 2.34 (m, 4H), 2.19 (s, 3H), 1.59 (s, 6H). |
| A26M1B08 | $^1$H NMR (400 MHz, DMSO-$d_6$): δ 12.00 (bs, 1H), 8.65 (s, 1H), 6.54 (m, 1H), 4.41 (s, 2H), 3.02 (m, 6H), 2.34 (m, 4H), 2.20 (s, 3H), 1.58 (s, 6H), 1.43 (m, 2H), 0.88 (t, 3H). |
| A27M1B08 | $^1$H NMR (400 MHz, DMSO-$d_6$): δ 12.22 (bs, 1H), 9.16 (s, 2H), 7.46 (m, 1H), 7.33 (m, 1H), 7.13 (m, 1H), 6.80 (m, 1H), 6.99 (bs, 1H), 4.48 (s, 2H), 3.05 (m, 4H), 2.35 (m, 4H), 2.20 (s, 3H), 1.61 (s, 6H). |
| A01M1B09 | $^1$H NMR (400 MHz, DMSO-$d_6$): δ 12.37 (bs, 1H), 10.88 (s, 1H), 8.04 (m, 2H), 7.31 (m, 2H), 4.51 (bs, 2H), 2.97 (m, 4H), 1.59 (bs, 6H), 1.50 (m, 6H). |
| A06M1B09 | $^1$H NMR (400 MHz, DMSO-$d_6$): δ 12.44 (bs, 1H), 10.98 (s, 1H), 8.01 (d, 2H, J = 8.3 Hz), 7.58 (d, 2H, J = 8.3 Hz), 4.57 (bs, 2H), 3.00 (m, 4H), 1.63 (bs, 6H), 1.54 (m, 6H). |
| A01M1B10 | $^1$H NMR (400 MHz, DMSO-$d_6$): δ 12.41 (bs, 1H), 10.89 (s, 1H), 8.04 (m, 2H), 7.30 (m, 2H), 4.56 (bs, 2H), 3.59 (m, 4H), 3.01 (m, 4H), 1.61 (bs, 6H). |
| A01M1B11 | $^1$H NMR (400 MHz, DMSO-$d_6$): δ 12.52 (bs, 1H), 10.91 (s, 1H), 8.07 (m, 2H), 7.35 (m, 2H), 4.54 (bs, 2H), 3.33 (m, 2H), 2.63 (m, 2H), 1.63 (m, 8H), 1.49 (m, 1H), 1.15 (m, 2H), 0.94 (d, 3H, J = 6.5 Hz). |
| A13M1B11 | $^1$H NMR (400 MHz, DMSO-$d_6$): δ 12.23 (bs, 1H), 10.19 (s, 1H), 4.50 (s, 2H), 3.33 (m, 3H), 2.62 (m, 2H), 2.4-1.4 (m, 15H), 1.15 (m, 2H), 0.95 (d, 3H, J = 6.58 Hz). |
| A14M1B11 | $^1$H NMR (400 MHz, DMSO-$d_6$): δ 12.23 (bs, 1H), 10.63 (s, 1H), 4.43 (s, 2H), 3.33 (m, 2H), 2.61 (m, 2H), 1.9-1.4 (m, 10H), 1.11 (m, 2H), 0.95 (d, 3H, J = 6.58 Hz), 0.77 (m, 4H). |
| A14M1B12 | $^1$H NMR (400 MHz, DMSO-$d_6$): δ 12.23 (bs, 1H), 10.64 (s, 1H), 4.43 (s, 3H), 3.33 (m, 4H), 2.60 (m, 2H), 1.59 (m, 10H), 1.11 (m, 2H), 0.78 (m, 4H). |

TABLE V-continued

| | |
|---|---|
| A01M1B13 | $^1$H NMR (400 MHz, DMSO-d$_6$): δ 12.42 (bs, 1H), 10.91 (s, 1H), 8.08 (m, 2H), 7.33 (m, 2H), 4.56 (bs, 2H), 4.35 (bs, 1H), 3.46 (m, 4H), 2.65 (m, 2H), 1.75-1.05 (m, 13H). |
| A02M2B08 | $^1$H NMR (400 MHz, DMSO-d$_6$): δ 12.00 (bs, 1H), 11.02 (s, 1H), 7.86 (m, 2H), 7.57 (m, 2H), 4.70 (bs, 2H), 3.14 (m, 4H), 2.40 (m, 4H), 2.25 (bs, 3H), 1.91 (m, 2H), 0.97 (m, 2H). |
| A04M2B08 | $^1$H NMR (400 MHz, DMSO-d$_6$): δ 12.16 (bs, 1H), 10.84 (s, 1H), 7.76 (m, 3H), 4.69 (bs, 2H), 3.12 (m, 4H), 2.35 (m, 4H), 2.21 (bs, 3H), 1.90 (m, 2H), 0.97 (m, 2H). |
| A06M2B08 | $^1$H NMR (400 MHz, DMSO-d$_6$): δ 12.20 (bs, 1H), 11.00 (s, 1H), 8.02 (m, 2H), 7.59 (m, 2H), 4.70 (bs, 2H), 3.15 (m, 4H), 2.51 (m, 4H), 2.29 (bs, 3H), 1.92 (m, 2H), 0.89 (m, 2H). |
| A07M2B08 | $^1$H NMR (400 MHz, DMSO-d$_6$): δ 12.24 (bs, 1H), 11.17 (s, 1H), 8.19 (m, 2H), 7.89 (m, 2H), 4.72 (bs, 2H), 3.14 (m, 4H), 2.41 (m, 4H), 2.26 (bs, 3H), 1.92 (m, 2H), 0.98 (m, 2H). |
| A10M2B08 | $^1$H NMR (400 MHz, DMSO-d$_6$): δ 12.18 (bs, 1H), 10.98 (s, 1H), 8.11 (m, 1H), 7.87 (m, 1H), 7.21 (m, 1H), 4.66 (bs, 2H), 3.13 (m, 4H), 2.37 (m, 4H), 2.23 (bs, 3H), 1.91 (m, 2H), 0.97 (m, 2H). |
| A14M2B08 | $^1$H NMR (400 MHz, DMSO-d$_6$): δ 11.98 (bs, 1H), 10.66 (s, 1H), 4.56 (bs, 2H), 3.10 (m, 4H), 2.34 (m, 4H), 2.21 (bs, 3H), 1.87 (m, 2H), 1.86 (m, 1H), 0.92 (m, 2H), 0.82 (m, 4H). |
| A17M2B08 | $^1$H NMR (400 MHz, DMSO-d$_6$): δ 12.17 (bs, 1H), 10.95 (s, 1H), 7.79 (m, 1H), 7.62 (bs, 1H), 7.51 (m, 1H), 7.45 (m, 2H), 7.27 (m, 1H), 7.20 (m, 1H), 7.09 (m, 2H), 4.66 (bs, 2H), 3.12 (m, 4H), 2.35 (m, 4H), 2.21 (s, 3H), 1.90 (m, 2H), 0.98 (m, 2H). |
| A18M2B08 | $^1$H NMR (400 MHz, DMSO-d$_6$): δ 12.17 (bs, 1H), 11.00 (s, 1H), 7.97 (bs, 1H), 7.94 (m, 1H), 7.42 (m, 7H), 4.67 (bs, 2H), 3.11 (m, 4H), 2.32 (m, 4H), 2.20 (s, 3H), 1.90 (m, 2H), 0.98 (m, 2H). |
| A19M2B08 | $^1$H NMR (400 MHz, DMSO-d$_6$): δ 12.17 (bs, 1H), 10.77 (s, 1H), 7.92 (bs, 1H), 7.49 (m, 1H), 6.69 (m, 1H), 4.66 (bs, 2H), 3.12 (m, 4H), 2.37 (m, 4H), 2.23 (s, 3H), 1.90 (m, 2H), 0.96 (m, 2H). |
| A01M2B09 | $^1$H NMR (400 MHz, DMSO-d$_6$): δ 12.13 (bs, 1H), 10.93 (s, 1H), 8.09 (m, 2H), 7.36 (m, 2H), 4.65 (bs, 2H), 3.08 (m, 4H), 1.87 (m, 2H), 1.53 (m, 6H), 0.96 (m, 2H). |
| A01M2B10 | $^1$H NMR (400 MHz, DMSO-d$_6$): δ 12.10 (bs, 1H), 10.95 (s, 1H), 8.09 (m, 2H), 7.34 (m, 2H), 4.70 (bs, 2H), 3.62 (m, 4H), 3.12 (m, 4H), 1.93 (m, 2H), 0.96 (m, 2H). |
| A01M2B11 | $^1$H NMR (400 MHz, DMSO-d$_6$): δ 12.15 (bs, 1H), 10.93 (s, 1H), 8.09 (m, 2H), 7.36 (m, 2H), 4.65 (bs, 2H), 3.54 (m, 2H), 2.65 (m, 2H), 1.87 (m, 2H), 1.61 (m, 2H), 1.50 (m, 1H), 1.12 (m, 2H), 0.94 (m, 5H). |
| A01M2B12 | $^1$H NMR (400 MHz, DMSO-d$_6$): δ 11.88 (bs, 1H), 10.93 (s, 1H), 8.08 (m, 2H), 7.36 (m, 2H), 4.66 (bs, 2H), 3.54 (m, 2H), 3.45 (m, 3H), 2.65 (m, 2H), 1.87 (m, 2H), 1.66 (m, 2H), 1.50 (m, 1H), 1.12 (m, 2H), 0.94 (m, 2H). |
| A01M2B13 | $^1$H NMR (400 MHz, DMSO-d$_6$): δ 11.33 (bs, 1H), 10.93 (s, 1H), 8.08 (m, 2H), 7.36 (m, 2H), 4.65 (bs, 2H), 3.54 (m, 2H), 3.45 (m, 3H), 2.65 (m, 2H), 1.87 (m, 2H), 1.66 (m, 2H), 1.50 (m, 1H), 1.40 (m, 2H), 1.12 (m, 2H), 0.95 (m, 2H). |
| A48M1B08 | $^1$H NMR (400 MHz, DMSO-d$_6$): δ 1.55 (s, 6H), 2.19 (s, 3H), 2.35 (m, 4H), 2.98 (m, 4H), 3.75 (s, 2H), 4.44 (s, 2H), 7.5 (m, 3H), 7.75 (s, 1H), .7.85 (m, 3H), 10.7 (bs, 1H), 12.5 (s, 1H). |
| A30M1B08 | $^1$H NMR (400 MHz, DMSO-d$_6$): δ 1.63 (s, 6H), 2.20 (s, 3H), 2.36 (m, 4H), 3.06 (m, 4H), 4.57 (s, 2H), 7.51 (m, 2H), 7.60 (m, 1H), 7.99 (m, 2H), 10.89 (bs, 1H), 12.42 (bs, 1H). |
| A38M2B08 | $^1$H NMR (400 MHz, DMSO-d$_6$): δ 0.96 (m, 2H), 1.91 (bs, 2H), 2.23 (bs, 3H), 2.37 (bs, 4H), 3.13 (bs, 4H), 3.86 (s, 6H), 4.69 (s, 2H), 7.07 (s, 1H), 7.66 (bs, 2H), 10.76 (s, 1H), 12.14 (bs, 1H). |
| A54M1B08 | $^1$H NMR (400 MHz, DMSO-d$_6$): δ 1.64 (s, 6H), 2.20 (s, 3H), 2.36 (m, 4H), 3.06 (m, 4H), 4.59 (s, 2H), 7.77 (m, 1H), 7.96 (m, 1H), 8.3 (m, 1H), 8.36 (s, 1H), 11.23 (s, 1H), 12.50 (bs, 1H). |
| A04M1B12 | $^1$H NMR (400 MHz, DMSO-d$_6$): δ 1.16 (m, 2H), 1.4-1.75 (m, 9H), 2.62 (m, 2H), 3.33 (m, 4H), 4.46 (t, 1H), 4.56 (bs, 2H), 7.2 (m, 2H), 7.75 (m, 1H), 10.84 (s, 1H), 12.43 (s, 1H). |
| A01M1B12 | $^1$H NMR (400 MHz, DMSO-d$_6$): δ 1.17 (m, 2H), 1.51 (m, 1H), 1.63 (s, 6H), 1.66 (m, 2H), 2.62 (m, 2H), 3.32 (m, 4H), 4.54 (bs, 2H), 7.35 (m, 2H), 8.07 (m, 2H), 10.92 (s, 1H), 12.4 (bs, 1H). |
| A48M1B13 | $^1$H NMR (400 MHz, DMSO-d$_6$): δ 12.25 (bs, 1H), 10.7 (s, 1H), 7.85 (m, 3H), 7.8 (s, 1H), 7.45 (m, 3H), 4.4 (bs, 2H), 4.3 (t, 1H), 3.75 (s, 2H), 3.44 (m, 4H), 2.65 (m, 2H), 1.70 (m, 2H), 1.67 (s, 6H), 1.52 (m, 1H), 1.39 (m, 2H), 1.15 (m, 2H). |
| A30M1B13 | $^1$H NMR (400 MHz, DMSO-d$_6$): δ 7.99 (m, 2H), 7.59 (m, 1H), 7.51 (m, 2H), 4.56 (bs, 2H), 4.35 (t, 1H), 3.46 (m, 4H), 2.97 (m, 2H), 1.45-1.95 (m, 11H), 1.17 (m, 2H). |
| A23M1B13 | $^1$H NMR (400 MHz, DMSO-d$_6$): δ 12.45 (bs, 1H), 11.02 (s, 1H), 8.67 (s, 1H), 8.07 (m, 4H), 7.65 (m, 2H), 4.61 (bs, 2H), 4.35 (t, 1H), 3.46 (m, 4H), 2.63 (m, 2H), 1.45-1.85 (m, 8H), 1.52 (m, 1H), 1.42 (m, 2H), 1.18 (m, 2H). |
| A14M1B13 | $^1$H NMR (400 MHz, DMSO-d$_6$): δ 12.23 (bs, 1H), 10.64 (s, 1H), 4.42 (bs, 2H), 4.35 (t, 1H), 3.47 (m, 2H), 3.33 (m, 2H), 2.56 (m, 2H), |

TABLE V-continued

| | |
|---|---|
| | 1.82 (m, 1H), 1.65 (m, 2H), 1.59 (s, 6H), 1.52 (m, 1H), 1.4 (m, 2H), 1.12 (m, 2H), 0.78 (m, 4H). |
| A04M1B13 | $^1$H NMR (400 MHz, DMSO-d$_6$): δ 12.43 (bs, 1H), 10.84 (s, 1H), 7.76 (m, 1H), 7.38 (m, 1H), 7.2 (m, 1H), 4.56 (bs, 2H), 4.34 (t, 1H), 3.45 (m, 2H), 3.33 (m, 2H), 2.56 (m, 2H), 1.75-1.55 (m, 8H), 1.53 (m, 1H), 1.40 (m, 2H), 1.15 (m, 2H). |
| A16M1B13 | $^1$H NMR (400 MHz, DMSO-d$_6$): δ 12.45 (bs, 1H), 11.02 (s, 1H), 8.12 (m, 2H), 7.51 (m, 2H), 4.56 (bs, 2H), 4.35 (t, 1H), 3.48-3.20 (m, 4H), 2.61 (m, 2H), 1.72-1.09 (m, 13H). |
| A22M1B13 | $^1$H NMR (400 MHz, DMSO-d$_6$): δ 12.40 (bs, 1H), 11.02 (s, 1H), 7.3-8.4 (m, 7H), 4.65 (bs, 2H), 4.33 (t, 1H), 3.44 (m, 4H), 2.65 (m, 2H), 1.70 (m, 2H), 1.67 (s, 6H), 1.52 (m, 1H), 1.39 (m, 2H), 1.15 (m, 2H). |
| A13M1B13 | $^1$H NMR (400 MHz, DMSO-d$_6$): δ 1.15 (m, 2H) 1.40 (q, J = 6.54 Hz, 2 H) 1.51 (m, 1H) 1.59 (s, 6H) 1.68 (m, 2H) 1.79 (m, 1H) 1.91 (m, 1 H) 2.07 (m, 2H) 2.17 (m, 2H) 2.61 (t, J = 12.13 Hz, 2H) 3.24 (m, 1 H) 3.39 (d, J = 14.75 Hz, 2H) 3.47 (m, 2H) 4.35 (m, 1H) 4.49 (s, 2H) 10.19 (s, 1H) 12.22 (s, 1H) |
| A21M1B13 | $^1$H NMR (400 MHz, DMSO-d$_6$): δ 1.16 (m, 2H) 1.40 (q, J = 6.71 Hz, 2 H) 1.55 (m, 1H) 1.64 (s, 6H) 1.69 (d, J = 12.80 Hz, 2H) 2.62 (m, 2H) 3.42 (d, J = 11.83 Hz, 2H) 3.47 (m, 2H) 4.35 (t, J = 5.12 Hz, 1H) 4.58 (s, 2H) 6.62 (m, 1H) 7.83 (d, J = 1.46 Hz, 1H) 7.99 (d, J = 9.39 Hz, 2 H) 8.15 (d, J = 8.17 Hz, 2H) 8.65 (d, J = 2.44 Hz, 1H) 10.94 (s, 1H) 12.43 (s, 1H) |
| A25M1B13 | $^1$H NMR (400 MHz, DMSO-d$_6$): δ 12.02 (bs, 1H), 8.82 (bs, 1H), 7.3 (m, 5H), 7.0 (bs, 1H), 4.40 (s, 2H), 4.33 (m, 3H), 3.45 (m, 2H), 3.33 (m, 2H), 2.59 (m, 2H), 1.66 (m, 2H), 1.57 (m, 7H), 1.40 (m, 2H), 1.13 (m, 2H). |
| A27M1B13 | $^1$H NMR (400 MHz, DMSO-d$_6$): δ 12.20 (bs, 1H), 9.02 (bs, 1H), 7.45 (m, 1H), 7.31 (m, 1H), 7.12 (m, 1H), 6.81 (m, 1H), 4.47 (bs, 2H), 4.34 (t, 1H), 3.46 (m, 2H), 3.32 (m, 2H), 2.62 (m, 2H), 1.66 (m, 2H), 1.58 (m, 7H), 1.40 (m, 2H), 1.15 (m, 2H). |
| A24M1B13 | $^1$H NMR (400 MHz, DMSO-d$_6$): δ 12.03 (bs, 1H), 8.79 (bs, 1H), 7.24 (m, 1H), 7.18 (m, 3H), 6.92 (bs, 1H), 4.39 (bs, 2H), 4.35 (t, 1H), 4.31 (m, 2H), 3.46 (m, 2H), 3.33 (m, 2H), 2.56 (m, 2H), 2.3 (s, 3H), 1.65 (m, 2H), 1.58 (m, 7H), 1.40 (m, 2H), 1.13 (m, 2H). |
| A26M1B13 | $^1$H NMR (400 MHz, DMSO-d$_6$): δ 11.99 (bs, 1H), 8.66 (bs, 1H), 6.56 (bs, 1H), 4.38 (bs, 2H), 4.35 (t, 1H), 3.46 (m, 2H), 3.32 (m, 2H), 3.05 (m, 2H), 2.56 (m, 2H), 1.66 (m, 2H), 1.57 (m, 7H), 1.46 (m, 4H), 1.14 (m, 2H), 0.88 (t, 3H). |
| A12M1B13 | $^1$H NMR (400 MHz, DMSO-d$_6$): δ ppm 0.92 (d, J = 6.46 Hz, 6H) 1.12 (m, 2H) 1.39 (q, J = 6.58 Hz, 2H) 1.54 (m, 1H) 1.59 (s, 6H) 1.67 (d, J = 14.51 Hz, 2H) 2.06 (m, 1H) 2.16 (d, J = 6.95 Hz, 2H) 2.60 (m, 2 H) 3.38 (m, 2H) 3.46 (m, 2H) 4.35 (t, J = 5.12 Hz, 1H) 4.46 (s, 2H) 10.30 (s, 1H) 12.23 (s, 1H) |
| A54M1B13 | $^1$H NMR (400 MHz, DMSO-d$_6$): δ ppm 1.15 (m, 2H) 1.40 (q, J = 6.63 Hz, 2H) 1.53 (m, 1H) 1.64 (s, 6H) 1.68 (d, J = 12.93 Hz, 2H) 2.62 (m, 2H) J = 11.89 Hz, 2H) 3.42 (d, J = 11.22 Hz, 2H) 3.46 (m, 2H) 4.35 (t, J = 4.88 Hz, 1H) 4.57 (s, 2H) 7.77 (t, J = 8.72 Hz, 1H) 7.97 (d, J = 6.10 Hz, 1H) 8.30 (d, J = 7.68 Hz, 1H) 8.36 (s, 1H) 11.21 (s, 1H) 12.49 (s, 1H) |
| A01M1B27 | $^1$H NMR (400 MHz, DMSO-d$_6$): δ ppm 0.86 (t, 3H), 1.27 (m, 2H), 1.38 (m, 2H), 1.61 (s, 6H), 3.0 (m, 2H), 4.41 (m, 2H), 5.98 (bs, 1H), 7.31 (m, 2H), 8.06 (m, 2H), 10.86 (s, 1H) 12.39 (s, 1H). |
| A01M2B27 | $^1$H NMR (400 MHz, DMSO-d$_6$): δ ppm 0.78 (m, 2H), 0.86 (t, 3H), 1.27 (m, 2H), 1.38 (m, 2H), 2.06 (m, 2H), 3.0 (m, 2H), 4.41 (m, 2 H), 5.98 (bs, 1H), 7.31 (m, 2H), 8.05 (m, 2H), 10.86 (s, 1H) 12.38 (s, 1H). |
| A01M1B28 | $^1$H NMR (400 MHz, DMSO-d$_6$): δ ppm 1.00 (t, 3H), 1.62 (s, 6H), 3.04 (m, 2H), 4.42 (m, 2H), 6.01 (bs, 1H), 7.30 (m, 2H), 8.07 (m, 2 H), 10.85 (s, 1H) 12.38 (s, 1H). |
| A55M1B28 | $^1$H NMR (400 MHz, DMSO-d$_6$): δ ppm 1.00 (t, 3H), 1.49 (d, J = 7.50 Hz, 3H), 1.55 (s, 3H), 1.58 (s, 3H), 3.01 (m, 2H), 4.04 (q, 1H), 4.34 (m, 2H), 5.99 (bs, 1H), 7.48 (m, 3H), 7.87 (m, 4H), 10.61 (s, 1 H) 12.23 (s, 1H). |
| A01M2B28 | $^1$H NMR (400 MHz, DMSO-d$_6$): δ ppm 0.78 (m, 2H), 0.99 (m, 3H), 2.06 (m, 2H), 2.98 (m, 2H), 4.56 (m, 2H), 6.14 (bs, 1H), 7.33 (m, 2 H), 8.07 (m, 2H), 10.88 (s, 1H) 12.09 (s, 1H). |
| A48M2B28 | $^1$H NMR (400 MHz, DMSO-d$_6$): δ ppm 0.74 (m, 2H), 0.96 (m, 3H), 2.03 (m, 2H), 2.96 (m, 2H), 3.80 (s, 2H), 4.45 (s, 2H), 5.68 (bs, 1 H), 6.06 (bs, 1H), 7.4-8.0 (m, 7H), 10.70 (s, 1H). |
| A01M1B49 | $^1$H NMR (400 MHz, DMSO-d$_6$): δ ppm 1.06 (d, J = 6.55 Hz, 6H), 1.61 (s, 6H), 3.78 (m, 1H), 4.41 (m, 2H), 5.66 (m, 1H), 7.31 (m, 2H), 8.06 (m, 2H), 10.85 (s, 1H) 12.39 (s, 1H). |
| A48M1B49 | $^1$H NMR (400 MHz, DMSO-d$_6$): δ ppm 1.01 (d, J = 6.5 Hz, 6H), 1.56 (s, 6H), 3.76 (m, 1H), 4.29 (m, 2H), 5.66 (m, 1H), 7.47 (m, 3H), 7.78 (m, 1H), 7.85 (m, 3H), 10.67 (s, 1H) 12.24 (s, 1H). |
| A01M2B49 | $^1$H NMR (400 MHz, DMSO-d$_6$): δ ppm 0.81 (m, 2H), 1.09 (d, J = 6.64 Hz, 6H), 2.09 (m, 2H), 3.74 (m, 1H), 4.60 (m, 2H), 5.85 (m, 1H), 7.36 (m, 2H), 8.10 (m, 2H), 10.92 (s, 1H) 11.76 (s, 1H). |

TABLE V-continued

| | |
|---|---|
| A01M1B55 | $^1$H NMR (400 MHz, DMSO-$d_6$): δ ppm 1.57 (m, 2H), 1.63 (s, 6H), 1.73 (m, 2H), 2.25 (m, 1H), 2.64 (m, 2H), 3.43 (m, 2H), 4.56 (m, 2H), 6.75 (s, 1H), 7.27 (s, 1H), 7.34 (m, 2H), 8.09 (m, 2H), 10.92 (s, 1H) 12.45 (s, 1H). |
| A01M2B55 | $^1$H NMR (400 MHz, DMSO-$d_6$): δ ppm 0.96 (m, 2H), 1.55 (m, 2H), 1.71 (m, 2H), 1.82 (m, 2H), 2.34 (m, 1H), 2.75 (m, 2H), 3.48 (m, 2H), 4.67 (m, 2H), 6.75 (s, 1H), 7.28 (s, 1H), 7.35 (m, 2H), 8.10 (m, 2H), 10.98 (s, 1H) 12.19 (s, 1H). |

EXAMPLE 21

Several compounds of the invention of formula (Ia) and (Ib), being prepared as formerly reported, were also characterised by means of HPLC/Mass techniques, hence through retention time (r.t.) and Mass [M+H]$^+$.

The operative conditions are reported below:

HPLC/MS Method 1

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were provided by Millennium 4.0 and MassLynx 3.5 software.

HPLC was carried out at 25° C. at a flow rate of 1 ml/min using a RP18 Waters X Terra (4.6×50 mm, 3.5 µm) column. Mobile phase A was ammonium acetate 5 mM buffer (pH 5.5 with acetic acid/acetonitrile 95:5), and Mobile phase B was $H_2O$/acetonitrile (5:95); the gradient was from 10 to 90% B in 8 minutes then hold 90% B 2 minutes. The injection volume was 10 µl.

The mass spectometer was operated in positive and in negative ion mode, the capillary voltage was set up at 2.5 KV; the source temperature was 120° C.; cone was 10 V; full scan, mass range from 100 to 800 amu was set up.

HPLC/MS Method 2

The HPLC equipment consisted of a Waters 2790 HPLC system equipped with a 996 Waters PDA detector and Micromass mod. ZQ single quadrupole mass spectrometer, equipped with an electrospray (ESI) ion source. Instrument control, data acquisition and data processing were provided by Millennium 4.0 and MassLynx 3.5 software.

HPLC was carried out at 25° C. at a flow rate of 1 ml/min using a RP18 Waters X Terra (4.6×50 mm, 3.5 µm) column. Mobile phase A was ammonium acetate 5 mM buffer (pH 5.5 with acetic acid/acetonitrile 95:5), and Mobile phase B was $H_2O$/acetonitrile (5:95); the gradient was from 10 to 90% B in 4 min then hold 90% B 1 minute. The injection volume was 10 µl.

The mass spectometer was operated in positive and in negative ion mode, the capillary voltage was set up at 2.5 KV; the source temperature was 120° C.; cone was 10 V; full scan, mass range from 100 to 800 amu was set up.

HPLC/MS Method 3

Mass spectra were recorded on a Finnigan LCQ ion trap mass spectrometer using the electrospray (ESI) ionization technique with positive and negative ion detection. The mass spectrometer was directly connected to a SSP4000 HPLC system (Thermo Separation), equipped with an LcPal autosampler (CTC Analytics) and a UV 6000LP PDA detector (Thermo Separation). Instrument control, data acquisition and processing were performed by using Xcalibur 1.2 software. HPLC analysis were carried out at room temperature at a flow rate of 1 ml/min using an RP C18 Waters X-Terra column (4.6×50 mm; 3.5 µm).

Mobile phase A was ammonium acetate 5 mM buffer (pH 5.5 with acetic acid): acetonitrile 90:10, and Mobile phase B was ammonium acetate 5 mM buffer (pH 5.5 with acetic acid):acetonitrile 10:90; the gradient was from 0 to 100% B in 7 minutes then hold 100% B for 2 minutes before requilibration. Total LC time is 12 minutes. The injection volume was 10 µl. UV Detection was performed between 215 and 400 nm. Ions were generated under the following conditions: ESI sprayer voltage 4.0 kV, heated capillary temperature 255° C., sheath gas nitrogen with a pressure of 5.0 Bar. A full scan detection mode (from 50 to 1000 amu) was used with an MS/MS analysis of the most intense ion (normalized collision energy: 35%).

UV Detection: 215-400 nm.

HPLC/MS Method 4

The HPLC system used (Alliance 2790, with thermostated autosampler and divert valve LabPro, UV detector 2487 and satin interface, ZQ mass spectrometer with ESI interface) is a product of Waters Inc., Milford, Mass. The chemiluminescent nitrogen detector (CLND) mod. 8060 is a product of ANTEK Instruments Inc., Houston, Tex. The liquid handler Miniprep 75 is a product of Tecan Group Ltd., Maennedorf, Switzerland.

The chromatographic conditions used were as follows: The flow rate was set at 1 mL/min. Two mobile phases (mobile phase A: 0.1% formic acid, mobile phase B: 0.1% formic acid in methanol) were employed to run in 10 min a linear gradient from 5% B to 95% B, which was maintained for 2 min, and followed by re-equilibration at 5% B for the next 3 minutes. Run time was 15 min. Injection volume 10 µL, autosampler temperature 25° C., detection wavelength 220 nm.

As reported in the following table VI, some other compounds of formula (Ia) and (Ib) were prepared, each identified through the aforementioned A-M-B coding system, and further characterised through HPLC/Mass, according to the experimental conditions being above reported.

TABLE VI

| Compound | HPLC Method | r.t. (min) | [M + H]$^+$ |
|---|---|---|---|
| A01M1B09 | 3 | 4.60 | 386.0 |
| A01M1B10 | 3 | 3.52 | 388.0 |
| A01M1B11 | 1 | 5.55 | 400.5 |
| A01M1B16 | 1 | 2.82 | 415.5 |
| A01M1B18 | 1 | 3.06 | 455.5 |
| A01M1B23 | 3 | 2.71 | 406.0 |
| A01M1B24 | 3 | 5.05 | 434.0 |
| A01M1B25 | 3 | 3.10 | 376.0 |
| A01M1B26 | 3 | 2.80 | 362.1 |
| A01M1B29 | 1 | 4.00 | 431.5 |
| A01M1B30 | 1 | 3.39 | 402.4 |
| A01M1B31 | 1 | 2.60 | 431.5 |
| A01M1B32 | 3 | 6.07 | 430.0 |
| A01M1B33 | 3 | 3.67 | 416.0 |
| A01M1B35 | 1 | 3.66 | 402.4 |
| A01M1B36 | 1 | 2.70 | 401.5 |
| A01M1B37 | 1 | 4.75 | 404.4 |
| A01M1B38 | 1 | 2.76 | 401.5 |

TABLE VI-continued

| Compound | HPLC Method | r.t. (min) | [M + H]+ |
|---|---|---|---|
| A01M1B40 | 1 | 2.74 | 475.5 |
| A01M1B41 | 3 | 4.75 | 510.1 |
| A01M1B42 | 1 | 3.79 | 480.5 |
| A01M1B46 | 3 | 2.68 | 419.0 |
| A01M1B49 | 3 | 3.87 | 360.0 |
| A02M1B11 | 2 | 2.35 | 400.5 |
| A02M1B16 | 2 | 1.09 | 415.5 |
| A02M1B18 | 2 | 1.16 | 455.5 |
| A02M1B29 | 2 | 1.64 | 431.5 |
| A02M1B30 | 2 | 1.36 | 402.4 |
| A02M1B31 | 2 | 0.96 | 431.5 |
| A02M1B35 | 2 | 1.48 | 402.4 |
| A02M1B36 | 2 | 1.01 | 401.5 |
| A02M1B37 | 2 | 1.96 | 404.4 |
| A02M1B38 | 2 | 1.03 | 401.5 |
| A02M1B40 | 2 | 1.01 | 475.5 |
| A02M1B42 | 2 | 1.59 | 480.5 |
| A04M1B09 | 1 | 5.02 | 404.4 |
| A04M1B10 | 1 | 3.77 | 406.4 |
| A04M1B11 | 1 | 5.57 | 418.5 |
| A04M1B25 | 1 | 3.25 | 394.4 |
| A04M1B27 | 1 | 4.72 | 392.4 |
| A04M1B28 | 1 | 3.68 | 364.4 |
| A04M1B30 | 1 | 3.34 | 420.4 |
| A04M1B33 | 1 | 3.88 | 434.5 |
| A04M1B34 | 1 | 3.40 | 447.5 |
| A04M1B41 | 1 | 5.25 | 528.5 |
| A04M1B49 | 1 | 4.18 | 378.4 |
| A05M1B11 | 1 | 6.03 | 418.5 |
| A05M1B18 | 1 | 3.08 | 473.5 |
| A05M1B29 | 1 | 4.30 | 449.5 |
| A05M1B30 | 1 | 0.72 | 420.4 |
| A05M1B31 | 1 | 2.66 | 449.5 |
| A05M1B35 | 1 | 4.00 | 420.4 |
| A05M1B36 | 1 | 2.83 | 419.4 |
| A05M1B37 | 1 | 5.17 | 422.4 |
| A05M1B38 | 1 | 2.79 | 419.4 |
| A05M1B40 | 1 | 2.82 | 493.5 |
| A05M1B42 | 1 | 4.07 | 498.5 |
| A06M1B11 | 1 | 6.09 | 416.9 |
| A06M1B16 | 1 | 3.17 | 431.9 |
| A06M1B18 | 1 | 3.39 | 472.0 |
| A06M1B29 | 1 | 4.42 | 447.9 |
| A06M1B31 | 1 | 2.99 | 447.9 |
| A06M1B36 | 1 | 3.04 | 417.9 |
| A06M1B39 | 1 | 3.15 | 447.0 |
| A06M1B40 | 1 | 3.08 | 492.0 |
| A06M1B42 | 1 | 4.17 | 497.0 |
| A07M1B11 | 2 | 3.07 | 450.5 |
| A07M1B16 | 2 | 1.78 | 465.5 |
| A07M1B18 | 2 | 1.86 | 505.6 |
| A07M1B29 | 2 | 2.36 | 481.5 |
| A07M1B30 | 2 | 2.11 | 452.4 |
| A07M1B31 | 2 | 1.69 | 481.5 |
| A07M1B35 | 2 | 2.24 | 452.4 |
| A07M1B36 | 2 | 1.72 | 451.5 |
| A07M1B37 | 2 | 2.73 | 454.4 |
| A07M1B38 | 2 | 1.71 | 451.5 |
| A07M1B40 | 2 | 1.73 | 525.5 |
| A07M1B42 | 2 | 2.25 | 530.5 |
| A10M1B11 | 1 | 3.83 | 388.5 |
| A10M1B16 | 1 | 2.56 | 403.5 |
| A10M1B18 | 1 | 2.58 | 443.6 |
| A10M1B29 | 1 | 3.76 | 419.5 |
| A10M1B30 | 1 | 3.13 | 390.5 |
| A10M1B31 | 1 | 2.24 | 419.5 |
| A10M1B37 | 1 | 4.45 | 392.5 |
| A10M1B38 | 1 | 2.35 | 389.5 |
| A10M1B40 | 1 | 2.34 | 463.6 |
| A10M1B42 | 1 | 3.54 | 468.6 |
| A12M1B09 | 1 | 4.43 | 348.5 |
| A12M1B10 | 1 | 3.18 | 350.4 |
| A12M1B25 | 1 | 2.71 | 338.4 |
| A12M1B28 | 1 | 3.08 | 308.4 |
| A12M1B31 | 1 | 1.89 | 393.5 |
| A12M1B33 | 1 | 3.40 | 378.5 |
| A12M1B41 | 1 | 4.80 | 472.6 |
| A12M1B49 | 1 | 3.56 | 322.4 |
| A13M1B09 | 1 | 4.24 | 346.4 |
| A13M1B10 | 1 | 2.98 | 348.4 |
| A13M1B11 | 1 | 4.82 | 360.5 |
| A13M1B25 | 1 | 2.52 | 336.4 |
| A13M1B28 | 1 | 2.86 | 306.4 |
| A13M1B30 | 1 | 2.66 | 362.4 |
| A13M1B31 | 1 | 1.86 | 391.5 |
| A13M1B33 | 1 | 3.22 | 376.5 |
| A13M1B41 | 1 | 4.67 | 470.6 |
| A13M1B49 | 1 | 3.37 | 320.4 |
| A14M1B09 | 1 | 3.80 | 332.4 |
| A14M1B10 | 1 | 2.57 | 334.4 |
| A14M1B11 | 4 | 8.32 | 346.2 |
| A14M1B30 | 1 | 2.28 | 348.4 |
| A14M1B31 | 1 | 1.39 | 377.5 |
| A14M1B33 | 1 | 2.87 | 362.4 |
| A14M1B34 | 1 | 2.41 | 375.4 |
| A14M1B35 | 1 | 2.52 | 348.4 |
| A14M1B41 | 1 | 4.30 | 456.5 |
| A14M1B49 | 1 | 2.94 | 306.4 |
| A16M1B09 | 1 | 5.93 | 452.4 |
| A16M1B10 | 1 | 4.78 | 454.4 |
| A16M1B11 | 1 | 6.43 | 466.5 |
| A16M1B25 | 1 | 4.27 | 442.4 |
| A16M1B28 | 1 | 4.73 | 412.4 |
| A16M1B30 | 1 | 4.32 | 468.4 |
| A16M1B31 | 1 | 3.37 | 497.5 |
| A16M1B32 | 1 | 5.20 | 496.5 |
| A16M1B33 | 1 | 4.82 | 482.5 |
| A16M1B34 | 1 | 4.34 | 495.5 |
| A16M1B35 | 1 | 4.60 | 468.4 |
| A16M1B49 | 1 | 5.15 | 426.4 |
| A17M1B11 | 2 | 3.37 | 474.6 |
| A17M1B16 | 2 | 2.29 | 489.6 |
| A17M1B18 | 2 | 2.33 | 529.7 |
| A17M1B29 | 2 | 2.60 | 505.6 |
| A17M1B30 | 2 | 2.39 | 476.5 |
| A17M1B31 | 2 | 2.08 | 505.6 |
| A17M1B35 | 2 | 2.53 | 476.5 |
| A17M1B36 | 2 | 2.08 | 475.6 |
| A17M1B37 | 2 | 3.01 | 478.5 |
| A21M1B09 | 1 | 4.92 | 434.5 |
| A21M1B10 | 1 | 3.78 | 436.5 |
| A21M1B25 | 1 | 3.33 | 424.5 |
| A21M1B28 | 1 | 3.71 | 394.4 |
| A21M1B31 | 1 | 2.66 | 479.6 |
| A21M1B33 | 1 | 3.90 | 464.5 |
| A21M1B49 | 1 | 4.13 | 408.5 |
| A22M1B09 | 1 | 5.54 | 418.5 |
| A22M1B10 | 1 | 4.65 | 420.5 |
| A22M1B11 | 1 | 6.05 | 432.5 |
| A22M1B25 | 1 | 3.81 | 408.5 |
| A22M1B27 | 1 | 5.27 | 406.5 |
| A22M1B28 | 1 | 4.33 | 378.4 |
| A22M1B30 | 1 | 3.86 | 434.5 |
| A22M1B31 | 1 | 2.92 | 463.6 |
| A22M1B32 | 1 | 4.81 | 462.6 |
| A22M1B33 | 1 | 4.40 | 448.5 |
| A22M1B34 | 1 | 3.90 | 461.5 |
| A22M1B35 | 1 | 4.46 | 434.5 |
| A22M1B41 | 1 | 4.11 | 542.6 |
| A22M1B49 | 1 | 4.77 | 392.5 |
| A23M1B09 | 1 | 5.91 | 418.5 |
| A23M1B10 | 1 | 4.67 | 420.5 |
| A23M1B11 | 1 | 6.45 | 432.5 |
| A23M1B25 | 1 | 4.16 | 408.5 |
| A23M1B27 | 1 | 5.56 | 406.5 |
| A23M1B28 | 1 | 4.62 | 378.4 |
| A23M1B30 | 1 | 4.20 | 434.5 |
| A23M1B31 | 1 | 3.21 | 463.6 |
| A23M1B32 | 1 | 5.13 | 462.6 |
| A23M1B33 | 1 | 4.72 | 448.5 |
| A23M1B34 | 1 | 4.24 | 461.5 |
| A23M1B35 | 1 | 4.49 | 434.5 |
| A23M1B41 | 1 | 5.98 | 542.6 |
| A23M1B49 | 1 | 5.05 | 392.5 |
| A24M1B09 | 1 | 5.02 | 411.5 |
| A24M1B10 | 1 | 3.91 | 413.5 |

TABLE VI-continued

| Compound | HPLC Method | r.t. (min) | [M + H]+ |
|---|---|---|---|
| A24M1B28 | 1 | 3.87 | 371.5 |
| A24M1B31 | 1 | 2.73 | 456.6 |
| A24M1B33 | 1 | 4.05 | 441.5 |
| A24M1B49 | 1 | 4.28 | 385.5 |
| A25M1B09 | 1 | 4.65 | 397.5 |
| A25M1B10 | 1 | 3.53 | 399.5 |
| A25M1B25 | 1 | 3.13 | 387.5 |
| A25M1B28 | 1 | 3.48 | 357.4 |
| A25M1B30 | 1 | 3.20 | 413.5 |
| A25M1B31 | 1 | 2.26 | 442.5 |
| A25M1B33 | 1 | 3.47 | 427.5 |
| A25M1B41 | 1 | 4.94 | 521.6 |
| A25M1B49 | 1 | 3.91 | 371.5 |
| A26M1B09 | 1 | 3.87 | 349.4 |
| A26M1B10 | 1 | 2.72 | 351.4 |
| A26M1B28 | 1 | 2.62 | 309.4 |
| A26M1B33 | 1 | 3.00 | 379.5 |
| A26M1B49 | 1 | 3.06 | 323.4 |
| A27M1B09 | 1 | 5.34 | 401.5 |
| A27M1B10 | 1 | 4.13 | 403.4 |
| A27M1B25 | 1 | 3.65 | 391.4 |
| A27M1B31 | 1 | 2.85 | 446.5 |
| A27M1B33 | 1 | 4.22 | 431.5 |
| A27M1B49 | 1 | 4.52 | 375.4 |
| A30M1B09 | 1 | 4.78 | 368.5 |
| A30M1B10 | 1 | 3.53 | 370.4 |
| A30M1B11 | 1 | 5.33 | 382.5 |
| A30M1B25 | 1 | 3.04 | 358.4 |
| A30M1B27 | 1 | 4.45 | 356.4 |
| A30M1B28 | 1 | 3.43 | 328.4 |
| A30M1B30 | 1 | 3.13 | 384.4 |
| A30M1B31 | 1 | 2.27 | 413.5 |
| A30M1B33 | 1 | 3.69 | 398.5 |
| A30M1B34 | 1 | 3.21 | 411.5 |
| A30M1B35 | 1 | 3.38 | 384.4 |
| A30M1B41 | 1 | 5.06 | 492.6 |
| A30M1B49 | 1 | 3.91 | 342.4 |
| A48M1B09 | 3 | 5.30 | 432.1 |
| A48M1B10 | 3 | 4.18 | 434.1 |
| A48M1B23 | 3 | 3.38 | 452.1 |
| A48M1B24 | 3 | 3.78 | 480.1 |
| A48M1B25 | 3 | 3.83 | 422.1 |
| A48M1B26 | 3 | 3.48 | 408.2 |
| A48M1B30 | 3 | 4.00 | 448.2 |
| A48M1B31 | 3 | 3.22 | 477.1 |
| A48M1B32 | 3 | 4.28 | 476.3 |
| A48M1B33 | 3 | 4.23 | 462.1 |
| A48M1B40 | 3 | 3.33 | 521.3 |
| A48M1B41 | 3 | 4.72 | 556.2 |
| A48M1B46 | 3 | 3.43 | 465.1 |
| A48M1B49 | 3 | 4.77 | 406.1 |
| A53M1B09 | 1 | 3.10 | 417.5 |
| A53M1B28 | 1 | 2.02 | 377.5 |
| A53M1B49 | 1 | 2.37 | 391.5 |
| A54M1B09 | 1 | 5.87 | 436.4 |
| A54M1B10 | 1 | 4.65 | 438.4 |
| A54M1B11 | 4 | 9.71 | 450.1 |
| A54M1B25 | 1 | 4.14 | 426.4 |
| A54M1B28 | 1 | 4.60 | 396.4 |
| A54M1B31 | 1 | 3.22 | 481.5 |
| A54M1B33 | 1 | 4.70 | 466.5 |
| A54M1B34 | 1 | 4.20 | 479.5 |
| A54M1B35 | 1 | 4.46 | 452.4 |
| A54M1B41 | 1 | 5.93 | 560.6 |
| A54M1B49 | 1 | 5.05 | 410.4 |
| A01M2B11 | 2 | 2.75 | 398.5 |
| A01M2B16 | 2 | 1.40 | 413.5 |
| A01M2B18 | 2 | 1.50 | 453.5 |
| A01M2B29 | 2 | 2.08 | 429.5 |
| A01M2B30 | 2 | 1.71 | 400.4 |
| A01M2B31 | 2 | 1.27 | 429.5 |
| A01M2B35 | 2 | 1.84 | 400.4 |
| A01M2B36 | 2 | 1.31 | 399.2 |
| A01M2B37 | 2 | 2.33 | 402.4 |
| A01M2B38 | 2 | 1.34 | 399.4 |
| A01M2B40 | 2 | 1.34 | 473.5 |
| A01M2B42 | 2 | 1.93 | 478.5 |
| A06M2B09 | 1 | 5.52 | 400.9 |
| A06M2B11 | 1 | 6.04 | 414.9 |
| A06M2B16 | 1 | 2.95 | 429.9 |
| A06M2B18 | 1 | 3.16 | 470.0 |
| A06M2B29 | 1 | 4.57 | 445.9 |
| A06M2B30 | 1 | 3.82 | 416.9 |
| A06M2B31 | 1 | 2.90 | 445.9 |
| A06M2B35 | 1 | 4.08 | 416.9 |
| A06M2B36 | 1 | 2.94 | 415.9 |
| A06M2B37 | 1 | 5.20 | 418.9 |
| A06M2B38 | 1 | 3.00 | 415.9 |
| A06M2B40 | 1 | 3.03 | 490.0 |
| A07M2B11 | 2 | 3.10 | 448.5 |
| A07M2B16 | 2 | 1.80 | 463.5 |
| A07M2B18 | 2 | 1.90 | 503.5 |
| A07M2B29 | 2 | 2.46 | 479.5 |
| A07M2B30 | 2 | 2.13 | 450.4 |
| A07M2B31 | 2 | 1.71 | 479.5 |
| A07M2B35 | 2 | 2.26 | 450.4 |
| A07M2B36 | 2 | 1.74 | 449.4 |
| A07M2B37 | 2 | 2.75 | 452.4 |
| A07M2B38 | 2 | 1.78 | 449.4 |
| A07M2B40 | 2 | 1.76 | 523.5 |
| A07M2B42 | 2 | 2.29 | 528.5 |
| A17M2B16 | 2 | 2.10 | 487.6 |
| A17M2B18 | 2 | 2.17 | 527.6 |
| A17M2B29 | 2 | 2.73 | 503.6 |
| A17M2B30 | 2 | 2.40 | 474.5 |
| A17M2B31 | 2 | 2.01 | 503.6 |
| A17M2B35 | 2 | 2.55 | 474.5 |
| A17M2B36 | 2 | 2.03 | 473.5 |
| A17M2B37 | 2 | 3.05 | 476.5 |
| A17M2B38 | 2 | 2.07 | 473.5 |
| A17M2B40 | 2 | 2.04 | 547.6 |
| A17M2B42 | 2 | 2.55 | 552.6 |

The invention claimed is:

1. A compound represented by formula (Ib)

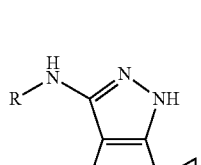

(Ib)

wherein

R is a group —COR$^a$, —CONHR$^a$ or —CONR$^a$R$^b$ wherein R$^a$ and R$^b$ are, each independently, hydrogen or an optionally substituted group selected from straight or branched $C_1$-$C_6$ alkyl, $C_3$-$C_6$ cycloalkyl, aryl, arylalkyl, heterocyclyl or heterocyclylalkyl or; together with the nitrogen atom to which they are bonded, R$^a$ and R$^b$ may form an optionally substituted 5 or 6 membered heterocycle optionally containing one additional heteroatom or heteroatomic group selected among N, NH, O or S;

R$_1$ is tert-butyl;

or a pharmaceutically acceptable salt thereof.

2. A compound of formula (Ib) according to claim 1 wherein R is a group —COR$^a$, R$^a$ is as defined in claim 1 and R1 is tert-butyl.

3. A compound of formula (Ib) according to claim 1 wherein R is a group —CONHR$^a$, R$^a$ is as defined in claim 1 and R$_1$ is tert-butyl.

4. A compound of formula (Ib) according to claim 1 wherein R is a group —CONR$^a$R$^b$, R$^a$ and R$^b$ are as defined in claim 1 and R$_1$ is tert-butyl.

5. A compound of formula (Ib), according to claim 1, wherein any of R$^a$ and R$^b$ is a group, as defined in claim 1, optionally further substituted in one or more of their free positions, by groups independently selected from halogen, nitro, oxo groups (=O), cyano, alkyl, perfluorinated alkyl, perfluorinated alkoxy, alkenyl, alkynyl, hydroxyalkyl, aryl, arylalkyl, heterocyclyl, cycloalkyl, hydroxy, alkoxy, aryloxy, heterocyclyloxy, methylenedioxy, alkylcarbonyloxy, arylcarbonyloxy, cycloalkenyloxy, alkylideneaminooxy, carboxy, alkoxycarbonyl, aryloxycarbonyl, cycloalkyloxycarbonyl, amino, ureido, alkylamino, dialkylamino, arylamino, diarylamino, formylamino, alkylcarbonylamino, arylcarbonylamino, heterocyclylcarbonylamino, alkoxycarbonylamino, alkoxyimino, alkylsulfonylamino, arylsulfonylamino, formyl, alkylcarbonyl, arylcarbonyl, cycloalkylcarbonyl, heterocyclylcarbonyl, aminocarbonyl, alkylaminocarbonyl, dialkylaminocarbonyl, alkylsulfonyl, arylsulfonyl, aminosulfonyl, alkylaminosulfonyl, dialkylaminosulfonyl, arylthio and alkylthio.

6. A compound of formula (Ib) according to claim 1, optionally in the form of a pharmaceutically acceptable salt, the compound being
N-[5-(2,2-dimethylpropanoyl)-2,4,5,6-tetrahydropyrrolo[3,4-c]pyrazol-6-spirocyclopropan-3-yl]-4-fluorobenzamide.

7. A compound of formula (Ib) according to claim 1, optionally in the form of a pharmaceutically acceptable salt, having the following structure:

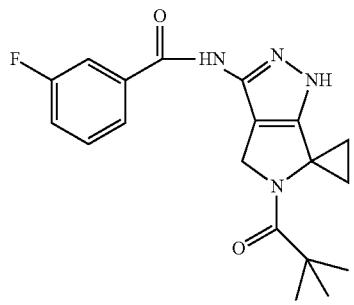

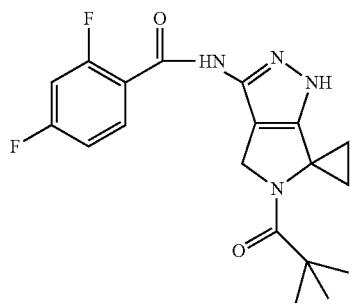

-continued

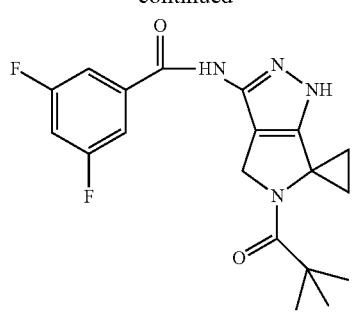

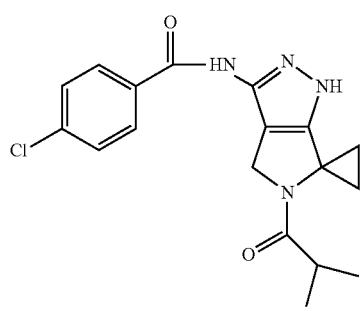

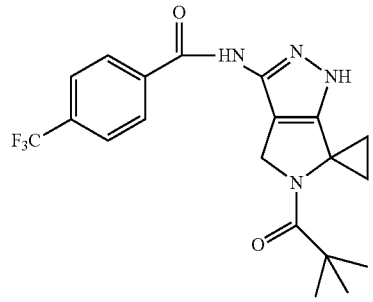

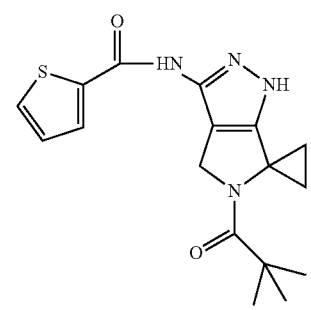

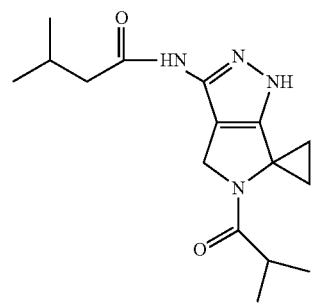

-continued

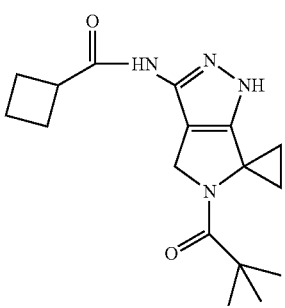

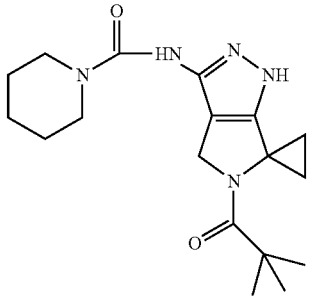

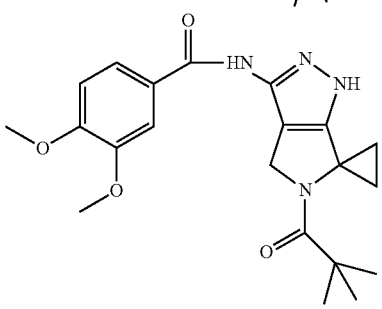

8. A library of two or more compounds of formula (Ib)

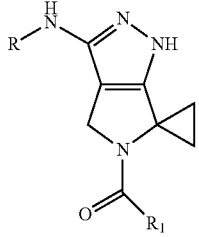

(Ib)

wherein
R is a group —COR$^a$, —CONHR$^a$ or —CONR$^a$R$^b$ wherein R$^a$ and R$^b$ are, each independently, hydrogen or an optionally substituted group selected from straight or branched $C_1$-$C_6$ alkyl, $C_3$-$C_6$ cycloalkyl, aryl, arylalkyl, heterocyclyl or heterocyclylalkyl or; together with the nitrogen atom to which they are bonded, R$^a$ and R$^b$ may form an optionally substituted 5 or 6 membered heterocycle optionally containing one additional heteroatom or heteroatomic group selected among N, NH, O or S;
$R_1$ is tert-butyl;
or a pharmaceutically acceptable salt thereof.

9. A pharmaceutical composition comprising a therapeutically effective amount of a compound of formula (Ib), as defined in claim 1, and at least one pharmaceutically acceptable excipient, carrier and/or diluents.

10. A pharmaceutical composition according to claim 9 further comprising one or more chemotherapeutic agents.

11. A method of treating ovarian cancer in a mammal comprising the steps of:
administering to said mammal a product or kit comprising at least one of the following compounds; N-[5-(2,2-dimethylpropanoyl)-1,4,5,6-tetrahydropyrrolo[3,4-c]pyrazol-6-spirocyclopropan-3-yl]-4-fluorobenzamide; N-[5-(2,2-dimethylpropanoyl)-1,4,5,6-tetrahydropyrrolo[3,4-c]pyrazol-6-spirocyclopropan-3-yl]-3-fluorophenyl; N-[5-(2,2-dimethylpropanoyl)-1,4,5,6-tetrahydropyrrolo[3,4-c]pyrazol-6-spirocyclopropan-3-yl]-2,4-difluorophenyl; N-[5-(2,2-dimethylpropanoyl)-1,4,5,6-tetrahydropyrrolo[3,4-c]pyrazol-6-spirocyclopropan-3-yl]-3,5-difluorophenyl; N-[5-(2,2-dimethylpropanoyl)-1,4,5,6-tetrahydropyrrolo[3,4-c]pyrazol-6-spirocyclopropan-3-yl]-4-chlorophenyl; N-[5-(2,2-dimethylpropanoyl)-1,4,5,6-tetrahydropyrrolo[3,4-c]pyrazol-6-spirocyclopropan-3-yl]-4-CF$_3$-phenyl; N-[5-(2,2-dimethylpropanoyl)-1,4,5,6-tetrahydropyrrolo[3,4-c]pyrazol-6-spirocyclopropan-3-yl]-2-thienyl; N-[5-(2,2-dimethylpropanoyl)-1,4,5,6-tetrahydropyrrolo[3,4-c]pyrazol-6-spirocyclopropan-3-yl]-cyclopropyl; N-[5-(2,2-dimethylpropanoyl)-1,4,5,6-tetrahydropyrrolo[3,4-c]pyrazol-6-spirocyclopropan-3-yl]-tert-butyl or a pharmaceutical composition thereof, and administering one or more chemotherapeutic agents, simultaneously, separately or sequentially with the product or kit.

12. A method of treating ovarian cancer in a mammal comprising the steps of:

administering to said mammal at least one of the following compounds N-[5-(2,2-dimethylpropanoyl)-1,4,5,6-tetrahydropyrrolo[3,4-c]pyrazol-6-spirocyclopropan-3-yl]-4-fluorobenzamide; N-[5-(2,2-dimethylpropanoyl)-1,4,5,6-tetrahydropyrrolo[3,4-c]pyrazol-6-spirocyclopropan-3-yl]-3-fluorophenyl; N-[5-(2,2-dimethylpropanoyl)-1,4,5,6-tetrahydropyrrolo[3,4-c]pyrazol-6-spirocyclopropan-3-yl]-2,4-difluorophenyl; N-[5-(2,2-dimethylpropanoyl)-1,4,5,6-tetrahydropyrrolo[3,4-c]pyrazol-6-spirocyclopropan-3-yl]-3,5-difluorophenyl; N-[5-(2,2-dimethylpropanoyl)-1,4,5,6-tetrahydropyrrolo[3,4-c]pyrazol-6-spirocyclopropan-3-yl]-4-chlorophenyl; N-[5-(2,2-dimethylpropanoyl)-1,4,5,6-tetrahydropyrrolo[3,4-c]pyrazol-6-spirocyclopropan-3-yl]-4-CF$_3$-phenyl; N-[5-(2,2-dimethylpropanoyl)-1,4,5,6-tetrahydropyrrolo[3,4-c]pyrazol-6-spirocyclopropan-3-yl]-2-thienyl; N-[5-(2,2-dimethylpropanoyl)-1,4,5,6-tetrahydropyrrolo[3,4-c]pyrazol-6-spirocyclopropan-3-yl]-cyclopropyl; N-[5-(2,2-dimethylpropanoyl)-1,4,5,6-tetrahydropyrrolo[3,4-c]pyrazol-6-spirocyclopropan-3-yl]-tert-butyl.

13. A pharmaceutical composition comprising a therapeutically effective amount of a compound, as defined in claim 1, and a chemotherapeutic agent selected from the group consisting of cytostatic or cytotoxic agents, antibiotic-type agents, alkylating agents, antimetabolite agents, hormonal agents, immunological agents, interferon-type agents, cyclooxygenase inhibitors, matrixmetalloprotease inhibitors, telomerase inhibitors, tyrosine kinase inhibitors, anti-grow factor receptor agents, anti-HER agents, anti-EGFR agents, anti-angiogenesis agents, farnesyl transferase inhibitors, ras-raf signal transduction pathway inhibitors, cell cycle inhibitors, cdks inhibitors, tubulin binding agents, topoisomerase I inhibitors, typoisomerase II inhibitors and mixtures thereof.

14. A method of treating ovarian cancer in a mammal comprising the steps of:

administering to said mammal a product or kit comprising at least one of the following compounds N-[5-(2,2-dimethylpropanoyl)-1,4,5,6-tetrahydropyrrolo[3,4-c]pyrazol-6-spirocyclopropan-3-yl]-4-fluorobenzamide; N-[5-(2,2-dimethylpropanoyl)-1,4,5,6-tetrahydropyrrolo[3,4-c]pyrazol-6-spirocyclopropan-3-yl]-3-fluorophenyl; N-[5-(2,2-dimethylpropanoyl)-1,4,5,6-tetrahydropyrrolo[3,4-c]pyrazol-6-spirocyclopropan-3-yl]-2,4-difluorophenyl; N-[5-(2,2-dimethylpropanoyl)-1,4,5,6-tetrahydropyrrolo[3,4-c]pyrazol-6-spirocyclopropan-3-yl]-3,5-difluorophenyl; N-[5-(2,2-dimethylpropanoyl)-1,4,5,6-tetrahydropyrrolo[3,4-c]pyrazol-6-spirocyclopropan-3-yl]-4-chlorophenyl; N-[5-(2,2-dimethylpropanoyl)-1,4,5,6-tetrahydropyrrolo[3,4-c]pyrazol-6-spirocyclopropan-3-yl]-4-CF$_3$-phenyl; N-[5-(2,2-dimethylpropanoyl)-1,4,5,6-tetrahydropyrrolo[3,4-c]pyrazol-6-spirocyclopropan-3-yl]-2-thienyl; N-[5-(2,2-dimethylpropanoyl)-1,4,5,6-tetrahydropyrrolo[3,4-c]pyrazol-6-spirocyclopropan-3-yl]-cyclopropyl; N-[5-(2,2-dimethylpropanoyl)-1,4,5,6-tetrahydropyrrolo[3,4-c]pyrazol-6-spirocyclopropan-3-yl]-tert-butyl, and administering a chemotherapeutic agent to said mammal selected from the group consisting of cytostatic or cytotoxic agents, antibiotic-type agents, alkylating agents, antimetabolite agents, hormonal agents, immunological agents, interferon-type agents, cyclooxygenase inhibitors, matrixmetalloprotease inhibitors, telomerase inhibitors, tyrosine kinase inhibitors, anti-grow factor receptor agents, anti-HER agents, anti-EGFR agents, anti-angiogenesis agents, farnesyl transferase inhibitors, ras-raf signal transduction pathway inhibitors, cell cycle inhibitors, cdks inhibitors, tubulin binding agents, topoisomerase I inhibitors, typoisomerase II inhibitors and mixtures thereof simultaneously, separately or sequentially with the product or kit.

* * * * *